US008263139B2

(12) United States Patent
Tripp et al.

(10) Patent No.: US 8,263,139 B2
(45) Date of Patent: *Sep. 11, 2012

(54) **PROTEIN KINASE MODULATION BY HOPS AND *ACACIA* PRODUCTS**

(75) Inventors: Matthew L. Tripp, Gig Harbor, WA (US); John G. Babish, Brooktondale, NY (US); Linda M. Pacioretty, Brooktondale, NY (US); Jeffrey S. Bland, Fox Island, WA (US); Amy J. Hall, Gig Harbor, WA (US); Veera Konda, Gig Harbor, WA (US); Anu Desai, Gig Harbor, WA (US)

(73) Assignee: Metaproteonics, LLC, San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/501,393

(22) Filed: Aug. 9, 2006

(65) Prior Publication Data

US 2007/0042063 A1 Feb. 22, 2007

Related U.S. Application Data

(60) Provisional application No. 60/706,984, filed on Aug. 9, 2005, provisional application No. 60/748,931, filed on Dec. 9, 2005.

(51) Int. Cl.
*A61K 36/00* (2006.01)
(52) U.S. Cl. ........................................ 424/725; 424/779
(58) Field of Classification Search .................. None
See application file for complete search history.

(56) References Cited

U.S. PATENT DOCUMENTS

| | | | |
|---|---|---|---|
| 3,451,821 A | 6/1969 | Todd et al. |
| 3,536,495 A | 10/1970 | Westermann et al. |
| 3,552,975 A | 1/1971 | Worden, et al. |
| 3,720,517 A | 3/1973 | Bavisotto et al. |
| 3,932,603 A | 1/1976 | Haas |
| 3,933,919 A | 1/1976 | Wilkinson |
| 3,965,188 A | 6/1976 | Westermann et al. |
| 4,123,561 A | 10/1978 | Grant |
| 4,133,903 A | 1/1979 | Thiele et al. |
| 4,148,873 A | 4/1979 | Owades |
| 4,154,865 A | 5/1979 | Grant |
| 4,170,638 A | 10/1979 | Owades |
| 4,389,421 A | 6/1983 | Palamand |
| 4,401,684 A | 8/1983 | Versluys |
| 4,473,551 A | 9/1984 | Schinitsky |
| 4,554,170 A | 11/1985 | Panzer et al. |
| 4,590,296 A | 5/1986 | Cowles et al. |
| 4,644,084 A | 2/1987 | Cowles et al. |
| 4,692,280 A | 9/1987 | Spinelli |
| 4,758,445 A | 7/1988 | Klusters |
| 4,767,640 A | 8/1988 | Goldstein et al. |
| 4,857,554 A | 8/1989 | Kallimanis |
| 5,006,337 A | 4/1991 | Motitschke et al. |
| 5,013,571 A | 5/1991 | Hay |
| 5,041,300 A | 8/1991 | Todd et al. |
| 5,073,396 A | 12/1991 | Todd, Jr. |
| 5,082,975 A | 1/1992 | Todd, Jr. et al. |
| 5,155,276 A | 10/1992 | Paul |
| 5,166,449 A | 11/1992 | Todd, Jr. et al. |
| 5,264,236 A | 11/1993 | Ogasahara et al. |
| 5,286,506 A | 2/1994 | Millis et al. |
| 5,296,637 A | 3/1994 | Stegink et al. |
| 5,370,863 A | 12/1994 | Barney et al. |
| 5,387,425 A | 2/1995 | Hsu et al. |
| 5,604,263 A | 2/1997 | Tobe et al. |
| 5,641,517 A | 6/1997 | Eskeland et al. |
| 5,827,895 A | 10/1998 | Nutter et al. |
| 5,866,162 A | 2/1999 | Grattan |
| 5,919,813 A | 7/1999 | De Juan |
| 5,968,539 A | 10/1999 | Beerse et al. |
| 6,020,019 A | 2/2000 | Ting et al. |
| 6,129,907 A | 10/2000 | Sreenivasan et al. |
| 6,200,594 B1 | 3/2001 | Ernest et al. |
| 6,210,701 B1 | 4/2001 | Darland et al. |
| 6,224,871 B1 | 5/2001 | Hastings et al. |
| 6,264,995 B1 | 7/2001 | Newmark et al. |
| 6,291,483 B1 | 9/2001 | Upadhyay et al. |
| 6,383,527 B1 | 5/2002 | Artman et al. |
| 6,391,346 B1 | 5/2002 | Newmark et al. |
| 6,440,465 B1 | 8/2002 | Meisner |
| 6,447,762 B1 | 9/2002 | Galcerá |
| 6,482,456 B1 | 11/2002 | Yokoo et al. |
| 6,492,429 B1 | 12/2002 | Graus et al. |

(Continued)

FOREIGN PATENT DOCUMENTS

CN 1203268 12/1998

(Continued)

OTHER PUBLICATIONS

El-Toumy et al., Polyphenols from *Acacia nilotica* leaves and evaluation of antihyperglycemic effect of aqueous extract, Bulletin of the Faculty of Pharmacy (2004), 42 (2), 317-325.*
Kiosseva et al., Mitogen-activated protein kinase signaling abnormalities in the cerebellum in major psychiatric disorders, Society for Neuroscience Abstract Viewer and Itinerary Planner, (2003) vol. 2003, pp. Abstract No. 447.7.*
Bohm et al, cAMP concentrations, cAMP dependent protein kinase activity, and phospholamban in non-failing and failing myocardium, Cardiovascular research, (Nov. 1994) vol. 28, No. 11, pp. 1713-1719.*
Fleming et al, The mitogen-activated protein kinase pathway tonically inhibits both basal and IGF-I-stimulated IGF-binding protein-5 production in mammary epithelial cells, The Journal of endocrinology, (Aug. 2007) vol. 194, No. 2, pp. 349-359.*

(Continued)

*Primary Examiner* — Qiuwen Mi
(74) *Attorney, Agent, or Firm* — McDermott Will & Emery LLP

(57) ABSTRACT

Botanical compounds to modulate kinase activity are disclosed. The compounds and methods disclosed also inhibit expression of COX-2, inhibit synthesis of prostaglandins selectively in target cells, and inhibit inflammatory response selectively. The compositions contain at least one fraction isolated or derived from hops or *Acacia*.

5 Claims, 34 Drawing Sheets

U.S. PATENT DOCUMENTS

| | | |
|---|---|---|
| 6,583,322 B1 | 6/2003 | Shalai et al. |
| 6,689,388 B2 | 2/2004 | Kuhrts |
| 6,716,624 B2 | 4/2004 | Harrison et al. |
| 6,790,459 B1 * | 9/2004 | Cheng et al. ............. 424/468 |
| 6,801,860 B1 | 10/2004 | Dessen et al. |
| 7,078,062 B2 | 7/2006 | Haas |
| 7,144,590 B2 | 12/2006 | Kuhrts |
| 7,195,785 B2 | 3/2007 | Babish et al. |
| 7,205,151 B2 | 4/2007 | Babish et al. |
| 7,270,835 B2 | 9/2007 | Tripp et al. |
| 7,279,185 B2 | 10/2007 | Babish et al. |
| 7,332,185 B2 | 2/2008 | Babish et al. |
| 7,431,948 B2 | 10/2008 | Tripp et al. |
| 2002/0028852 A1 | 3/2002 | Ghai et al. |
| 2002/0076452 A1 | 6/2002 | Babish et al. |
| 2002/0077299 A1 | 6/2002 | Babish et al. |
| 2002/0086062 A1 | 7/2002 | Kuhrts |
| 2002/0086070 A1 | 7/2002 | Kuhrts |
| 2002/0156087 A1 | 10/2002 | Nuss et al. |
| 2003/0003212 A1 | 1/2003 | Chien et al. |
| 2003/0008021 A1 | 1/2003 | Babish et al. |
| 2003/0035851 A1 | 2/2003 | Chen |
| 2003/0077313 A1 | 4/2003 | Schwartz et al. |
| 2003/0077798 A1 | 4/2003 | Harrison et al. |
| 2003/0096027 A1 | 5/2003 | Babish et al. |
| 2003/0113393 A1 | 6/2003 | Babish et al. |
| 2003/0133958 A1 | 7/2003 | Kuno et al. |
| 2003/0170219 A1 * | 9/2003 | Bandman et al. ............. 424/94.1 |
| 2003/0180402 A1 | 9/2003 | Jia et al. |
| 2003/0228369 A1 | 12/2003 | Kuhrts |
| 2004/0072900 A1 | 4/2004 | Artman et al. |
| 2004/0086580 A1 | 5/2004 | Tripp et al. |
| 2004/0115290 A1 | 6/2004 | Tripp et al. |
| 2004/0137096 A1 | 7/2004 | Kuhrts |
| 2004/0138199 A1 * | 7/2004 | Gogliotti et al. ......... 514/211.09 |
| 2004/0151792 A1 * | 8/2004 | Tripp et al. .................. 424/745 |
| 2004/0219240 A1 | 11/2004 | Babish et al. |
| 2005/0042317 A1 | 2/2005 | Babish et al. |
| 2005/0129791 A1 | 6/2005 | Babish et al. |
| 2005/0191375 A1 | 9/2005 | Babish et al. |
| 2005/0192356 A1 | 9/2005 | Babish et al. |
| 2006/0074052 A1 | 4/2006 | Eliaz |
| 2006/0127505 A1 | 6/2006 | Haines et al. |
| 2006/0127511 A1 | 6/2006 | Tripp et al. |
| 2006/0127512 A1 | 6/2006 | Tripp et al. |
| 2006/0127513 A1 | 6/2006 | Tripp et al. |
| 2006/0127514 A1 | 6/2006 | Tripp et al. |
| 2006/0127515 A1 | 6/2006 | Tripp et al. |
| 2006/0127516 A1 | 6/2006 | Tripp et al. |
| 2006/0127517 A1 | 6/2006 | Tripp et al. |
| 2006/0193933 A1 | 8/2006 | Tripp et al. |
| 2006/0233902 A1 | 10/2006 | Yajima et al. |
| 2007/0003646 A1 | 1/2007 | Kuhrts |
| 2007/0020352 A1 | 1/2007 | Tripp et al. |
| 2007/0065456 A1 | 3/2007 | Woods |
| 2007/0154576 A1 | 7/2007 | Tripp et al. |
| 2007/0160692 A1 | 7/2007 | Tripp et al. |
| 2007/0166418 A1 | 7/2007 | Tripp et al. |
| 2007/0172532 A1 | 7/2007 | Babish et al. |
| 2007/0184133 A1 | 8/2007 | Tripp et al. |
| 2008/0127720 A1 | 6/2008 | Pauli et al. |
| 2008/0248131 A1 | 10/2008 | Tripp et al. |

FOREIGN PATENT DOCUMENTS

| | | |
|---|---|---|
| DE | 2212148 | 9/1972 |
| DE | 3931147 | 3/1991 |
| DE | 19841615 | 3/2000 |
| EP | 0229022 | 7/1987 |
| EP | 0606599 A1 | 7/1994 |
| EP | 0681029 A2 | 11/1995 |
| EP | 1481671 | 12/2004 |
| EP | 1543834 | 6/2005 |
| EP | 1 938 828 | 7/2008 |
| GB | 2330076 | 4/1999 |
| JP | 52145509 | 12/1977 |
| JP | 58009084 | 2/1983 |
| JP | 59059623 | 4/1984 |
| JP | 363211219 | 9/1988 |
| JP | 04202138 | 7/1992 |
| JP | 6312924 | 11/1994 |
| JP | 07165583 | 6/1995 |
| JP | 07194351 | 8/1995 |
| JP | 08073369 | 3/1996 |
| JP | 8073369 | 3/1996 |
| JP | 9067245 | 3/1997 |
| JP | 09502202 | 3/1997 |
| JP | 410025247 | 1/1998 |
| JP | 10152428 | 6/1998 |
| JP | 10179129 | 7/1998 |
| JP | 11246399 | 9/1999 |
| JP | 11513037 | 11/1999 |
| JP | 11335231 | 12/1999 |
| JP | 2001161338 | 6/2001 |
| JP | 2002-12550 | 1/2002 |
| JP | 2002-505296 | 2/2002 |
| RU | 2045955 | 10/1995 |
| SU | 1247011 | 7/1986 |
| WO | WO 9507079 | 3/1995 |
| WO | WO 97/31630 | 9/1997 |
| WO | WO 9749405 | 12/1997 |
| WO | WO 99/44623 | 9/1999 |
| WO | WO99/44623 | 9/1999 |
| WO | WO 99/61038 | 12/1999 |
| WO | WO 00/68356 | 11/2000 |
| WO | WO00/74696 | 12/2000 |
| WO | WO 00/74696 | 12/2000 |
| WO | WO02/02582 | 1/2002 |
| WO | WO 02/02582 | 1/2002 |
| WO | WO 02/32234 | 4/2002 |
| WO | WO 03/000185 | 1/2003 |
| WO | WO 03/035007 | 5/2003 |
| WO | WO 03/068205 | 8/2003 |
| WO | WO 03/075943 | 9/2003 |
| WO | WO 03/082249 | 10/2003 |
| WO | WO 03/082249 A1 | 10/2003 |
| WO | W02004037180 | 5/2004 |
| WO | WO 2004/037180 | 5/2004 |
| WO | WO 2004/062611 | 7/2004 |
| WO | WO 2005/039483 | 5/2005 |
| WO | WO 2005/084230 | 9/2005 |
| WO | WO 2006/053249 | 5/2006 |
| WO | WO 2006/062681 | 6/2006 |
| WO | WO 2007/021694 | 2/2007 |
| WO | WO 2007/067812 | 6/2007 |
| ZA | 200000857 | 8/2001 |

OTHER PUBLICATIONS

Yang et al, Long-term metformin treatment stimulates cardiomyocyte glucose transport through an AMP-activated protein kinase-dependent reduction in GLUT4 endocytosis, Endocrinology, (Jun. 2006) vol. 147, No. 6, pp. 2728-2736.*

Gao et al, Hypoglycemic properties of polysaccharides extracted from *Ganoderma lucidum* in alloxan-induced diabetic rats, Journal of Food Science and Nutrition (2004), 9(3), 240-244.*

Jafri et al, Effect of Momordica charantia (Karela) in alloxan induced diabetic rats, Pakistan Journal of Science, (2009) vol. 61, No. 4, pp. 220-222.*

Wassel et al, Phytochemical examination and biological studies of *Acacia nilotica* L. Willd and *Acacia farnesiana* L. Willd growing in Egypt, Egyptian Journal of Pharmaceutical Sciences, (1992) vol. 33, No. 1-2, pp. 327-340.*

Arner, P., Insulin Resistance in Type 2 Diabetes—Role of the Adipokines. Curr. Mol. Med.; 5(3):333-339, (May 2005).

Berenbaum, M.C., What is Synergy?: Pharmacol Rev; 41(2):93-141 (1989).

Boden, G., Role of Fatty Acids in the Pathogenesis of Insulin Resistance and NIDDM. Diabetes 46(1): 3-10, (1997).

Cho et al., Akt1/PKBa is Required for Normal Growth but Dispensable for Maintenance Glucose Homeostasis in Mice, J Biol Chem 276:38349-38352 (2001).

Cho et al., Insulin Resistance and a Diabetes Mellitus-Like Syndrome in Mice Lacking the Protein Kinase Akt2 (PKBβ), Science 292:1728-1731 (2001).

Chou, T.C., et al., Quantitative Analysis of Dose-effect Relationships; The Combined Effects of Multiple Drugs or Enzyme Inhibitors; Adv Enzyme Regul 22:27-55, (1984).
Choy, et al., Cytokine Pathways and Joint Inflammation in Rheumatoid Arthritis; New England Jour. Med. 344:pp. 907-916, (2001).
Crowley, et al., A Critical Role for Syk in Signal Transduction and Phagocytosis Mediated by Fcγ Receptors on Macrophages; J. Exp. Med. 186:1027-1039, (1997).
Dignam, et al., Accurate Transcription Initiation by RNA Polymerase II in a Soluble Extract From Isolated Mammalian Nuclei; Nucl Acids Res 11:1475-1489, (1983).
Fasshauer, M., et al., Hormonal Regulation of Adiponectin Gene Expression in 3T3-L1 Adipocytes; Biochem Biophys Res Commun, 290:1084-1089, (2002).
Hibi, M., et al., IL-6 Cytokine Family and Signal Transduction: A Model of the Cytokine System. J Mol Med. 74(1):1-12, (Jan. 1996).
Hofstee, B.H., Non-inverted Versus Inverted Plots in Enzyme Kinetics; Nature 184:1296-1298, (1959).
Hutchcroft, J. E., et al., Association of the 72-kDa Protein-tyrosine Kinase Ptk72 with the B-cell Antigen Receptor; J. Biol. Chem. 267:8613-8619, (1992).
Jiang, K., et al., Regulation of Akt-dependent Cell Survival by Syk and Rac; Blood 101, pp. 236-244, (2003).
Kasturi, R., et al., Hormonal Regulation of Stearoyl Coenzyme a Desaturase Activity and Lipogenesis During Adipose Conversion of 3T3-L1 Cells; J Biol Chem, 257:12224-12230, 1982.
Li, Y., et al., Differential Gene Regulation by PPARgamma Agonist and Constitutively Active PPARgamma2; Mol. Endocrinol., 16:1040-1048, (2002).
Martin, G., et al. PPARgamma Activators Improve Glucose Homeostasis by Stimulating Fatty Acid Uptake in the Adipocytes; Atherosclerosis 137 Suppl:S75-S80, (1998).
Moon KD, et al., Molecular Basis for a Direct Interaction between the Syk Protein-tyrosine Kinase and Phosphoinositide 3-Kinase; J. Biol. Chem. 280, No. 2, Issue of Jan. 14, pp. 1543-1551, (2005).
Oakes, N. D., et al., Thiazolidinediones Increase Plasma-Adipose Tissue FFA Exchange Capacity and Enhance Insulin-Mediated Control of Systemic FFA Availability; Diabetes 50(5):1158-1165, (2001).
Parker, P. J., et al., Glycogen Synthase from Rabbit Skeletal Muscle; Effect of Insulin on the State of Phosphorylation of the Seven Phosphoserine Residues in vivo; (1983) *Eur. J. Biochem.* 130:227-234.
Raeder, E. M., et al., Syk Activation Initiates Downstream Signaling Events During Human Polymorphonuclear Leukocyte Phagocytosis, J. Immunol. 163: 6785-6793, (1999).
Raz, I, et al.; Diabetes: insulin resistance and derangements in lipid metabolism. Cure Through intervention in fat transport and storage; Diabetes Metab. Res. Rev.; 21: 3-14 (2005).
Stumvoll, M., et al., Glitazones: clinical effects and molecular mechanisms. Ann Med 34(3): 217-224, (2002).
van der Kraan P.M., et al., Anabolic and destructive mediators in osteoarthritis. Curr Opin Clin Nutr Metab Care,3:205-211, 2000.
Verdu et al., Cell-autonomous regulation of cell and organ growth in Drospholia by Akt/PKB; Nat cell Biol 1:500-505 (1999).
Ward, S.G., et al., Isoform-specific phosphoinositide 3-kinase inhibitors as therapeutic agents. Curr Opin Pharmacol. Aug. ;3(4):426-434, (2003).
Warner, T.D. et al. Nonsteroidal drug selectivities for cyclo-oxygenase-1 rather than cyclo-oxygenase-2 are associated with human gastrointestinal toxicity: A full in vitro analysis. *Proc. Natl. Acad. Sci. USA* 96:7563-7568, (1999).
Wong B.R., et al., Targeting Syk as a treatment for allergic and autoimmune disorders. Expert Opin Investig Drugs 13:743-762, 2004.
Yajima, H., et al., Isohumulones, Bitter Acids Derived From Hops, Activate Both Peroxisome Proliferator-Activated Receptor Alpha and Gamma and Reduce Insulin Resistance. J Biol Chem, 279: 33456-33462, (2004).
Yamada, T., et al., Association with B-cell antigen cell antigen receptor with protein-tyrosine kinase-P72(Syk) and activation by engagement of membrane IgM; Eur. J. Biochem. 213: 455-459, (1993).

Yamauchi, T., et al., The mechanisms by Which Both Heterozygous Peroxisome Proliferator-activated Receptor gamma (PPARgamma) Deficiency and PPARgamma Agonist Improve Insulin Resistance; J Biol Chem 276(44): 41245-41254, (2001).
Yang, W. S., et al., Weight Reduction Increases Plasma Levels of an Adipose-Derived Anti-Inflammatory Protein, Adiponectin; J Clin Endocrinol Metab 86(8): 3815-3819, (2001).
"Information on arthrotrimtm product", downloaded from Internet Aug. 30, 2002.
"Information on Zyflamend and Zyflamend PM", downloaded from Internet Aug. 30, 2002.
"Information on Hops and Beer Flavours", downloaded from internet Feb. 15, 2005.
Anto, et al. Pharm. Pharmacol. Comm. 4:103-106 (1998).
Bermejo, et al. Rev. Esp. Enferm. Dig. 95: 621-624 and 625-628 (2003).
Brown, et al. J. Chem. Soc. 545 (1959).
Byrne, et al. J. Chem. Soc. (c):2810 (1971).
Carroccio, et al. Clin. Chem. 49:861-867 (2003).
Carson, j. Am. Chem. Soc. 73:1850-1851 (1951).
Chandra, et al. Indian J. Medical Research 60(1):138-142 (1972).
Charlier, et al. Eur. J. Med. Chem. 38:645-659 (2003).
Chou, et al. Eur. J. Biochem. 115:207-216 (1981).
Chou, et al. Adv enzyme regul 22:27-55 (1984).
Chou, et al. J. Biol. Chem. 252:6438-6442 (1977).
Chou, et al. J. Theor. Biol. 35:285-297 (1972).
Chou, et al. Trends Pharm. Sci. 4:450-454 (1983).
Chou, j. Theor. Biol. 59:253-276 (1976).
Cohen, P., Perspectives, 2002 Nature Publishing Group, vol. 1, pp. 309-315.
Costa, et al. Digest. Liver Dis. 35:642-647 (2003).
Davies, WL. Abstract—Fertiliser, Feeding stuffs and Farm Supplies J. 11:694 (1926).
Ding, et al. Biochem. Biophy. Res. Comm. 261:218-223 (1999).
Friedman, et al. J Cutan Med. Surg. 6(5):449-459 (2002).
Gerhäuser, C., European Journal of Cancer 41 (2005), pp. 1941-1954.
Gilani, A.H., Phytotherapy Research, 13 (1999), pp. 665-669.
Goldstein, et al. Am. J. Gastroenterol. 96:1019-1027 (2001).
Halter, et al. Gut 49:443-453 (2001).
Hamberg, et al. J. Bio. Chem. 246:6713-6721 (1971).
Huang, et al. Cancer Res. 51:813-819 (1991).
International Search Report for PCT/US02/19617.
International Search Report for PCT/US04/16043.
International Search Report for PCT/US06/30920.
Jach, Przegl Dermatol. 65(4):379-382 (1978).
Kaltner, D., Untersuchungen zur Ausbildung des Hopfenaromas and technologische Maβnahmen zur Erzeugung hopfenaromatischer Biere, Technische Universitat Munchen, (Nov. 30, 2000), pp. 1-193, plus Tabs. AH1-AH31. (English Translation of cover page, pp. 1-2, tables on pp. 30, 78, 122, and p. 142.
Kanematsu, et al. J Bone Miner Res 12(11):1789-1796 (1997).
Lopes, Curr. Med Res Opin. 8:145-149 (1982).
Meling, et al. Scand. J. Gastroenterol. 31:339-344 (1996).
Noreen, et al. J. Nat. Prod 61:2-7 (1998).
Pairet, et al. Inflamm. Res 47, Supplement 2s93-s101 (1998).
Panglisch, monafsschrift fuer brauwissen schaft, 1990, 43(1), 4-16.
Pippa, et al. Scand. J. Gastroenterol. Suppl. 167:32-35 (1989).
Plewig, et al. J Invest. Dermatol. 65(6):532-536 (1975).
Poullis, et al. J. Gastroenterol. Hepatol. 18:756-762 (2003).
Provital Group, Rosemary-eco Botany, 2007, 9 pages.
Ringbom, et al. J. Nat Prod 61:1212-1215 (1998).
Røseth, digest. Liver Dis. 35:607-609 (2003).
Schjerven, et al. Br. J. Dermatol. 149:484-491 (2003).
Shah, et al. Gut 48:339-346 (2001).
Shimamura, et al. Biochem. Biophys. Res. Comm. 289:220-224 (2001).
Shureiqi, et al. Cancer res. 61:6307-6312 (2001).
Sivri, fundam. Clinic. Pharmacol. 18:23-31 (2004).
Smith, et al., Natural Foam Stabilizing and Bittering Compounds Derived From Hops, Journal of the American Society of Brewing Chemists, vol. 56, No. 2, 1998, pp. 52-57.
Subbaramaiah, et al. Cancer Res. 60:2399-2404 (2000).

Suh, et al. Cancer Res. 58:717-723 (1988).
Tagashira, et al., Biosci. Biotech. Biochem. 59(4):740-742 (1996).
Thomas m. Newmark and paul schulick, Beyond Aspirin nature's answer to arthritis, cancer & alzheimer's disease, hohm press (2000) release 7; pp. 147-151, 248.
Tibble, et al. Drugs Today 37:85-96 (2001).
Tibble, et al. Gut 45:362-366 (1999).
Tobe, et al. Biosci. Biotech. Biochem 61(1):158-159 (1997).
Vanhoenacker, et al., Analysis of iso-alpha-acids and reduced iso-alpha-acids in beer by direct injection and liquid chromatography with ultraviolet absorbance detection or with mass spectrometry, Journal of Chromatography, vol. 1035, No. 1, (Apr. 30, 2004), pp. 53-61.
Warner, et al. Proc Natl Acad Sci USA 96:7563-7568 (1999).
Yamamoto, et al. Abstract—Prostaglandins & Other Lipid Mediators 59:1-235 (1999).
Yamamoto, FEBS Letters 465:103-106 (2000).
Yui, et al. Biol. Pharm. Bull. 26:753-760 (2003).
Supplementary Partial European Search Report for EP Application No. 05723895.8 (5 pages).
Written Opinion for related PCT Application No. PCT/US06/30920.
Wymann, et al. Phosphoinositide 3-Kinase gamma: a key modulator in inflammation and allergy, Biochemical Society Transactions, (Feb. 2003), vol. 31, No. Pt 1, pp. 275-280, Ref: 54.
Dafallah, et al., Investigation of the anti-inflammatory activity of *Acacia nilotica* and *Hibiscus sabdariffa*, The American Journal of Chinese Medicine (1996), vol. 24, No. 3-4, pp. 263-269.
Ei Sissi, et al., Local plants as potential sources of tannins: n. *Acacia nilotica*, Qualitas Plant Mater Vegetabiles (1965), vol. 12, No. 4, pp. 390-396.
Gerhauser, et al., "Cancer Chemopreventive Acitivity of Xanthohumol, a Natural Product Derived from Hop," American Association of Cancer Research, vol. 1, No. 11, Sep. 2002, pp. 959-969.
Vahoecke, et al., "A Safety Study of Oral Tangeretin and Xanthohumol Administration to Laboratory Mice," In Vivo, vol. 19, No. 1, Jan. 2005, pp. 103-107.
Extended European Search Report from related European Application No. 06789591.2, dated Aug. 17, 2009.
Abel-salam et al., Pharmacological Research, England 47(4), pp. 311-340 (Apr. 2003).
Albal, MV., et al., "Clinical evaluation of berberine in mycotic infections." Indian J. Ophthalmol 34:91-2 (1986).
Anto, et al., "Anti-inflammatory Activity of Natural and Synthetic Curcuminoids", Pharmacy and Pharmacology Communications, 4(2), pp. 103-106 (1998).
Baldermann et al., J. Chromatography A 1192(1):191-3 (May 23, 2008) (Epub Apr. 8, 2008); abstract only (1 page).
Bermejo, et al. Rev. Esp. Enferm. Dig. 95(9): 621-624 and 625-628 (2003).
Bolick D et al., Endocrinology 144(12), pp. 5227-5231 (Dec. 2003).
Buhler et al., Antioxidant Activities of Flavanoids, 3 pages, Nov. 2000.
Carroccio, et al. Clin. Chem. 49(6):861-867 (2003).
Chattopadhyay et al., Current Science, 87(1) (Jul. 10, 2004).
Chen Wei-Jen et al., Journal of Agricultural and Food Chemistry 52(1), pp. 55-64 (Jan. 1, 2004).
Chou et al. Eur. J. Biochem. 115:207-216 (1981).
Chou, et al. Adv enzyme regul 22:27-55 (1983).
Chou, et al. J. Biol. Chem. 252(18):6438-6442 (1977).
Chou, et al., TIPS, pp. 450-454, Nov. 1983.
Cohen, Protein Kinases—the major drug targets of the twenty-first century? Nature Reviews, I: 309-315 (2002).
De Keukeleire "Fundamentals of Beer and Hop Chemistry" Quimica Nova, 23(1) pp. 108-112 (2000).
European Examination Report for EP App. No. 02748188.6-1216.
European Search Report for EP App. No. 07809709.4.
European Search Report EP 05 723 839.6.
European Search Report EP 10006768.
European Search Report EP 10011254.
European Search Report EP 10013109.
European Search Report EP 10162893.

European Search Report for corresponding EP Application No. 02737562.5 (4 pages).
European Search Report for related European Application No. 02784313.5.
Exercise as Treatment for Arthritis, Rheumatic and Immunologic Diseases, Cleveland Clinic, www.clevelandclinic.org, Mar. 14, 2000.
Extended European Search Report EP 10162893.1.
Extended European Search Report EP 07717798.8.
Extended European Search Report EP 07809708.6.
Foucault et al., J. Chromatography A 808(1-2):3-22 (May 29, 1998); abstract only (3 pages).
Gao et al., J. Food Sci. Nutr. vol. 9, pp. 240-244 (2004).
Gerhauser et al., Molecular Cancer Therapeutics vol. 1, No. 11, pp. 959-969 (2002).
Gerhauser, Beer Constituents as Potential Cancer Chemopreventive Agents, EP Journal of Cancer 41; 1941-1954: (2005).
Germany, "The Absolutely German Drink," contents of beer, 2004, 5 pages.
Gilani, "Studies on Antihypertensive and Antispasmodic Activities of Methanol Extract of *Acacia nilotica* Pods", Phytotherapy Research 13: 665-669 (1999).
Goldstein, et al. Am. J. Gastroenterol. 96(4):1019-1027 (2001).
Hamberg, et al. J. Bio. Chem. 246(22):6713-6721 (1971).
Hariddradilepah 01, TKDL, Aug. 1, 1999, XP003024376, (3 pages).
Information on ArthroTrim™ product, downloaded from Internet Aug. 30, 2002.
Information on "Hops and Beer Flavours", IOB Technical Symposium, Apr. 2001, pp. 1-9.
Information on "Zyflamend and Zyflamend PM", downloaded from Internet Aug. 30, 2002.
International Search Report for Corresponding PCT Application No. PCT/US05/41018; 2pp.
International Search Report for PCT /US06/30920, Aug. 3, 2007, 3 pages.
International Search Report for PCT/US06/47196.
Jach, Przegl Dermatol. 65(4):379-381 (1978).
Jafri et al., Pakistan Journal of Science, vol. 61, No. 4, pp. 220-222 (Dec. 2009).
Kaltner, Investigation of formation of Hops Aroma and technological Measures for Products of Hops-Aromatic Beers, Technical University of Munich, 7 pp. corresponding to Kaltner, D., Technische Universitat Munchen, (Nov. 30, 2000), pp. 1-193, plus Tabs. AH1-A.
Konda, et al., Arthritis & Rheumatism 62(6): 1683-1692, (2010).
Kuo et al., Cancer Letter, 203:127-137 (2004).
Lamy Virginie et al., Apoptosis, an Int'l Journal on Programmed Cell Death,l3(10), pp. 1232-1242 (Aug. 25, 2008).
Lamy Virginie et al., Carcinogenesis, 28(7), pp. 1575-1581 (Jul. 2007).
Lerman et al, FASEB Journal, Fed. of American Soc. For Experimental Biol., vol. 18, No. 4-5 ( Jan. 1, 2004).
Lopes, Curr. Med Res Opin. 8(3):145-149 (1982).
Lukaczer et al., Phytotherapy Research, vol. 19, No. 10, pp. 864-869 (2005).
Mannering et al., Food, Nutrition and Chemical Toxicity X(X), pp. 311-323 (Jan. 1, 1993).
Minich et al., Journal of nutrition and Metabolism, vol. 2010, article ID 467316, pp. 1-11, (2010).
Murvadyaghrtam, TKDL, Jan. 1, 2001, XP003024377 (4 pages).
Murvadyaghrtam, TKDL, Jan. 1, 1990, XP003024379 (4 pages).
Newark, et al., "Beyond Aspirin", pp. 147-151, Hohm Press (2000).
Office Action issued for U.S. Appl. No. 11/667,614 mailed Apr. 16, 2010.
Office Action issued for U.S. Appl. No. 11/667,615 mailed Mar. 16, 2010.
Office Action issued for U.S. Appl. No. 11/701,583 mailed Feb. 8, 2008.
Office Action issued for U.S. Appl. No. 11/701,583 mailed Jul. 6, 2009.
Office Action issued for U.S. Appl. No. 11/701,583 mailed Nov. 26, 2008.
Office Action issued in U.S. Appl. No. 10/464,834 on Aug. 3, 2010.
Office Action issued in U.S. Appl. No. 10/532,388 on Mar. 26, 2010.
Office Action issued in U.S. Appl. No. 10/532,388 on Jun. 28, 2011.

Office Action issued in U.S. Appl. No. 10/590,301 on Aug. 19, 2010.
Office Action issued in U.S. Appl. No. 10/590,424 on Jun. 29, 2010.
Office Action issued in U.S. Appl. No. 10/789,814 on Jun. 11, 2010.
Office Action issued in U.S. Appl. No. 10/789,814 on Mar. 18, 2011.
Office Action issued in U.S. Appl. No. 11/344,555 on Jan. 19, 2011.
Office Action issued in U.S. Appl. No. 11/344,556 on Sep. 3, 2010.
Office Action issued in U.S. Appl. No. 11/344,556 on Dec. 16, 2009.
Office Action issued in U.S. Appl. No. 11/344,556 on Mar. 27, 2009.
Office Action issued in U.S. Appl. No. 11/344,557 on Mar. 25, 2010.
Office Action issued in U.S. Appl. No. 11/344,557 on Apr. 21, 2008.
Office Action issued in U.S. Appl. No. 11/344,557 on Aug. 28, 2009.
Office Action issued in U.S. Appl. No. 11/344,557 on Jan. 10, 2007.
Office Action issued in U.S. Appl. No. 11/344,557 on Sep. 26, 2007.
Office Action issued in U.S. Appl. No. 11/636,867 on Aug. 30, 2010.
Office Action issued in U.S. Appl. No. 11/636,867 on Mar. 8, 2011.
Office Action issued in U.S. Appl. No. 11/649,584 on Mar. 3, 2010.
Office Action issued in U.S. Appl. No. 11/344,552 on Sep. 8, 2010.
Office Action issued in U.S. Appl. No. 11/501,393 on Aug. 25, 2010.
Office Action issued in U.S. Appl. No. 11/729,696 on Nov. 1, 2010.
Office Action issued in U.S. Appl. No. 11/820,600 on Sep. 30, 2010.
Office Action issued in U.S. Appl. No. 11/820,607 on Oct. 12, 2010.
Office Action issued in U.S. Appl. No. 12/030,335 on Oct. 21, 2010.
Office Action issued in U.S. Appl. No. 12/048,613 on Dec. 8, 2010.
Office Action issued in U.S. Appl. No. 12/754,820 on Mar. 15, 2011.
Office Action issued in U.S. Appl. No. 12/626,392 on Oct. 27, 2010.
Office Action issued in U.S. Appl. No. 11/729,696 on Mar. 25, 2010.
Office Action issued in U.S. Appl. No. 11/729,696 on Jul. 14, 2011.
Office Action issued in U.S. Appl. No. 11/820,755 on Oct. 18, 2010.
Office Action issued in U.S. Appl. No. 11/820,755 on Jun. 1, 2011.
Office Action issued in U.S. Appl. No. 10/464,410 on May 23, 2011.
Office Action issued in U.S. Appl. No. 11/820,607 on May 23, 2011.
Office Action issued in U.S. Appl. No. 11/820,653 on Aug. 8, 2011.
Office Action issued in U.S. Appl. No. 11/820,600 on May 26, 2011.
Office Action issued in U.S. Appl. No. 10/532,388 on Oct. 1, 2010.
Office Action issued in U.S. Appl. No. 11/501,393 on Nov. 9, 2011.
Office Action issued in U.S. Appl. No. 11/636,867 on Oct. 28, 2011.
Office Action issued in U.S. Appl. No. 12/626,392 on Jul. 8, 2011.
Office Action issued in U.S. Appl. No. 12/331,887 on Oct. 12, 2011.
Office Action issued in U.S. Appl. No. 12/754,820 on Nov. 30, 2011.
Ohkura et al., Japanese Joural of Pharmacognosy, 44(3):171-175, (1990).
Panglisch, Monafsschrift fuer Brauwissen Schaft, 43(1), 4-16 (1990).
Parmar et al., Phytochemistry, vol. 28(2):591-593 (1989).
Parts per Milliion, 1 page, 2004.
Poullis ,et al. J. Gastroenterol. Hepatol. 18:756-762 (2003).
Q & A, (what does ppm or ppb mean?) 3 pages, 2004.

Rahman, M.M., et al., "Conjugated linoleic acid inhibits osteoclast differentiation of RAW264.7 cells by modulating RANKL signaling" J. Lipid Res., 47(8): 1739-1748, (2006).
Schmalreck et al, Canadian Journal of Microbiology, vol. 21:205-212 (1975).
Stephan T E et al., Biochemical Pharmacology, 55(4), pp. 505-514, (Feb. 15, 1998).
Stevens, Xanthohumol and related Prenylflavonoids from Hops and Beer: To Your Good Health, Science Direct, 2pp (2004).
Suh, et al. Cancer Res 58:717-723 (1988).
Supplemental European Search Report for EP 07845228.
Supplementary European Search Report form related EP Application No. 05851567, 8PP.
Supplementary Partial European Search Report for related European Patent Application No. 05723895.8, 5 pages (2007).
Supplementary European Search Report for EP Application No. EP 08729724, 9PP.
Supplementary European Search Report for EP Application No. EP 08859091, 5PP.
Tagashira M et al., Bioscience, Biotechnology, and Biochemistry, 59(4), pp. 740-742 (Apr. 1995).
The national. 3 pages (1999).
Tibble, et al. Drugs Today 37(2):85-96 (2001).
Tiktakaghrtam; TKDL, Jan. 1, 1922, XP003024378 (1922).
Turmeric: The Ayurvedic Spice of Life, published at www.bioponic.com/pdfs/TurmericAyurveda.pdf (2003).
US News and world report re Palliative Care, 10 pages (2008).
Van Montfrans et al. Inflammatory Signal Transduction in Crohn's Disease and Novel Therapeutic Approaches. Science Direct, Jun. 2, 2002, 20 pages. Biochemical Pharmacology, vol. 64, issues 5-6.
Vanhoecke et al., In Vivo, vol. 19, No. 1, pp. 103-107 (2005).
Vanhoenacker, et al., Journal of Chromatography, vol. 1035, No. 1, (Apr. 30, 2004), pp. 53-61.
Verzele, et al. Chemistry and analysis of hop and beer bitter acids, Developments in food science, 27, pp. 44-51, 88-139 (1991).
Verzele and De Keukeleire (eds.) Chemistry and Analysis of Hop and Beer Bitter Acids; Elsevier, Chapters 5, 20 pages (1991).
Verzele and De Keukeleire (eds.) Chemistry and Analysis of Hop and Beer Bitter Acids; Elsevier, Chapters 6, 8 pages (1991).
Wang, et al. Free Radical Biology & Medicine 27:612-616 (1999).
Ward, et al., Therapeutic Potential of Phosphoinositide 3-Kinase Inhibitors, Chemistry & Biology, vol. 10, 207-210, Mar. 2003.
Written Opinion for corresponding PCT Application No. PCT/US05/41018; 3 pp.
Yui, et al. Biol. Pharm. Bull. 26(6):753-760 (2003).
Zhao Feng et al., Biological and Pharmaceutical Bulletin, 26(1), pp. 61-65 (Jan. 2003).

* cited by examiner

A.

B.

Rho Isoalpha acids

Isoalpha acids

Tetrahydroisoalpha acids

Hexahydroisoalpha acids

Xanthohumol

Spent Hops

Hexahydrocolupulone

Troglitazone

PROTEIN KINASE MODULATION BY HOPS AND *ACACIA* PRODUCTS

CROSS-REFERENCE TO RELATED APPLICATIONS

This patent application claims priority to U.S. provisional application Ser. No. 60/706,984 filed on Aug. 9, 2005, and Ser. No. 60/748,931 filed on Dec. 9, 2005.

BACKGROUND OF THE INVENTION

1. Field of the Invention

The present invention relates generally to methods and compositions that can be used to treat or inhibit pathological conditions associated with tissue-specific activation of protein kinase activity and/or inflammation, to methods of modulating protein kinase activity in cells and to methods of modulating inflammation. More specifically, the invention relates to methods and compositions which utilize extracts, derivatives or fractions isolated either from hops or from members of the plant genus *Acacia*, or combinations thereof.

2. Description of the Related Art

Signal transduction provides an overarching regulatory mechanism important to maintaining normal homeostasis or, if perturbed, acting as a causative or contributing mechanism associated with numerous disease pathologies and conditions. At the cellular level, signal transduction refers to the movement of a signal or signaling moiety from outside of the cell to the cell interior. The signal, upon reaching its receptor target, may initiate ligand-receptor interactions requisite to many cellular events, some of which may further act as a subsequent signal. Such interactions serve to not only as a series cascade but moreover an intricate interacting network or web of signal events capable of providing fine-tuned control of homeostatic processes. This network however can become dysregulated, thereby resulting in an alteration in cellular activity and changes in the program of genes expressed within the responding cell. See, for example, FIG. 1 which displays a simplified version of the interacting kinase web regulating insulin sensitivity and resistance.

Signal transducing receptors are generally classified into three classes. The first class of receptors are receptors that penetrate the plasma membrane and have some intrinsic enzymatic activity. Representative receptors that have intrinsic enzymatic activities include those that are tyrosine kinases (e.g. PDGF, insulin, EGF and FGF receptors), tyrosine phosphatases (e.g. CD45 [cluster determinant-45] protein of T cells and macrophages), guanylate cyclases (e.g. natriuretic peptide receptors) and serine/threonine kinases (e.g. activin and TGF-β receptors). Receptors with intrinsic tyrosine kinase activity are capable of autophosphorylation as well as phosphorylation of other substrates.

Receptors of the second class are those that are coupled, inside the cell, to GTP-binding and hydrolyzing proteins (termed G-proteins). Receptors of this class which interact with G-proteins have a structure that is characterized by 7 transmembrane spanning domains. These receptors are termed serpentine receptors. Examples of this class are the adrenergic receptors, odorant receptors, and certain hormone receptors (e.g. glucagon, angiotensin, vasopressin and bradykinin).

The third class of receptors may be described as receptors that are found intracellularly and, upon ligand binding, migrate to the nucleus where the ligand-receptor complex directly affects gene transcription.

The proteins which encode for receptor tyrosine kinases (RTK) contain four major domains, those being: a) a transmembrane domain, b) an extracellular ligand binding domain, c) an intracellular regulatory domain, and d) an intracellular tyrosine kinase domain. The amino acid sequences of RTKs are highly conserved with those of cAMP-dependent protein kinase (within the ATP and substrate binding regions). RTK proteins are classified into families based upon structural features in their extracellular portions which include the cysteine rich domains, immunoglobulin-like domains, cadherin domains, leucine-rich domains, Kringle domains, acidic domains, fibronectin type III repeats, discoidin I-like domains, and EGF-like domains. Based upon the presence of these various extracellular domains the RTKs have been subdivided into at least 14 different families.

Many receptors that have intrinsic tyrosine kinase activity upon phosphorylation interact with other proteins of the signaling cascade. These other proteins contain a domain of amino acid sequences that are homologous to a domain first identified in the c-Src proto-oncogene. These domains are termed SH2 domains.

The interactions of SH2 domain containing proteins with RTKs or receptor associated tyrosine kinases leads to tyrosine phosphorylation of the SH2 containing proteins. The resultant phosphorylation produces an alteration (either positively or negatively) in that activity. Several SH2 containing proteins that have intrinsic enzymatic activity include phospholipase C-γ (PLC-γ), the proto-oncogene c-Ras associated GTPase activating protein (rasGAP), phosphatidylinositol-3-kinase (PI-3K), protein tyrosine phosphatase-1C (PTP1C), as well as members of the Src family of protein tyrosine kinases (PTKs).

Non-receptor protein tyrosine kinases (PTK) by and large couple to cellular receptors that lack enzymatic activity themselves. An example of receptor-signaling through protein interaction involves the insulin receptor (IR). This receptor has intrinsic tyrosine kinase activity but does not directly interact, following autophosphorylation, with enzymatically active proteins containing SH2 domains (e.g. PI-3K or PLC-γ). Instead, the principal IR substrate is a protein termed IRS-1.

The receptors for the TGF-β superfamily represent the prototypical receptor serine/threonine kinase (RSTK). Multifunctional proteins of the TGF-β superfamily include the activins, inhibins and the bone morphogenetic proteins (BMPs). These proteins can induce and/or inhibit cellular proliferation or differentiation and regulate migration and adhesion of various cell types. One major effect of TGF-β is a regulation of progression through the cell cycle. Additionally, one nuclear protein involved in the responses of cells to TGF-β is c-Myc, which directly affects the expression of genes harboring Myc-binding elements. PKA, PKC, and MAP kinases represent three major classes of non-receptor serine/threonine kinases.

The relationship between kinase activity and disease states is currently being investigated in many laboratories. Such relationships may be either causative of the disease itself or intimately related to the expression and progression of disease associated symptomology. Rheumatoid arthritis, an autoimmune disease, provides one example where the relationship between kinases and the disease are currently being investigated.

Autoimmune diseases result from a dysfunction of the immune system in which the body produces autoantibodies which attack its own organs, tissues and cells—a process mediated via protein phosphorylation.

Over 80 clinically distinct autoimmune diseases have been identified and collectively afflict approximately 24 million people in the US. Autoimmune diseases can affect any tissue or organ of the body. Because of this variability, they can cause a wide range of symptoms and organ injuries, depending upon the site of autoimmune attack. Although treatments exist for many autoimmune diseases, there are no definitive cures for any of them. Treatments to reduce the severity often have adverse side effects.

Rheumatoid arthritis (RA) is the most prevalent and best studied of the autoimmune diseases and afflicts about 1% of the population worldwide, and for unknown reasons, like other autoimmune diseases, is increasing. RA is characterized by chronic synovial inflammation resulting in progressive bone and cartilage destruction of the joints. Cytokines, chemokines, and prostaglandins are key mediators of inflammation and can be found in abundance both in the joint and blood of patients with active disease. For example, PGE2 is abundantly present in the synovial fluid of RA patients. Increased PGE2 levels are mediated by the induction of cyclooxygenase-2 (COX-2) and inducible nitric oxide synthase (iNOS) at inflamed sites. [See, for example van der Kraan P M and van den Berg W B. Anabolic and destructive mediators in osteoarthritis. Curr Opin Clin Nutr Metab Care, 3:205-211, 2000; Choy E H S and Panayi G S. Cytokine pathways and joint inflammation in rheumatoid arthritis. N Eng J Med. 344:907-916, 2001; and Wong B R, et al. Targeting Syk as a treatment for allergic and autoimmune disorders. Expert Opin Investig Drugs 13:743-762, 2004.]

The etiology and pathogenesis of RA in humans is still poorly understood, but is viewed to progress in three phases. The initiation phase where dendritic cells present self antigens to autoreactive T cells. The T cells activate autoreactive B cells via cytokines resulting in the production of autoantibodies, which in turn form immune complexes in joints. In the effector phase, the immune complexes bind Fcf receptors on macrophages and mast cells, resulting in release of cytokines and chemokines, inflammation and pain. In the final phase, cytokines and chemokines activate and recruit synovial fibroblasts, osteoclasts and polymorphonuclear neutrophils that release proteases, acids, and ROS such as O2-, resulting in irreversible cartilage and bone destruction.

In the collagen-induced RA animal model, the participation of T and B cells is required to initiate the disease. B cell activation signals through spleen tyrosine kinase (Syk) and phosphoinositide 3-kinase (PI3K) following antigen receptor triggering [Ward S G, Finan P. Isoform-specific phosphoinositide 3-kinase inhibitors as therapeutic agents. Curr Opin Pharmacol. August; 3(4):426-34, (2003)]. After the engagement of antigen receptors on B cells, Syk is phosphorylated on three tyrosines. Syk is a 72-kDa protein-tyrosine kinase that plays a central role in coupling immune recognition receptors to multiple downstream signaling pathways. This function is a property of both its catalytic activity and its ability to participate in interactions with effector proteins containing SH2 domains. Phosphorylation of Tyr-317, -342, and -346 create docking sites for multiple SH2 domain containing proteins. [Hutchcroft, J. E., Harrison, M. L. & Geahlen, R. L. (1992). Association of the 72-kDa protein-tyrosine kinase Ptk72 with the B-cell antigen receptor. J. Biol. Chem. 267: 8613-8619, (1992) and Yamada, T., Taniguchi, T., Yang, C., Yasue, S., Saito, H. & Yamamura, H. Association with B-cell antigen cell antigen receptor with protein-tyrosine kinase-P72(Syk) and activation by engagement of membrane IgM. Eur. J. Biochem. 213: 455-459, (1993)].

Syk has been shown to be required for the activation of PI3K in response to a variety of signals including engagement of the B cell antigen receptor (BCR) and macrophage or neutrophil Fc receptors. [See Crowley, M. T., et al,. J. Exp. Med. 186: 1027-1039, (1997); Raeder, E. M., et al., J. Immunol. 163, 6785-6793, (1999); and Jiang, K., et al., Blood 101, 236-244, (2003)]. In B cells, the BCR-stimulated activation of PI3K can be accomplished through the phosphorylation of adaptor proteins such as BCAP, CD19, or Gab1, which creates binding sites for the p85 regulatory subunit of PI3K. Signals transmitted by many IgG receptors require the activities of both Syk and PI3K and their recruitment to the site of the clustered receptor. In neutrophils and monocytes, a direct association of PI3K with phosphorylated immunoreceptor tyrosine based activation motif sequences on FcgRIIA was proposed as a mechanism for the recruitment of PI3K to the receptor. And recently a direct molecular interaction between Syk and PI3K has been reported [Moon K D, et al, Molecular Basis for a Direct Interaction between the Syk Protein-tyrosine Kinase and Phosphoinositide 3-Kinase. J. Biol. Chem. 280, No. 2, Issue of January 14, pp. 1543-1551, (2005)].

Much research has shown that inhibitors of COX-2 activity result in decreased production of PGE2 and are effective in pain relief for patients with chronic arthritic conditions such as RA. However, concern has been raised over the adverse effects of agents that inhibit COX enzyme activity since both COX-1 and COX-2 are involved in important maintenance functions in tissues such as the gastrointestinal and cardiovascular systems. Therefore, designing a safe, long term treatment approach for pain relief in these patients is necessary. Since inducers of COX-2 and iNOS synthesis signal through the Syk, PI3K, p38, ERK½, and NF-kB dependent pathways, inhibitors of these pathways may be therapeutic in autoimmune conditions and in particular in the inflamed and degenerating joints of RA patients.

The hops derivative Rho isoalpha acid (RIAA) was found in a screen for inhibition of PGE2 in a RAW 264.7 mouse macrophages model of inflammation. In the present study, we investigated whether RIAA is a direct COX enzyme inhibitor and/or whether it inhibits the induction of COX-2 and iNOS. Our finding that RIAA does not directly inhibit COX enzyme activity, but instead inhibits NF-kB driven enzyme induction lead us to investigate whether RIAA is a kinase inhibitor. Our finding that RIAA inhibits both Syk and PI3K lead us to test its efficacy in a pilot study in patients suffering from various autoimmune diseases.

Other kinases currently being investigated for their association with disease symptomology include Aurora, FGFB, MSK, RSE, and SYK.

Aurora—Important regulators of cell division, the Aurora family of serine/threonine kinases includes Aurora A, B and C. Aurora A and B kinases have been identified to have direct but distinct roles in mitosis. Over-expression of these three isoforms have been linked to a diverse range of human tumor types, including leukemia, colorectal, breast, prostate, pancreatic, melanoma and cervical cancers.

Fibroblast growth factor receptor (FGFR) is a receptor tyrosine kinase. Mutations in this receptor can result in constitutive activation through receptor dimerization, kinase activation, and increased affinity for FGF. FGFR has been implicated in achondroplasia, angiogenesis, and congenital diseases.

MSK (mitogen- and stress-activated protein kinase) 1 and MSK2 are kinases activated downstream of either the ERK (extracellular-signal-regulated kinase) ½ or p38 MAPK (mitogen-activated protein kinase) pathways in vivo and are required for the phosphorylation of CREB (cAMP response element-binding protein) and histone H3.

Rse is mostly highly expressed in the brain. Rse, also known as Brt, BYK, Dtk, Etk3, Sky, Tif, or sea-related receptor tyrosine kinase, is a receptor tyrosine kinase whose primary role is to protect neurons from apoptosis. Rse, Axl, and Mer belong to a newly identified family of cell adhesion molecule-related receptor tyrosine kinases. GAS6 is a ligand for the tyrosine kinase receptors Rse, Axl, and Mer. GAS6 functions as a physiologic anti-inflammatory agent produced by resting EC and depleted when pro-inflammatory stimuli turn on the pro-adhesive machinery of EC.

Glycogen synthase kinase-3 (GSK-3), present in two isoforms, has been identified as an enzyme involved in the control of glycogen metabolism, and may act as a regulator of cell proliferation and cell death. Unlike many serine-threonine protein kinases, GSK-3 is constitutively active and becomes inhibited in response to insulin or growth factors. Its role in the insulin stimulation of muscle glycogen synthesis makes it an attractive target for therapeutic intervention in diabetes and metabolic syndrome.

GSK-3 dysregulation has been shown to be a focal point in the development of insulin resistance. Inhibition of GSK3 improves insulin resistance not only by an increase of glucose disposal rate but also by inhibition of gluconeogenic genes such as phosphoenolpyruvate carboxykinase and glucose-6-phosphatase in hepatocytes. Furthermore, selective GSK3 inhibitors potentiate insulin-dependent activation of glucose transport and utilization in muscle in vitro and in vivo. GSK3 also directly phosphorylates serine/threonine residues of insulin receptor substrate-1, which leads to impairment of insulin signaling. GSK3 plays an important role in the insulin signaling pathway and it phosphorylates and inhibits glycogen synthase in the absence of insulin [Parker, P. J., Caudwell, F. B., and Cohen, P. (1983) *Eur. J. Biochem.* 130:227-234]. Increasing evidence supports a negative role of GSK-3 in the regulation of skeletal muscle glucose transport activity. For example, acute treatment of insulin-resistant rodents with selective GSK-3 inhibitors improves whole-body insulin sensitivity and insulin action on muscle glucose transport. Chronic treatment of insulin-resistant, pre-diabetic obese Zucker rats with a specific GSK-3 inhibitor enhances oral glucose tolerance and whole-body insulin sensitivity, and is associated with an amelioration of dyslipidemia and an improvement in IRS-1-dependent insulin signaling in skeletal muscle. These results provide evidence that selective targeting of GSK-3 in muscle may be an effective intervention for the treatment of obesity-associated insulin resistance.

Syk is a non-receptor tyrosine kinase related to ZAP-70 involved in signaling from the B-cell receptor and the IgE receptor. Syk binds to ITAM motifs within these receptors, and initiates signaling through the Ras, PI 3-kinase, and PLCg signaling pathways. Syk plays a critical role in intracellular signaling and thus is an important target for inflammatory diseases and respiratory disorders.

Therefore, it would be useful to identify methods and compositions that would modulate the expression or activity of single or multiple selected kinases. The realization of the complexity of the relationship and interaction among and between the various protein kinases and kinase pathways reinforces the pressing need for developing pharmaceutical agents capable of acting as protein kinase modulators, regulators or inhibitors that have beneficial activity on multiple kinases or multiple kinase pathways. A single agent approach that specifically targets one kinase or one kinase pathway may be inadequate to treat very complex diseases, conditions and disorders, such as, for example, diabetes and metabolic syndrome. Modulating the activity of multiple kinases may additionally generate synergistic therapeutic effects not obtainable through single kinase modulation.

Such modulation and use may require continual use for chronic conditions or intermittent use, as needed for example in inflammation, either as a condition unto itself or as an integral component of many diseases and conditions. Additionally, compositions that act as modulators of kinase can affect a wide variety of disorders in a mammalian body. The instant invention describes compounds and extracts derived from hops or *Acacia* which may be used to regulate kinase activity, thereby providing a means to treat numerous disease related symptoms with a concomitant increase in the quality of life.

SUMMARY OF THE INVENTION

The present invention relates generally to methods and compositions for modulating disease associated protein kinases in cells or mammals in need. In some instances the mammal in need has a condition selected from the group consisting of autoimmune disorders, allergic or inflammatory disorders (including bone), insulin resistance associated disorders including aging, cardiovascular disease, lipid storage disorders, metabolic syndrome or diabetes associated disorders, cancer, ocular disorders, and neurological disorders. More specifically, the invention relates to methods and compositions comprising extracts, derivatives or fractions isolated either from hops or from members of the plant genus *Acacia*, or combinations thereof. The invention further relates to methods and compositions to inhibit inflammatory mediator compounds such as COX-2 or prostaglandins selectively, or to inhibit inflammatory responses through protein kinase modulation in selected target cells. Additionally described are methods and compositions for the treating symptomology associated with diseases or conditions selected from the group consisting of autoimmune disorders, allergic or inflammatory disorders(including bone), insulin resistance associated disorders including aging, cardiovascular disease, lipid storage disorders, metabolic syndrome or diabetes associated disorders, cancer, ocular disorders, and neurological disorders.

A first embodiment of the invention describes methods for modulating the activity of a plurality of disease associated protein kinases in a subject in need thereof, wherein said protein kinase modulation is beneficial to the health of the subject. In this embodiment the method comprises administering to the subject in need a therapeutically effective amount of a composition comprising a compound selected from the group consisting of alpha acids, beta acids, prenylflavonoids, chalcones, isoalpha acids, reduced isoalpha acids, spent hops, and a compound or extract derived from acacia.

A second embodiment of the invention describes a method for modulating the activity of a plurality of metabolic syndrome associated protein kinases in a subject in need where the protein kinase modulation is beneficial to the health of the subject. This method comprises administering to the subject in need a therapeutically effective amount of a composition comprising a 5:1 ratio of rho-isoalpha acids to *Acacia nilotica* heartwood or bark powder extract.

A further embodiment of the invention describes compositions for modulating the activity of a plurality of disease associated protein kinases in a subject in need thereof, where the protein kinase modulation is beneficial to the health of the subject. In this embodiment the composition comprises a therapeutically effective amount of a composition comprising a compound selected from the group consisting of alpha acids, beta acids, prenylflavonoids, chalcones, isoalpha acids, reduced isoalpha acids, spent hops, and a compound or extract derived from acacia.

Another embodiment of the invention describes a composition for modulating the activity of a plurality of metabolic syndrome associated protein kinases in a subject in need where the protein kinase modulation is beneficial to the health of the subject. This composition comprises a therapeutically effective amount of a composition comprising a 5:1 ratio of rho-isoalpha acids to *Acacia nilotica* heartwood or bark powder extract.

In a further embodiment compositions for modulating the activity of a plurality of ocular disorder associated protein kinases in a subject, wherein said protein kinase modulation is beneficial to the health of the subject are described. Here the compositions comprise a therapeutically effective amount of a composition comprising from about 1 mg to about 1000 mg of vitamin C; from about 1 IU to about 1000 IU of vitamin E; from about 0.1 mg to about 2.5 mg of selenium; from about 1 mg to about 50 mg of zinc; from about 0.1 mg to about 10 mg of copper; from about 1 mg to about 15 mg of lutein; from about 0.05 mg to about 1 mg of zeaxanthin; and from about 1 mg to about 1000 mg of *Acacia nilotica* heartwood powder or bark extract.

Another embodiment of the invention discloses compositions for modulating the activity of a plurality of cancer associated protein kinases in a subject in need where the protein kinase modulation is beneficial to the health of the subject. In this embodiment the composition comprises a therapeutically effective amount of at least one member selected from the group consisting of:

a. from about 0.01 mg to about 10,000 mg of xanthohumol;
b. from about 0.01 mg to about 10,000 mg of tetrahydro isoalpha acid (THIAA);
c. from about 0.01 mg to about 10,000 mg of hexahydro isoalpha acid (HHIAA);
d. from about 0.01 mg to about 10,000 mg of RIAA;
e. from about 0.01 mg to about 10,000 mg of isoalpha acid (IAA);
f. from about 0.01 mg to about 10,000 mg of beta acids; and
g. from about 0.01 mg to about 10,000 mg of alpha acids.

DETAILED DESCRIPTION OF THE INVENTION

Figure 1:
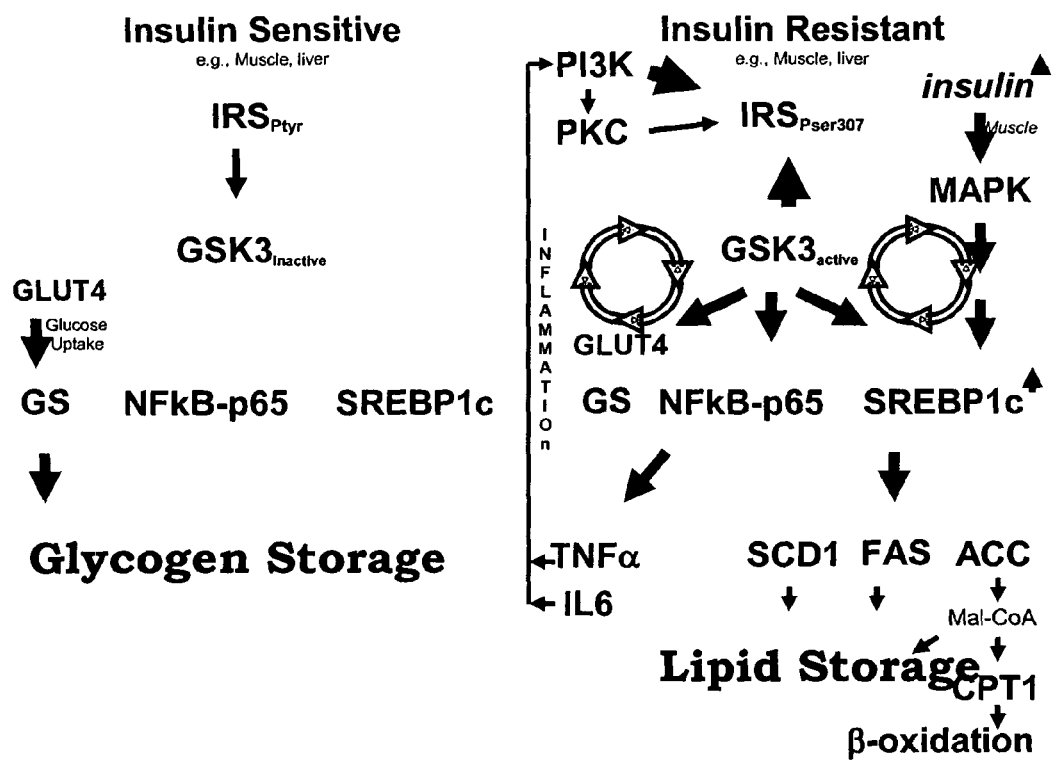
FIG. 1 graphically depicts a portion of the kinase network regulating insulin sensitivity and resistance.

The present invention provides methods and compositions for modulating protein kinases in cells or mammals in need. In some instances the mammal in need has a condition selected from the group consisting of autoimmune disorders, allergic or inflammatory disorders, metabolic syndrome or diabetes associated disorders, cancer, and neurological disorders. More specifically, the invention relates to a compositions, methods and kits comprising extracts, derivatives or fractions isolated either from hops or from members of the plant genus *Acacia*, or combinations thereof. The invention further relates to compositions and methods to inhibit inflammatory mediators such as cyclooxygenase-2 (COX-2) or prostaglandins selectively, or to inhibit inflammatory responses through protein kinase modulation in selected target cells.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 11th Ed., McGraw Hill Companies Inc., New York (2006).

In the specification and the appended claims, the singular forms include plural referents unless the context clearly dictates otherwise. As used in this specification, the singular forms "a," "an" and "the" specifically also encompass the plural forms of the terms to which they refer, unless the content clearly dictates otherwise. Additionally, as used herein, unless specifically indicated otherwise, the word "or" is used in the "inclusive" sense of "and/or" and not the "exclusive" sense of "either/or." The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

A first embodiment of the invention discloses methods for modulating the activity of a plurality of disease associated protein kinases in a subject in need thereof, where the protein kinase modulation is beneficial to the health of the subject. Methods of this embodiment comprise administering to the subject in need a therapeutically effective amount of a composition comprising a compound selected from the group consisting of alpha acids, beta acids, prenylflavonoids, chalcones, isoalpha acids, reduced isoalpha acids, spent hops, and a compound or extract derived from acacia.

In some aspects of this embodiment the subject in need has a condition selected from the group consisting of autoimmune disorders, allergic or inflammatory disorders, metabolic syndrome or diabetes associated disorders, cancer, ocular disorders, and neurological disorders, while in other aspects the disease associated protein kinase is selected from the group consisting of ABL, AKT, AURORA, CDK, DBF2/20, EGFR, EPH/ELK/ECK, ERK/MAPKFGFR, GSK3, IKKB, INSR, JAK DOM ½, MARK/PRKAA, MEK/STE7, MEKK/STE11, MLK, mTOR, PAK/STE20, PDGFR, PI3K, PKC, POLO, SRC, TEC/ATK, and ZAP/SYK.

In still other aspects the alpha acid is selected from the group consisting of humulone, cohumulone, adhumulone, prehumulone, and posthumulone or the beta acid is selected from the group consisting of lupulone, colupulone, adlupulone, and prelupulone.

In yet other aspects the isoalpha acid of the composition used is selected from the group consisting of isohumulone, isoadhumulone, and isocohumulone. While the compositions employ RIAA, the RIAA is selected from the group consisting of dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. The rho-isoalpha acid configuration is employed in yet other aspects of this embodiment.

In some aspects of this embodiment the chalcone is xanthohumol or isoxanthohumol, or the prenylflavonoid is 6-prenylnaringenin or 8-prenylnaringenin.

In yet other aspects, the compound or extract derived from acacia is derived from *Acacia catechu* or *Acacia nilotica*. In those aspects where the acacia derived compound or extract is derived from *Acacia catechu* or *Acacia nilotica*, the *Acacia catechu* or *Acacia nilotica* compound is selected from the group consisting of gum resin, bark powder, heartwood powder, and an *Acacia catechu* or *Acacia nilotica* extract. In those aspects where the acacia derived compound is an *Acacia catechu* or *Acacia nilotica* extract, the extract is selected from acidic, alkaline, polar solvent, nonpolar solvent, and gastric fluid extracts.

Compositions used in the methods of this embodiment may further comprise one or more members selected from the group consisting of antioxidants, vitamins, minerals, proteins, fats, and carbohydrates, or a pharmaceutically acceptable excipient selected from the group consisting of coatings, isotonic and absorption delaying agents, binders, adhesives, lubricants, disintergrants, coloring agents, flavoring agents, sweetening agents, absorbants, detergents, and emulsifying agents.

In some methods of this embodiment, the composition used further comprises an antidiabetic drug selected from the group consisting of rosiglitazone, troglitazone, pioglitazone, and metformin.

As used herein, "disease associated kinase" means those individual protein kinases or groups or families of kinases that are either directly causative of the disease or whose activation is associated with pathways which serve to exacerbate the symptoms of the disease in question. Furthermore, as used herein "disease", "condition", or "disorder" may be used interchangeably.

The phrase "protein kinase modulation is beneficial to the health of the subject" refers to those instances wherein the kinase modulation (either up or down regulation) results in reducing, preventing, and/or reversing the symptoms of the disease or augments the activity of a secondary treatment modality.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or compounds, but may also include additional features or compounds.

As used herein, the terms "derivatives" or a matter "derived" refer to a chemical substance related structurally to another substance and theoretically obtainable from it, i.e. a substance that can be made from another substance. Derivatives can include compounds obtained via a chemical reaction.

As used herein, the term "hop extract" refers to the solid material resulting from (1) exposing a hops plant product to a solvent, (2) separating the solvent from the hops plant products, and (3) eliminating the solvent. "Spent hops" refers to the hops plant products remaining following a hops extraction procedure. See Verzele, M. and De Keukeleire, D., *Developments in Food Science 27: Chemistry and Analysis of Hop and Beer Bitter Acids*, Elsevier Science Pub. Co., 1991, New York, USA, herein incorporated by reference in its entirety, for a detailed discussion of hops chemistry. As used herein when in reference to a RIAA, "Rho" refers to those reduced isoalpha acids wherein the reduction is a reduction of the carbonyl group in the 4-methyl-3-pentenoyl side chain.

As used herein, the term "solvent" refers to a liquid of aqueous or organic nature possessing the necessary characteristics to extract solid material from the hop plant product. Examples of solvents would include, but not limited to, water, steam, superheated water, methanol, ethanol, hexane, chloroform, liquid $CO_2$, liquid $N_2$ or any combinations of such materials.

As used herein, the term "$CO_2$ extract" refers to the solid material resulting from exposing a hops plant product to a liquid or supercritical $CO_2$ preparation followed by subsequent removal of the $CO_2$.

The term "pharmaceutically acceptable" is used in the sense of being compatible with the other ingredients of the compositions and not deleterious to the recipient thereof.

As used herein, "compounds" may be identified either by their chemical structure, chemical name, or common name. When the chemical structure and chemical or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, unless otherwise indicated, all physical forms are equivalent for the uses contemplated herein and are intended to be within the scope of the present invention.

Compounds according to the invention may be present as salts. In particular, pharmaceutically acceptable salts of the compounds are contemplated. A "pharmaceutically acceptable salt" of the invention is a combination of a compound of the invention and either an acid or a base that forms a salt (such as, for example, the magnesium salt, denoted herein as "Mg" or "Mag") with the compound and is tolerated by a subject under therapeutic conditions. In general, a pharmaceutically acceptable salt of a compound of the invention will have a therapeutic index (the ratio of the lowest toxic dose to the lowest therapeutically effective dose) of 1 or greater. The person skilled in the art will recognize that the lowest therapeutically effective dose will vary from subject to subject and from indication to indication, and will thus adjust accordingly.

As used herein "hop" or "hops" refers to plant cones of the genus *Humulus* which contain a bitter aromatic oil which is used in the brewing industry to prevent bacterial action and add the characteristic bitter taste to beer. More preferably, the hops used are derived from *Humulus lupulus*.

The term "acacia", as used herein, refers to any member of leguminous trees and shrubs of the genus *Acacia*. Preferably, the botanical compound derived from acacia is derived from *Acacia catechu* or *Acacia nilotica*.

The compounds according to the invention are optionally formulated in a pharmaceutically acceptable vehicle with any of the well known pharmaceutically acceptable carriers, including diluents and excipients (see Remington's Pharmaceutical Sciences, 18th Ed., Gennaro, Mack Publishing Co., Easton, Pa. 1990 and Remington: The Science and Practice of Pharmacy, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention), as well any other pharmacologically active ingredient useful for the treatment of the symptom/condition being treated.

In some aspects of this embodiment, the modulated kinase is selected from the group consisting of Abl, Abl(T3151), ALK, ALK4, AMPK, Arg, Arg, ARK5, ASK1, Aurora-A, Axl, Blk, Bmx, BRK, BrSK1, BrSK2, BTK, CaMKI, CaMKII, CaMKIV, CDK1/cyclinB, CDK2/cyclinA, CDK2/cyclinE, CDK3/cyclinE, CDK5/p25, CDK5/p35, CDK6/cyclinD3, CDK7/cyclinH/MAT1, CDK9/cyclin T1, CHK1, CHK2, CK1(y), CK1δ, CK2, CK2α2, cKit(D816V), cKit, c-RAF, CSK, cSRC, DAPK1, DAPK2, DDR2, DMPK, DRAK1, DYRK2, EGFR, EGFR(L858R), EGFR(L861Q), EphA1, EphA2, EphA3, EphA4, EphA5, EphA7, EphA8, EphB1, EphB2, EphB3, EphB4, ErbB4, Fer, Fes, FGFR1, FGFR2, FGFR3, FGFR4, Fgr, Flt1, Flt3(D835Y), Flt3, Flt4, Fms, Fyn, GSK3β, GSK3α, Hck, HIPK1, HIPK2, HIPK3, IGF-1R, IKKβ, IKKα, IR, IRAK1, IRAK4, IRR, ITK, JAK2, JAK3, JNK1α1, JNK2α2, JNK3, KDR, Lck, LIMK1, LKB1, LOK, Lyn, Lyn, MAPK1, MAPK2, MAPK2, MAPKAP-K2, MAPKAP-K3, MARK1, MEK1, MELK, Met, MINK, MKK4, MKK6, MKK7β, MLCK, MLK1, Mnk2, MRCKβ, MRCKα, MSK1, MSK2, MSSK1, MST1, MST2, MST3, MuSK, NEK2, NEK3, NEK6, NEK7, NLK, p70S6K, PAK2, PAK3, PAK4, PAK6, PAR-1Bα, PDGFRβ, PDGFRα, PDK1, PI3K beta, PI3K delta, PI3K gamma, Pim-1, Pim-2, PKA(b), PKA, PKBβ, PKBα, PKBγ, PKCμ, PKCβI, PKCβII, PKCα, PKCγ, PKCδ, PKCε, PKCζ, PKCη, PKCθ, PKCι, PKD2, PKG1β, PKG1α, Plk3, PRAK, PRK2, PrKX, PTK5, Pyk2, Ret, RIPK2, ROCK-I, ROCK-II, ROCK-II, Ron, Ros, Rse, Rsk1, Rsk1, Rsk2, Rsk3, SAPK2a, SAPK2a(T106M), SAPK2b, SAPK3, SAPK4, SGK, SGK2, SGK3, SIK, Snk, SRPK1, SRPK2, STK33, Syk, TAK1, TBK1, Tie2, TrkA, TrkB, TSSK1, TSSK2, WNK2, WNK3, Yes, ZAP-70, and ZIPK.

In preferred aspects the modulated kinase is selected from the group consisting of Aurora-A, CDK2/cyclin A, DAPK1, DAPK2, EphA3FGFR4, GSK3β, GSK3α, Hck, MAPK1, MAPKAP-K2, MSK2, MSSK1, PI3K beta, PI3K delta, PI3K gamma, Rse, Rsk2, Syk, and Tie2. In more preferred aspects the modulated kinase is selected from the group consisting of ABL, AKT, AURORA, CDK, DBF2/20, EGFR, EPH/ELK/ECK, ERK/MAPKFGFR, GSK3, IKKB, INSR, JAK DOM ½, MARK/PRKAA, MEK/STE7, MEKK/STE11, MLK, mTOR, PAK/STE20, PDGFR, PI3K, PKC, POLO, SRC, TEC/ATK, and ZAP/SYK.

In some aspects, the mammal in need has a condition selected from the group consisting of autoimmune disorders, allergic or inflammatory disorders, metabolic syndrome or diabetes associated disorders, cancer, ocular disorders, and neurological disorders. In those aspects where the mammal in need has an autoimmune disorder, that disorder is selected from the group consisting of autoimmune hemolytic anemia, Crohn's disease, inflammatory bowel disease, multiple sclerosis, myasthenia gravis, rheumatoid arthritis, and systemic lupus erythematosus.

In other aspects of this embodiment, the allergic or inflammatory disorder is selected from the group consisting of asthma, rhinitis, ulcerative colitis, Crohn's disease, pancreatitis, gastritis, benign tumors, polyps, hereditary polyposis syndrome, colon cancer, rectal cancer, breast cancer, prostate cancer, stomach cancer, ulcerous disease of the digestive organs, stenocardia, atherosclerosis, myocardial infarction, sequelae of stenocardia or myocardial infarction, senile dementia, inflammation associated with microbial infection (e.g., fungal, bacterial, or viral), and cerebrovascular diseases. In yet other aspects the metabolic syndrome or diabetes associated disorder is selected from the group consisting of metabolic syndrome, diabetes type 1, diabetes type 2, insulin insensitivity and obesity.

In some aspects the cancer is selected from the group consisting of brain, breast, colon, kidney, leukemia, liver, lung, and prostate cancers. In yet other aspects of this embodiment the ocular disorder is selected from retinopathy, diabetic retinopathy, and macular degeneration. In still other aspects of this embodiment, the neurological disorder is selected from the group consisting of Alzheimer's disease, Parkinson's disease, multiple sclerosis, amyotrophic lateral sclerosis (ALS or Lou Gehrig's Disease), Huntington's disease, neurocognitive dysfunction, senile dementia, and mood disorder diseases.

The term "modulate" or "modulation" is used herein to mean the up or down regulation of expression or activity of the enzyme by a compound, ingredient, etc., to which it refers.

As used herein, the term "protein kinase" represent transferase class enzymes that are able to transfer a phosphate group from a donor molecule to an amino acid residue of a protein. See Kostich, M., et al., Human Members of the Eukaryotic Protein Kinase Family, *Genome Biology* 3(9): research0043.1-0043.12, 2002 herein incorporated by reference in its entirety, for a detailed discussion of protein kinases and family/group nomenclature.

Representative, non-limiting examples of kinases include Abl, Abl(T315I), ALK, ALK4, AMPK, Arg, Arg, ARK5, ASK1, Aurora-A, Axl, Blk, Bmx, BRK, BrSK1, BrSK2, BTK, CaMKI, CaMKII, CaMKIV, CDK1/cyclinB, CDK2/cyclinA, CDK2/cyclinE, CDK3/cyclinE, CDK5/p25, CDK5/p35, CDK6/cyclinD3, CDK7/cyclinH/MAT1, CDK9/cyclin T1, CHK1, CHK2, CK1(y), CK1δ, CK2, CK2α2, cKit (D816V), cKit, c-RAF, CSK, cSRC, DAPK1, DAPK2, DDR2, DMPK, DRAK1, DYRK2, EGFR, EGFR(L858R), EGFR(L861Q), EphA1, EphA2, EphA3, EphA4, EphA5, EphA7, EphA8, EphB1, EphB2, EphB3, EphB4, ErbB4, Fer, Fes, FGFR1, FGFR2, FGFR3, FGFR4, Fgr, Flt1, Flt3 (D835Y), Flt3, Flt4, Fms, Fyn, GSK3β, GSK3α, Hck, HIPK1, HIPK2, HIPK3, IGF-1R, IKKβ, IKKα, IR, IRAK1, IRAK4, IRR, ITK , JAK2, JAK3, JNK1α1, JNK2α2, JNK3, KDR, Lck, LIMK1, LKB1, LOK, Lyn, Lyn, MAPK1, MAPK2, MAPK2, MAPKAP-K2, MAPKAP-K3, MARK1, MEK1, MELK, Met, MINK, MKK4, MKK6, MKK7β, MLCK, MLK1, Mnk2, MRCKβ, MRCKα, MSK1, MSK2, MSSK1, MST1, MST2, MST3, MuSK, NEK2, NEK3, NEK6, NEK7, NLK, p70S6K, PAK2, PAK3, PAK4, PAK6, PAR-1Bα, PDGFRβ, PDGFRα, PDK1, PI3K beta, PI3K delta, PI3K gamma, Pim-1, Pim-2, PKA(b), PKA, PKBβ, PKBα, PKBγ, PKCμ, PKCβI, PKCβII, PKCα, PKCγ, PKCδ, PKCε, PKCζ, PKCη, PKCθ, PKCι, PKD2, PKG1β, PKG1α, Plk3, PRAK, PRK2, PrKX, PTK5, Pyk2, Ret, RIPK2, ROCK-I, ROCK-II, ROCK-II, Ron, Ros, Rse, Rsk1, Rsk1, Rsk2, Rsk3, SAPK2a, SAPK2a(T106M), SAPK2b, SAPK3, SAPK4, SGK, SGK2, SGK3, SIK, Snk, SRPK1, SRPK2, STK33, Syk, TAK1, TBK1, Tie2, TrkA; TrkB, TSSK1, TSSK2, WNK2, WNK3, Yes, ZAP-70, ZIPK. In some embodiments, the kinases may be ALK, Aurora-A, Axl, CDK9/cyclin T1, DAPK1, DAPK2, Fer, FGFR4, GSK3β, GSK3α, Hck, JNK2α2, MSK2, p70S6K, PAK3, PI3K delta, PI3K gamma, PKA, PKBβ, PKBα, Rse, Rsk2, Syk, TrkA, and TSSK1. In yet other embodiments the kinase is selected from the group consisting of ABL, AKT, AURORA, CDK, DBF2/20, EGFR, EPH/ELK/ECK, ERK/MAPKFGFR, GSK3, IKKB, INSR, JAK DOM ½, MARK/PRKAA, MEK/STE7, MEKK/STE11, MLK, mTOR, PAK/STE20, PDGFR, PI3K, PKC, POLO, SRC, TEC/ATK, and ZAP/SYK.

The methods and compositions of the present invention are intended for use with any mammal that may experience the benefits of the methods of the invention. Foremost among such mammals are humans, although the invention is not intended to be so limited, and is applicable to veterinary uses. Thus, in accordance with the invention, "mammals" or "mammal in need" include humans as well as non-human mammals, particularly domesticated animals including, without limitation, cats, dogs, and horses.

As used herein, "autoimmune disorder" refers to those diseases, illnesses, or conditions engendered when the host's systems are attacked by the host's own immune system. Representative, non-limiting examples of autoimmune diseases include alopecia areata, ankylosing spondylitis, arthritis, antiphospholipid syndrome, autoimmune Addison's disease, autoimmune hemolytic anemia, autoimmune inner ear disease (also known as Meniers disease), autoimmune lymphoproliferative syndrome (ALPS), autoimmune thrombocytopenic purpura, autoimmune hemolytic anemia, autoimmune hepatitis, Bechet's disease, Crohn's disease, diabetes mellitus type 1, glomerulonephritis, Graves' disease, Guillain-Barré syndrome, inflammatory bowel disease, lupus nephritis, multiple sclerosis, myasthenia gravis, pemphigus, pernicious anemia, polyarteritis nodosa, polymyositis, primary billiary cirrhosis, psoriasis, rheumatic fever, rheumatoid arthritis, scleroderma, Sjögren's syndrome, systemic lupus erythematosus, ulcerative colitis, vitiligo, and Wegener's granulamatosis. Representative, non-limiting examples of kinases associated with autoimmune disorders include BTK, ERK, FGFR, FMS, GSK, IGFR, IKK, JAK, PDGFR, PI3K, PKC, PLK, ROCK, and VEGFR.

"Allergic disorders", as used herein, refers to an exaggerated or pathological reaction (as by sneezing, respiratory distress, itching, or skin rashes) to substances, situations, or physical states that are without comparable effect on the average individual. As used herein, "inflammatory disorders" means a response (usually local) to cellular injury that is marked by capillary dilatation, leukocytic infiltration, redness, heat, pain, swelling, and often loss of function and that serves as a mechanism initiating the elimination of noxious agents and of damaged tissue. Examples of allergic or inflammatory disorders include, without limitation, asthma, rhinitis, ulcerative colitis, Crohn's disease, pancreatitis, gastritis, benign tumors, polyps, hereditary polyposis syndrome, colon cancer, rectal cancer, breast cancer, prostate cancer, stomach cancer, ulcerous disease of the digestive organs, stenocardia, atherosclerosis, myocardial infarction, sequelae of stenocardia or myocardial infarction, senile dementia, and cerebrovascular diseases. Representative, non-limiting examples of kinases associated with allergic disorders include AKT, BTK, EGFR, FYN, IKKB, ITK, JAK, KIT, LCK, LYN, MAPK, MEK, mTOR, PDGFR, PI3K, PKC, PPAR, ROCK, SRC, SYK, and ZAP.

As used herein, "metabolic syndrome" and "diabetes associated disorders" refers to insulin related disorders, i.e., to those diseases or conditions where the response to insulin is either causative of the disease or has been implicated in the progression or suppression of the disease or condition. Representative examples of insulin related disorders include, without limitation diabetes, diabetic complications, insulin sensitivity, polycystic ovary disease, hyperglycemia, dyslipidemia, insulin resistance, metabolic syndrome, obesity, body weight gain, inflammatory diseases, diseases of the digestive organs, stenocardia, myocardial infarction, sequelae of stenocardia or myocardial infarction, senile dementia, and cerebrovascular dementia. See, *Harrison's Principles of Internal Medicine,* 16h Ed., McGraw Hill Companies Inc., New York (2005). Examples, without limitation, of inflammatory conditions include diseases of the digestive organs (such as ulcerative colitis, Crohn's disease, pancreatitis, gastritis, benign tumor of the digestive organs, digestive polyps, hereditary polyposis syndrome, colon cancer, rectal cancer, stomach cancer and ulcerous diseases of the digestive organs), stenocardia, myocardial infarction, sequelae of stenocardia or myocardial infarction, senile dementia, cerebrovascular dementia, immunological diseases and cancer in general. Non-limiting examples of kinases associated with metabolic syndrome can include AKT, AMPK, CDK, ERK, GSK, IGFR, JNK, MAPK, MEK, PI3K, and PKC.

"Insulin resistance" refers to a reduced sensitivity to insulin by the body's insulin-dependent processes resulting in lowered activity of these processes or an increase in insulin production or both. Insulin resistance is typical of type 2 diabetes but may also occur in the absence of diabetes.

As used herein "diabetic complications" include, without limitation, retinopathy, muscle infarction, idiopathic skeletal hyperostosis and bone loss, foot ulcers, neuropathy, arteriosclerosis, respiratory autonomic neuropathy and structural derangement of the thorax and lung parenchyma, left ventricular hypertrophy, cardiovascular morbidity, progressive loss of kidney function, and anemia.

As used herein "cancer" refers to any of various benign or malignant neoplasms characterized by the proliferation of anaplastic cells that, if malignant, tend to invade surrounding tissue and metastasize to new body sites. Representative, non-limiting examples of cancers considered within the scope of this invention include brain, breast, colon, kidney, leukemia, liver, lung, and prostate cancers. Non-limiting examples of cancer associated protein kinases considered within the scope of this invention include ABL, AKT, Aurora, BRK, CDK, EGFR, ERB, FGFR, IGFR, KIT, MAPK, mTOR, PDGFR, PI3K, PKC, and SRC.

"Ocular disorders", refers to those disturbances in the structure or function of the eye resulting from developmental abnormality, disease, injury, age or toxin. Non-limiting examples of ocular disorders considered within the scope of the present invention include retinopathy, macular degeneration or diabetic retinopathy. Ocular disorder associated kinases include, without limitation, Aurora, EPH, ERB, ERK, FMS, IGFR, MEK, PDGFR, PI3K, PKC, SRC, and VEGFR.

A "neurological disorder", as used herein, refers to any disturbance in the structure or function of the central nervous system resulting from developmental abnormality, disease, injury or toxin. Representative, non-limiting examples of neurological disorders include Alzheimer's disease, Parkinson's disease, multiple sclerosis, amyotrophic lateral sclerosis (ALS or Lou Gehrig's Disease), Huntington's disease, neurocognitive dysfunction, senile dementia, and mood disorder diseases. Protein kinases associated with neurological disorders may include, without limitation, CDK, FYN, JNK, MAPK, PKC, ROCK, RTK, SRC, and VEGFR.

As used herein "cardiovascular disease" or "CVD" refers to those pathologies or conditions which impair the function of, or destroy cardiac tissue or blood vessels. Cardiovascular disease associated kinases include, without limitation, AKT, GRK, GSK, IKKB, JAK, JUN, MAPK, PKC, RHO, ROCK, and TOR.

"Osteoporosis", as used herein, refers to a disease in which the bones have become extremely porous, thereby making the bone more susceptible to fracture and slower healing. Protein kinases associated with osteoporosis include, without limitation, AKT, CAMK, IRAK-M, MAPK, mTOR, PPAR, RHO, ROS, SRC, SYR, and VEGFR.

An embodiment of the invention describes methods modulating the activity of a plurality of metabolic syndrome associated protein kinases in a subject in need thereof, wherein the protein kinase modulation is beneficial to the health of the subject. This method comprises administering to the subject in need a therapeutically effective amount of a composition comprising a 5:1 (w/w) ratio of rho-isoalpha acids to *Acacia nilotica* heartwood powder extract.

A further embodiment of the invention discloses composition for modulating the activity of a plurality of disease associated protein kinases in a subject in need thereof, where the protein kinase modulation is beneficial to the health of the subject. Compositions of this embodiment comprise a therapeutically effective amount of a compound selected from the group consisting of alpha acids, beta acids, prenylflavonoids, chalcones, isoalpha acids, reduced isoalpha acids, spent hops, and a compound or extract derived from acacia.

In some aspects of this embodiment the subject in need has a condition selected from the group consisting of autoimmune disorders, allergic or inflammatory disorders, metabolic syndrome or diabetes associated disorders, cancer, ocular disorders, and neurological disorders, while in other aspects the disease associated protein kinase is selected from the group consisting of ABL, AKT, AURORA, CDK, DBF2/20, EGFR, EPH/ELK/ECK, ERK/MAPKFGFR, GSK3, IKKB, INSR, JAK DOM ½, MARK/PRKAA, MEK/STE7, MEKK/STE11, MLK, mTOR, PAK/STE20, PDGFR, PI3K, PKC, POLO, SRC, TEC/ATK, and ZAP/SYK.

In still other aspects the alpha acid is selected from the group consisting of humulone, cohumulone, adhumulone, prehumulone, and posthumulone or the beta acid is selected from the group consisting of lupulone, colupulone, adlupulone, and prelupulone.

In yet other aspects the isoalpha acid of the composition used is selected from the group consisting of isohumulone, isoadhumulone, and isocohumulone. While the compositions employ RIAA, the RIAA is selected from the group consisting of dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. The rho-isoalpha acid configuration is employed in yet other aspects of this embodiment.

In some aspects of this embodiment the chalcone is xanthohumol or isoxanthohumol, or the prenylflavonoid is 6-prenylnaringenin or 8-prenylnaringenin.

In yet other aspects, the compound or extract derived from acacia is derived from *Acacia catechu* or *Acacia nilotica*. In those aspects where the acacia derived compound or extract is derived from *Acacia catechu* or *Acacia nilotica*, the *Acacia catechu* or *Acacia nilotica* compound is selected from the group consisting of gum resin, bark powder, heartwood powder, and an *Acacia catechu* or *Acacia nilotica* extract. In those aspects where the acacia derived compound is an *Acacia catechu* or *Acacia nilotica* extract, the extract is selected from acidic, alkaline, polar solvent, nonpolar solvent, and gastric fluid extracts.

Compositions of this embodiment may further comprise one or more members selected from the group consisting of antioxidants, vitamins, minerals, proteins, fats, and carbohydrates, or a pharmaceutically acceptable excipient selected from the group consisting of coatings, isotonic and absorption delaying agents, binders, adhesives, lubricants, disintegrants, coloring agents, flavoring agents, sweetening agents, absorbants, detergents, and emulsifying agents.

In some aspects of this embodiment, the composition used further comprises an antidiabetic drug selected from the group consisting of rosiglitazone, troglitazone, pioglitazone, and metformin.

In some aspects of this embodiment, the modulated kinase is selected from the group consisting of Abl, Abl(T315I), ALK, ALK4, AMPK, Arg, Arg, ARK5, ASK1, Aurora-A, Axl, Blk, Bmx, BRK, BrSK1, BrSK2, BTK, CaMKI, CaMKII, CaMKIV, CDK1/cyclinB, CDK2/cyclin, CDK2/cyclinE, CDK3/cyclinE, CDK5/p25, CDK5/p35, CDK6/cyclinD3, CDK7/cyclinH/MAT1, CDK9/cyclin T1, CHK1, CHK2, CK1(y), CK1δ, CK2, CK2α2, cKit(D816V), cKit, c-RAF, CSK, cSRC, DAPK1, DAPK2, DDR2, DMPK, DRAK1, DYRK2, EGFR, EGFR(L858R), EGFR(L861Q), EphA1, EphA2, EphA3, EphA4, EphA5, EphA7, EphA8, EphB1, EphB2, EphB3, EphB4, ErbB4, Fer, Fes, FGFR1, FGFR2, FGFR3, FGFR4, Fgr, Flt1, Flt3(D835Y), Flt3, Flt4, Fms, Fyn, GSK3β, GSK3α, Hck, HIPK1, HIPK2, HIPK3, IGF-1R, IKKβ, IKKα, IR, IRAK1, IRAK4, IRR, ITK, JAK2, JAK3, JNK1α1, JNK2α2, JNK3, KDR, Lck, LIMK1, LKB1, LOK, Lyn, Lyn, MAPK1, MAPK2, MAPK2, MAPKAP-K2, MAPKAP-K3, MARK1, MEK1, MELK, Met, MINK, MKK4, MKK6, MKK7β, MLCK, MLK1, Mnk2, MRCKβ, MRCKα, MSK1, MSK2, MSSK1, MST1, MST2, MST3, MuSK, NEK2, NEK3, NEK6, NEK7, NLK, p70S6K, PAK2, PAK3, PAK4, PAK6, PAR-1Bα, PDGFRβ, PDGFRα, PDK1, PI3K beta, PI3K delta, PI3K gamma, Pim-1, Pim-2, PKA(b), PKA, PKBβ, PKBα, PKBγ, PKCμ, PKCβI, PKCβII, PKCα, PKCγ, PKCδ, PKCε, PKCζ, PKCη, PKCθ, PKCι, PKD2, PKG1β, PKG1α, Plk3, PRAK, PRK2, PrKX, PTK5, Pyk2, Ret, RIPK2, ROCK-I, ROCK-II, ROCK-II, Ron, Ros, Rse, Rsk1, Rsk1, Rsk2, Rsk3, SAPK2a, SAPK2a(T106M), SAPK2b, SAPK3, SAPK4, SGK, SGK2, SGK3, SIK, Snk, SRPK1, SRPK2, STK33, Syk, TAK1, TBK1, Tie2, TrkA, TrkB, TSSK1, TSSK2, WNK2, WNK3, Yes, ZAP-70, and ZIPK.

In preferred aspects the modulated kinase is selected from the group consisting of Aurora-A, CDK2/cyclin A, DAPK1, DAPK2, EphA3FGFR4, GSK3β, GSK3α, Hck, MAPK1, MAPKAP-K2, MSK2, MSSK1, PI3K beta, PI3K delta, PI3K gamma, Rse, Rsk2, Syk, and Tie2. In more preferred aspects the modulated kinase is selected from the group consisting of ABL, AKT, AURORA, CDK, DBF2/20, EGFR, EPH/ELK/ECK, ERK/MAPKFGFR, GSK3, IKKB, INSR, JAK DOM ½, MARK/PRKAA, MEK/STE7, MEKK/STE11, MLK, mTOR, PAK/STE20, PDGFR, PI3K, PKC, POLO, SRC, TEC/ATK, and ZAP/SYK.

In some aspects, the mammal in need has a condition selected from the group consisting of autoimmune disorders, allergic or inflammatory disorders, metabolic syndrome or diabetes associated disorders, cancer, ocular disorders, and neurological disorders. In those aspects where the mammal in need has an autoimmune disorder, that disorder is selected from the group consisting of autoimmune hemolytic anemia, Crohn's disease, inflammatory bowel disease, multiple sclerosis, myasthenia gravis, rheumatoid arthritis, and systemic lupus erythematosus.

In other aspects of this embodiment, the allergic or inflammatory disorder is selected from the group consisting of asthma, rhinitis, ulcerative colitis, Crohn's disease, pancreatitis, gastritis, benign tumors, polyps, hereditary polyposis syndrome, colon cancer, rectal cancer, breast cancer, prostate cancer, stomach cancer, ulcerous disease of the digestive organs, stenocardia, atherosclerosis, myocardial infarction, sequelae of stenocardia or myocardial infarction, senile dementia, and cerebrovascular diseases. In yet other aspects the metabolic syndrome or diabetes associated disorder is selected from the group consisting of metabolic syndrome, diabetes type 1, diabetes type 2, insulin insensitivity and obesity.

In some aspects the cancer is selected from the group consisting of brain, breast, colon, kidney, leukemia, liver, lung, and prostate cancers. In yet other aspects of this embodiment the ocular disorder is selected from retinopathy, diabetic retinopathy, and macular degeneration. In still other aspects of this embodiment, the neurological disorder is selected from the group consisting of Alzheimer's disease, Parkinson's disease, multiple sclerosis, amyotrophic lateral sclerosis (ALS or Lou Gehrig's Disease), Huntington's disease, neurocognitive dysfunction, senile dementia, and mood disorder diseases.

Another embodiment of the invention describes compositions for modulating the activity of a plurality of metabolic syndrome associated protein kinases in a subject in need thereof, wherein the protein kinase modulation is beneficial to the health of the subject. These compositions comprise a therapeutically effective amount of a composition comprising a 5:1 (w/w) ratio of rho-isoalpha acids to *Acacia nilotica* heartwood powder extract.

Another embodiment of the invention discloses compositions for modulating the activity of a plurality of cancer associated protein kinases in a subject in need where the protein kinase modulation is beneficial to the health of the subject. In this embodiment the composition comprises a therapeutically effective amount of at least one member selected from the group consisting of:

a. from about 0.01 mg to about 10,000 mg of xanthohumol;
 b. from about 0.01 mg to about 10,000 mg of THIAA;
 c. from about 0.01 mg to about 10,000 mg of HHIAA;
 d. from about 0.01 mg to about 10,000 mg of RIAA;
 e. from about 0.01 mg to about 10,000 mg of IAA;
 f. from about 0.01 mg to about 10,000 mg of beta acids; and
 g. from about 0.01 mg to about 10,000 mg of alpha acids.

As used herein, by "treating" is meant reducing, preventing, and/or reversing the symptoms in the individual to which a compound of the invention has been administered, as compared to the symptoms of an individual not being treated according to the invention. A practitioner will appreciate that the compounds, compositions, and methods described herein are to be used in concomitance with continuous clinical evaluations by a skilled practitioner (physician or veterinarian) to determine subsequent therapy. Hence, following treatment the practitioners will evaluate any improvement in the treatment of the pulmonary inflammation according to standard methodologies. Such evaluation will aid and inform in evaluating whether to increase, reduce or continue a particular treatment dose, mode of administration, etc.

It will be understood that the subject to which a compound of the invention is administered need not suffer from a specific traumatic state. Indeed, the compounds of the invention may be administered prophylactically, prior to any development of symptoms. The term "therapeutic," "therapeutically," and permutations of these terms are used to encompass therapeutic, palliative as well as prophylactic uses. Hence, as used herein, by "treating or alleviating the symptoms" is meant reducing, preventing, and/or reversing the symptoms of the individual to which a compound of the invention has been administered, as compared to the symptoms of an individual receiving no such administration.

The term "therapeutically effective amount" is used to denote treatments at dosages effective to achieve the therapeutic result sought. Furthermore, one of skill will appreciate that the therapeutically effective amount of the compound of the invention may be lowered or increased by fine tuning and/or by administering more than one compound of the invention, or by administering a compound of the invention with another compound. See, for example, Meiner, C. L., "Clinical Trials: Design, Conduct, and Analysis," Monographs in Epidemiology and Biostatistics, Vol. 8 Oxford University Press, USA (1986). The invention therefore provides a method to tailor the administration/treatment to the particular exigencies specific to a given mammal. As illustrated in the following examples, therapeutically effective amounts may be easily determined for example empirically by starting at relatively low amounts and by step-wise increments with concurrent evaluation of beneficial effect.

It will be appreciated by those of skill in the art that the number of administrations of the compounds according to the invention will vary from patient to patient based on the particular medical status of that patient at any given time including other clinical factors such as age, weight and condition of the mammal and the route of administration chosen.

As used herein, "symptom" denotes any sensation or change in bodily function that is experienced by a patient and is associated with a particular disease, i.e., anything that accompanies "X" and is regarded as an indication of "X"'s existence. It is recognized and understood that symptoms will vary from disease to disease or condition to condition. By way of non-limiting examples, symptoms associated with autoimmune disorders include fatigue, dizziness, malaise, increase in size of an organ or tissue (for example, thyroid enlargement in Grave's Disease), or destruction of an organ or tissue resulting in decreased functioning of an organ or tissue (for example, the islet cells of the pancreas are destroyed in diabetes).

Representative symptomology for allergy associated diseases or conditions include absentmindedness, anaphylaxis, asthma, burning eyes, constipation, coughing, dark circles under or around the eyes, dermatitis, depression, diarrhea, difficulty swallowing, distraction or difficulty with concentration, dizziness, eczema, embarrassment, fatigue, flushing, headaches, heart palpitations, hives, impaired sense of smell, irritability/behavioral problems, itchy nose or skin or throat, joint aches muscle pains, nasal congestion, nasal polyps, nausea, postnasal drainage (postnasal drip), rapid pulse, rhinorrhea (runny nose), ringing—popping or fullness in the ears, shortness of breath, skin rashes, sleep difficulties, sneezing, swelling (angioedema), throat hoarseness, tingling nose, tiredness, vertigo, vomiting, watery or itchy or crusty or red eyes, and wheezing.

"Inflammation" or "inflammatory condition" as used herein refers to a local response to cellular injury that is marked by capillary dilatation, leukocytic infiltration, redness, heat, pain, swelling, and often loss of function and that serves as a mechanism initiating the elimination of noxious agents and of damaged tissue. Representative symptoms of inflammation or an inflammatory condition include, if confined to a joint, redness, swollen joint that's warm to touch, joint pain and stiffness, and loss of joint function. Systemic inflammatory responses can produce "flu-like" symptoms, such as, for instance, fever, chills, fatigue/loss of energy, headaches, loss of appetite, and muscle stiffness.

Diabetes and metabolic syndrome often go undiagnosed because many of their symptoms seem so harmless. For example, some diabetes symptoms include, without limitation: frequent urination, excessive thirst, extreme hunger, unusual weight loss, increased fatigue, irritability, and blurry vision.

Symptomology of neurological disorders may be variable and can include, without limitation, numbness, tingling, hyperesthesia (increased sensitivity), paralysis, localized weakness, dysarthria (difficult speech), aphasia (inability to speak), dysphagia (difficulty swallowing), diplopia (double vision), cognition issues (inability to concentrate, for example), memory loss, amaurosis fugax (temporary loss of vision in one eye) difficulty walking, incoordination, tremor, seizures, confusion, lethargy, dementia, delirium and coma.

In a further embodiment compositions for modulating the activity of a plurality of ocular disorder associated protein kinases in a subject, wherein said protein kinase modulation is beneficial to the health of the subject are described. Here the compositions comprise a therapeutically effective amount of a composition comprising from about 1 mg to about 1000 mg of vitamin C; from about 1 IU to about 1000 IU of vitamin E; from about 0.1 mg to about 2.5 mg of selenium; from about 1 mg to about 50 mg of zinc; from about 0.1 mg to about 10 mg of copper; from about 1 mg to about 15 mg of lutein; from about 0.05 mg to about 1 mg of zeaxanthin; and from about 1 mg to about 1000 mg of *Acacia nilotica* heartwood powder extract The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

Effects of Modified Hops Components on Protein Kinases

As stated above, kinases represent transferase class enzymes that are able to transfer a phosphate group from a donor molecule (usually ATP) to an amino acid residue of a protein (usually threonine, serine or tyrosine). Kinases are used in signal transduction for the regulation of enzymes, i.e., they can inhibit or activate the activity of an enzyme, such as in cholesterol biosynthesis, amino acid transformations, or glycogen turnover. While most kinases are specialized to a single kind of amino acid residue, some kinases exhibit dual activity in that they can phosphorylate two different kinds of amino acids. As shown in FIG. 1, kinases function in signal transduction and translation.

Methods—The inhibitory effect of 10 μg RIAA/ml of the present invention on human kinase activity was tested on a panel of over 200 kinases in the KinaseProfiler™ Assay (Upstate Cell Signaling Solutions, Upstate USA, Inc., Charlottesville, Va., USA). The assay protocols for specific kinases are summarized at http://www.upstate.com/img/pdf/kp_protocols_full.pdf (last visited on Jun. 12, 2006).

Results—Just over 205 human kinases were assayed in the cell free system. Surprisingly we discovered that the hops compounds tested inhibited 25 of the 205 kinases by 10% or greater. Eight (8) of the 205 were inhibited by >20%; 5 of 205 were inhibited by >30; and 2 were inhibited by about 50%.

Specifically in the PI3kinase pathway, hops inhibits PI3Kγ, PI3Kδ, PI3Kβ, Akt1, Akt2, GSK3α, GSK3β, P70S6K. It should be noted that mTOR was not available for testing.

The inhibitory effects of the hops compounds RIAA on the kinases tested are shown in Table 1 below.

TABLE 1

Kinase inhibition by RIAA tested in the KinaseProfiler™ Assay at 10 μg/ml

| Kinase | % of Control |
| --- | --- |
| Abl | 93 |
| Abl | 102 |
| Abl(T315I) | 121 |
| ALK | 84 |
| ALK4 | 109 |
| AMPK | 103 |
| Arg | 96 |
| Arg | 95 |
| ARK5 | 103 |
| ASK1 | 116 |
| Aurora-A | 77 |
| Axl | 89 |
| Blk | 115 |
| Bmx | 108 |
| BRK | 112 |
| BrSK1 | 108 |
| BrSK2 | 100 |
| BTK | 97 |
| CaMKI | 96 |
| CaMKII | 119 |
| CaMKIV | 115 |
| CDK1/cyclinB | 109 |
| CDK2/cyclinA | 94 |
| CDK2/cyclinE | 122 |
| CDK3/cyclinE | 104 |
| CDK5/p25 | 100 |
| CDK5/p35 | 103 |
| CDK6/cyclinD3 | 110 |
| CDK7/cyclinH/MAT1 | 108 |
| CDK9/cyclin T1 | 84 |
| CHK1 | 102 |
| CHK2 | 98 |
| CK1(y) | 109 |
| CK1δ | 104 |
| CK2 | 122 |
| CK2α2 | 126 |
| cKit(D816V) | 135 |
| cKit | 103 |
| c-RAF | 101 |
| CSK | 108 |
| cSRC | 103 |
| DAPK1 | 78 |
| DAPK2 | 67 |
| DDR2 | 108 |
| DMPK | 121 |
| DRAK1 | 111 |
| DYRK2 | 112 |
| EGFR | 120 |
| EGFR(L858R) | 113 |
| EGFR(L861Q) | 122 |
| EphA1 | 105 |
| EphA2 | 115 |
| EphA3 | 93 |
| EphA4 | 108 |
| EphA5 | 120 |
| EphA7 | 127 |
| EphA8 | 112 |
| EphB1 | 134 |
| EphB2 | 110 |
| EphB3 | 101 |
| EphB4 | 113 |
| ErbB4 | 123 |
| Fer | 80 |
| Fes | 121 |
| FGFR1 | 96 |
| FGFR2 | 103 |
| FGFR3 | 109 |
| FGFR4 | 83 |
| Fgr | 102 |
| Flt1 | 102 |
| Flt3(D835Y) | 103 |
| Flt3 | 108 |
| Flt4 | 110 |
| Fms | 105 |
| Fyn | 100 |
| GSK3β | 82 |
| GSK3α | 89 |
| Hck | 83 |
| HIPK1 | 98 |
| HIPK2 | 113 |
| HIPK3 | 119 |
| IGF-1R | 97 |
| IKKβ | 117 |
| IKKα | 117 |
| IR | 95 |
| IRAK1 | 109 |
| IRAK4 | 110 |
| IRR | 102 |
| ITK | 117 |
| JAK2 | 112 |
| JAK3 | 111 |

TABLE 1-continued

Kinase inhibition by RIAA tested in the KinaseProfiler™ Assay at 10 μg/ml

| Kinase | % of Control |
|---|---|
| JNK1α1 | 104 |
| JNK2α2 | 84 |
| JNK3 | 98 |
| KDR | 101 |
| Lck | 94 |
| LIMK1 | 102 |
| LKB1 | 106 |
| LOK | 127 |
| Lyn | 100 |
| Lyn | 109 |
| MAPK1 | 95 |
| MAPK2 | 101 |
| MAPK2 | 113 |
| MAPKAP-K2 | 98 |
| MAPKAP-K3 | 97 |
| MARK1 | 101 |
| MEK1 | 113 |
| MELK | 98 |
| Met | 109 |
| MINK | 109 |
| MKK4 | 94 |
| MKK6 | 114 |
| MKK7β | 113 |
| MLCK | 114 |
| MLK1 | 109 |
| Mnk2 | 116 |
| MRCKβ | 114 |
| MRCKα | 119 |
| MSK1 | 97 |
| MSK2 | 89 |
| MSSK1 | 92 |
| MST1 | 105 |
| MST2 | 103 |
| MST3 | 104 |
| MuSK | 100 |
| NEK2 | 99 |
| NEK3 | 109 |
| NEK6 | 98 |
| NEK7 | 98 |
| NLK | 109 |
| p70S6K | 87 |
| PAK2 | 92 |
| PAK3 | 54 |
| PAK4 | 99 |
| PAK6 | 109 |
| PAR-1Bα | 109 |
| PDGFRβ | 109 |
| PDGFRα | 101 |
| PDK1 | 118 |
| PI3K beta | 95 |
| PI3K delta | 88 |
| PI3K gamma | 80 |
| Pim-1 | 133 |
| Pim-2 | 112 |
| PKA(b) | 99 |
| PKA | 66 |
| PKBβ | 87 |
| PKBα | 49 |
| PKBγ | 100 |
| PKCμ | 100 |
| PKCβI | 112 |
| PKCβII | 99 |
| PKCα | 109 |
| PKCγ | 109 |
| PKCδ | 101 |
| PKCε | 99 |
| PKCζ | 107 |
| PKCη | 119 |
| PKCθ | 117 |
| PKCι | 96 |
| PKD2 | 115 |
| PKG1β | 99 |
| PKG1α | 110 |
| Plk3 | 98 |
| PRAK | 100 |
| PRK2 | 102 |
| PrKX | 94 |
| PTK5 | 104 |
| Pyk2 | 112 |
| Ret | 96 |
| RIPK2 | 98 |
| ROCK-I | 105 |
| ROCK-II | 90 |
| ROCK-II | 105 |
| Ron | 102 |
| Ros | 94 |
| Rse | 84 |
| Rsk1 | 93 |
| Rsk1 | 95 |
| Rsk2 | 89 |
| Rsk3 | 95 |
| SAPK2a | 111 |
| SAPK2a(T106M) | 108 |
| SAPK2b | 100 |
| SAPK3 | 98 |
| SAPK4 | 98 |
| SGK | 94 |
| SGK2 | 96 |
| SGK3 | 107 |
| SIK | 90 |
| Snk | 98 |
| SRPK1 | 117 |
| SRPK2 | 110 |
| STK33 | 94 |
| Syk | 82 |
| TAK1 | 109 |
| TBK1 | 121 |
| Tie2 | 95 |
| TrkA | 85 |
| TrkB | 91 |
| TSSK1 | 51 |
| TSSK2 | 97 |
| WNK2 | 102 |
| WNK3 | 104 |
| Yes | 92 |
| ZAP-70 | 113 |
| ZIPK | 91 |

It should be noted that several kinases in the PI3K pathway are being preferentially inhibited by RIAA, for example, Akt1 at 51% inhibition. It is interesting to note that three Akt isoforms exist. Akt1 null mice are viable, but retarded in growth [Cho et al., Science 292:1728-1731 (2001)]. Drosophila eye cells deficient in Akt1 are reduced in size [Verdu et al., Nat cell Biol 1:500-505 (1999)]; overexpression leads to increased size from normal. Akt2 null mice are viable but have impaired glucose control [Cho et al., J Biol Chem 276: 38345-38352 (2001)]. Hence, it appears Akt1 plays a role in size determination and Akt2 is involved in insulin signaling.

The PI3K pathway is known to play a key role in mRNA stability and mRNA translation selection resulting in differential protein expression of various oncogene proteins and inflammatory pathway proteins. A particular 5' mRNA structure denoted 5'-TOP has been shown to be a key structure in the regulation of mRNA translation selection.

A review of the cPLA literature and DNA sequence indicates that the 5' mRNA of human cPLA2 contains a consensus (82% homology to a known oncogene regulated similarly) sequence indicating that it too has a 5'TOP structure. sPLAs, also known to be implicated in inflammation, also have this same 5'-TOP. Moreover, this indicates that cPLA2 and possibly other PLAs are upregulated by the PI3K pathway via increasing the translation selection of cPLA2 mRNA resulting in increases in cPLA2 protein. Conversely, inhibitors of PI3K should reduce the amount of cPLA2 and reduce $PGE_2$ formation made via the COX2 pathway.

Taken together the kinase data and our own results where we have discovered that hops compounds inhibit cPLA2 protein expression (Western blots, data not shown) but not mRNA, suggests that the anti-inflammatory mode of action of hops compounds may be via reducing substrate availability to COX2 by reducing cPLA2 protein levels, and perhaps more specifically, by inhibiting the PI3K pathway resulting in the inhibition of activation of TOP mRNA translation.

The exact pathway of activity remains unclear. Some reports are consistent with the model that activation occurs via phosphorylation of one or more of the six isoforms of ribosomal protein S6 (RPS6). RPS6 is reported to resolve the 5'TOP mRNA allowing efficient translation into protein. However, Stolovich et al. Mol Cell Biol December, 8101-8113 (2002), disputes this model and proposes that Akt1 phosphorylates an unknown translation factor, X, which allows TOP mRNA translation.

Example 2

Figure 2:
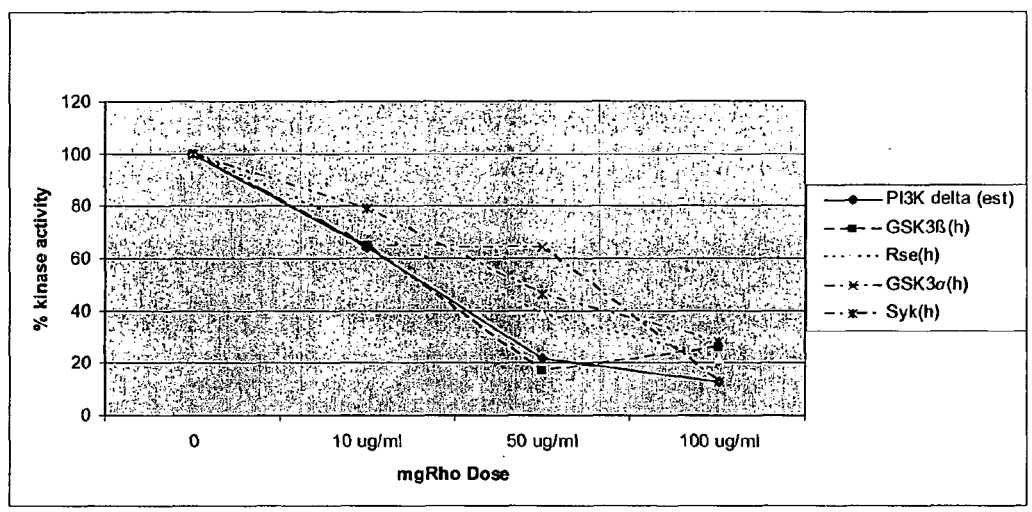
FIG. 2 graphically depicts the inhibition of five selected kinases by MgRIAA (mgRho).

Dose Response Effects of Hops or *Acacia* Components on Selected Protein Kinases The dose responsiveness of mgRho was tested at approximately 10, 50, and 100 µg/ml on over sixty selected protein kinases according to the protocols of Example 1 are presented as Table 2 below. The five kinases which were inhibited the most are displayed graphically as FIG. 2.

The dose responsiveness for kinase inhibition (reported as a percent of control) of a THIAA preparation was tested at approximately 1, 10, 25, and 50 ug/ml on 86 selected kinases as presented in Table 3 below. Similarly, an acacia preparation was tested at approximately 1, 5, and 25 ug/ml on over 230 selected protein kinases according to the protocols of Example I and are presented as Table 4 below. Preparations of isoalpha acids (IAA), heaxahydroisoalpha acids (HHIAA), beta acids, and xanthohumol were also tested at approximately 1, 10, 25, and 50 ug/ml on 86 selected kinases and the dose responsiveness results are presented below as Tables 5-8 respectively.

TABLE 2

Dose response effect (as % of Control) of a mgRho on selected protein kinases

| Kinase | 10 ug/ml | 50 ug/ml | 100 ug/ml |
|---|---|---|---|
| Abl | 103 | 82 | 65 |
| ALK | 79 | 93 | 109 |
| AMPK | 107 | 105 | 110 |
| Arg | 94 | 76 | 64 |
| Aurora-A | 96 | 59 | 33 |
| Axl | 101 | 87 | 85 |
| CaMKI | 95 | 85 | 77 |
| CDK2/cyclinA | 106 | 81 | 59 |
| CDK9/cyclin T1 | 100 | 88 | 101 |
| c-RAF | 105 | 109 | 103 |
| DAPK1 | 82 | 56 | 51 |
| DAPK2 | 64 | 51 | 45 |
| EphA3 | 103 | 64 | 55 |
| Fer | 87 | 74 | 83 |
| FGFR1 | 98 | 99 | 93 |
| FGFR4 | 111 | 68 | 35 |
| GSK3β | 65 | 17 | 26 |
| GSK3α | 65 | 64 | 13 |
| Hck | 86 | 72 | 59 |
| IKKβ | 104 | 91 | 92 |
| IKKα | 104 | 101 | 96 |

TABLE 2-continued

Dose response effect (as % of Control) of a mgRho on selected protein kinases

| Kinase | 10 ug/ml | 50 ug/ml | 100 ug/ml |
|---|---|---|---|
| IR | 87 | 85 | 78 |
| JNK1α1 | 105 | 115 | 106 |
| JNK2α2 | 119 | 136 | 124 |
| JNK3 | 98 | 98 | 86 |
| Lck | 105 | 83 | 81 |
| MAPK1 | 77 | 53 | 44 |
| MAPK2 | 101 | 104 | 106 |
| MAPKAP-K2 | 111 | 99 | 49 |
| MAPKAP-K3 | 109 | 106 | 73 |
| MEK1 | 106 | 104 | 91 |
| MKK4 | 110 | 110 | 98 |
| MSK2 | 92 | 54 | 43 |
| MSSK1 | 120 | 31 | 26 |
| p70S6K | 105 | 86 | 69 |
| PAK2 | 99 | 84 | 89 |
| PAK5 | 99 | 94 | 78 |
| PASK | 105 | 111 | 102 |
| PDK1 | 98 | 90 | 78 |
| PI3K beta (est) | 74 | 49 | 39 |
| PI3K delta (est) | 64 | 22 | 13 |
| PI3K gamma (est) | 85 | 69 | 55 |
| PKA | 103 | 95 | 92 |
| PKCε | 96 | 93 | 91 |
| PKCι | 100 | 94 | 96 |
| PrKX | 100 | 105 | 90 |
| ROCK-II | 102 | 101 | 99 |
| Ros | 105 | 86 | 90 |
| Rse | 71 | 39 | 22 |
| Rsk2 | 108 | 79 | 56 |
| Rsk3 | 108 | 102 | 86 |
| SAPK2a | 96 | 105 | 109 |
| SAPK2a(T106M) | 100 | 107 | 107 |
| SAPK2b | 101 | 102 | 106 |
| SAPK3 | 110 | 109 | 110 |
| SAPK4 | 97 | 107 | 109 |
| SGK | 111 | 105 | 94 |
| SIK | 130 | 125 | 117 |
| STK33 | 99 | 96 | 103 |
| Syk | 79 | 46 | 28 |
| Tie2 | 113 | 74 | 56 |
| TrkA | 127 | 115 | 93 |
| TrkB | 106 | 105 | 81 |
| TSSK1 | 105 | 100 | 95 |
| Yes | 100 | 105 | 100 |
| ZIPK | 92 | 62 | 83 |

TABLE 3

Dose response effect (as % of Control) of THIAA on selected protein kinases

| Kinase | 1 ug/ml | 5 ug/ml | 25 ug/ml | 50 ug/ml |
|---|---|---|---|---|
| Abl(T315I) | 104 | 95 | 68 | 10 |
| ALK4 | 127 | 112 | 108 | |
| AMPK | 135 | 136 | 139 | 62 |
| Aurora-A | 102 | 86 | 50 | 5 |
| Bmx | 110 | 105 | 57 | 30 |
| BTK | 104 | 86 | 58 | 48 |
| CaMKI | 163 | 132 | 65 | 16 |
| CaMKIIβ | 106 | 102 | 90 | 71 |
| CaMKIIγ | 99 | 101 | 87 | 81 |
| CaMKIIδ | 99 | 103 | 80 | 76 |
| CaMKIV | 99 | 117 | 120 | 126 |
| CaMKIδ | 91 | 95 | 61 | 43 |
| CDK1/cyclinB | 82 | 101 | 77 | 66 |
| CDK2/cyclinA | 118 | 113 | 87 | 50 |
| CDK2/cyclinE | 87 | 79 | 73 | 57 |
| CDK3/cyclinE | 113 | 111 | 105 | 32 |
| CDK5/p25 | 102 | 100 | 85 | 54 |
| CDK5/p35 | 109 | 106 | 89 | 80 |
| CDK6/cyclinD3 | 114 | 113 | 112 | 70 |

TABLE 3-continued

Dose response effect (as % of Control) of THIAA on selected protein kinases

| Kinase | 1 ug/ml | 5 ug/ml | 25 ug/ml | 50 ug/ml |
|---|---|---|---|---|
| CDK9/cyclin T1 | 106 | 93 | 66 | 36 |
| CHK1 | 116 | 118 | 149 | 148 |
| CHK2 | 111 | 116 | 98 | 68 |
| CK1(y) | 101 | 101 | 55 | |
| CK1γ1 | 101 | 100 | 42 | 43 |
| CK1γ2 | 94 | 85 | 33 | 48 |
| CK1γ3 | 99 | 91 | 23 | 18 |
| CK1δ | 109 | 97 | 65 | 42 |
| cKit(D816H) | 113 | 113 | 69 | 75 |
| CSK | 110 | 113 | 92 | 137 |
| cSRC | 105 | 103 | 91 | 17 |
| DAPK1 | 62 | 34 | 21 | 14 |
| DAPK2 | 60 | 54 | 41 | 17 |
| DRAK1 | 113 | 116 | 75 | 18 |
| EphA2 | 110 | 112 | 85 | 31 |
| EphA8 | 110 | 110 | 83 | 43 |
| EphB1 | 153 | 177 | 196 | 53 |
| ErbB4 | 124 | 125 | 75 | 56 |
| Fer | 85 | 41 | 24 | 12 |
| Fes | 112 | 134 | 116 | 57 |
| FGFR1 | 109 | 110 | 110 | 111 |
| FGFR1(V561M) | 97 | 106 | 91 | 92 |
| FGFR2 | 126 | 115 | 58 | 7 |
| FGFR3 | 112 | 94 | 39 | 16 |
| FGFR4 | 122 | 93 | 83 | 58 |
| Fgr | 121 | 120 | 110 | 47 |
| Flt4 | 126 | 119 | 85 | 31 |
| IKKα | 139 | 140 | 140 | 102 |
| JNK1α1 | 71 | 118 | 118 | 107 |
| JNK2α2 | 94 | 97 | 98 | 101 |
| JNK3 | 121 | 78 | 58 | 44 |
| KDR | 106 | 107 | 104 | 126 |
| Lck | 97 | 105 | 125 | 88 |
| LKB1 | 145 | 144 | 140 | 140 |
| MAPK2 | 99 | 109 | 112 | 102 |
| Pim-1 | 103 | 100 | 44 | 44 |
| Pim-2 | 103 | 109 | 83 | 22 |
| PKA(b) | 104 | 77 | 32 | 0 |
| PKA | 104 | 101 | 90 | 25 |
| PKBβ | 117 | 102 | 27 | 33 |
| PKBα | 103 | 101 | 49 | 50 |
| PKBγ | 107 | 109 | 99 | 33 |
| PKCμ | 90 | 90 | 93 | 87 |
| PKCβII | 99 | 107 | 103 | 64 |
| PKCα | 110 | 111 | 112 | 102 |
| PKCγ | 86 | 95 | 77 | 62 |
| PKCδ | 97 | 93 | 84 | 87 |
| PKCε | 76 | 88 | 88 | 90 |
| PKCζ | 93 | 100 | 107 | 103 |
| PKCη | 82 | 99 | 103 | 90 |
| PKCθ | 93 | 95 | 86 | 90 |
| PKCι | 77 | 90 | 93 | 134 |
| PRAK | 99 | 81 | 21 | 33 |
| PrKX | 92 | 76 | 32 | 38 |
| Ron | 120 | 110 | 97 | 42 |
| Ros | 105 | 105 | 94 | 93 |
| Rsk1 | 101 | 87 | 48 | 31 |
| Rsk2 | 100 | 85 | 40 | 14 |
| SGK | 98 | 103 | 79 | 77 |
| SGK2 | 117 | 110 | 45 | 18 |
| Syk | 99 | 93 | 55 | 17 |
| TBK1 | 101 | 100 | 82 | 56 |
| Tie2 | 109 | 115 | 100 | 32 |
| TrkA | 107 | 65 | 30 | 15 |
| TrkB | 97 | 96 | 72 | 21 |
| TSSK2 | 112 | 111 | 87 | 66 |
| ZIPK | 106 | 101 | 74 | 59 |

TABLE 4

Dose response effect (as % of Control) of acacia on selected protein kinases

| Kinase | 1 ug/ml | 5 ug/ml | 25 ug/ml |
|---|---|---|---|
| Abl | 53 | 27 | 2 |
| Abl(T315I) | 57 | 26 | 11 |
| ALK | 102 | 52 | 10 |
| ALK4 | 84 | 96 | 98 |
| AMPK | 108 | 101 | 77 |
| Arg | 86 | 53 | 23 |
| Arg | 106 | 55 | 18 |
| ARK5 | 36 | 13 | 6 |
| ASK1 | 100 | 70 | 23 |
| Aurora-A | 8 | −1 | 3 |
| Axl | 64 | 17 | 4 |
| Blk | 31 | −2 | −3 |
| Bmx | 101 | 51 | 0 |
| BRK | 47 | 19 | 7 |
| BrSK1 | 58 | 6 | 2 |
| BrSK2 | 82 | 16 | 4 |
| BTK | 15 | −1 | −3 |
| CaMKI | 97 | 90 | 49 |
| CaMKII | 83 | 50 | 6 |
| CaMKIIβ | 87 | 45 | 10 |
| CaMKIIγ | 90 | 51 | 12 |
| CaMKIIδ | 25 | 13 | 6 |
| CaMKIV | 89 | 44 | 44 |
| CaMKIδ | 69 | 19 | 10 |
| CDK1/cyclinB | 62 | 48 | 9 |
| CDK2/cyclinA | 69 | 15 | 5 |
| CDK2/cyclinE | 51 | 14 | 8 |
| CDK3/cyclinE | 41 | 13 | 4 |
| CDK5/p25 | 82 | 41 | 7 |
| CDK5/p35 | 77 | 46 | 13 |
| CDK6/cyclinD3 | 100 | 54 | 5 |
| CDK7/cyclinH/MAT1 | 124 | 90 | 42 |
| CDK9/cyclin T1 | 79 | 21 | 4 |
| CHK1 | 87 | 52 | 17 |
| CHK2 | 52 | 16 | 5 |
| CK1(y) | 77 | 32 | 3 |
| CK1γ1 | 51 | 7 | −4 |
| CK1γ2 | 31 | 5 | 1 |
| CK1γ3 | 49 | 16 | 0 |
| CK1δ | 60 | 15 | 6 |
| CK2 | 157 | 162 | 128 |
| CK2α2 | 95 | 83 | 51 |
| cKit(D816H) | 27 | 7 | 2 |
| cKit(D816V) | 111 | 91 | 41 |
| cKit | 94 | 68 | 24 |
| cKit(V560G) | 49 | 5 | 0 |
| cKit(V654A) | 30 | 8 | 3 |
| CLK3 | 33 | 16 | 6 |
| c-RAF | 105 | 100 | 87 |
| CSK | 74 | 19 | 1 |
| cSRC | 99 | 12 | 0 |
| DAPK1 | 90 | 72 | 12 |
| DAPK2 | 75 | 31 | 4 |
| DCAMKL2 | 107 | 106 | 77 |
| DDR2 | 84 | 91 | 45 |
| DMPK | 105 | 106 | 116 |
| DRAK1 | 92 | 40 | 11 |
| DYRK2 | 83 | 55 | 25 |
| eEF-2K | 103 | 97 | 59 |
| EGFR | 76 | 26 | 6 |
| EGFR(L858R) | 99 | 40 | 1 |
| EGFR(L861Q) | 90 | 49 | 1 |
| EGFR(T790M) | 93 | 29 | 7 |
| EGFR(T790M, L858R) | 74 | 30 | 4 |
| EphA1 | 106 | 43 | 9 |
| EphA2 | 94 | 82 | 6 |
| EphA3 | 94 | 83 | 50 |
| EphA4 | 55 | 12 | 6 |
| EphA5 | 100 | 28 | 10 |
| EphA7 | 103 | 80 | 6 |
| EphA8 | 113 | 84 | 19 |
| EphB1 | 116 | 63 | 8 |
| EphB2 | 30 | 5 | 2 |
| EphB3 | 109 | 35 | 1 |

TABLE 4-continued

Dose response effect (as % of Control) of acacia on selected protein kinases

| Kinase | 1 ug/ml | 5 ug/ml | 25 ug/ml |
|---|---|---|---|
| EphB4 | 30 | 11 | 3 |
| ErbB4 | 61 | 8 | 0 |
| FAK | 106 | 78 | 2 |
| Fer | 106 | 134 | 28 |
| Fes | 143 | 74 | 43 |
| FGFR1 | 125 | 26 | 3 |
| FGFR1(V561M) | 92 | 50 | 2 |
| FGFR2 | 73 | −2 | −5 |
| FGFR3 | 21 | 3 | 1 |
| FGFR4 | 30 | 7 | 5 |
| Fgr | 78 | 18 | 7 |
| Flt1 | 41 | 12 | 1 |
| Flt3(D835Y) | 65 | 15 | −1 |
| Flt3 | 76 | 16 | 3 |
| Flt4 | 12 | 3 | 2 |
| Fms | 94 | 73 | 19 |
| Fyn | 23 | 5 | 1 |
| GRK5 | 96 | 91 | 81 |
| GRK6 | 117 | 117 | 94 |
| GSK3β | 13 | 5 | 4 |
| GSK3α | 5 | 2 | 1 |
| Hck | 87 | 29 | −2 |
| HIPK1 | 110 | 112 | 62 |
| HIPK2 | 92 | 71 | 24 |
| HIPK3 | 106 | 92 | 56 |
| IGF-1R | 148 | 122 | 41 |
| IKKβ | 30 | 6 | 3 |
| IKKα | 120 | 86 | 11 |
| IR | 121 | 123 | 129 |
| IRAK1 | 98 | 85 | 49 |
| IRAK4 | 117 | 95 | 47 |
| IRR | 91 | 70 | 28 |
| Itk | 121 | 114 | 48 |
| JAK2 | 83 | 69 | 23 |
| JAK3 | 24 | 7 | 1 |
| JNK1α1 | 118 | 110 | 75 |
| JNK2α2 | 99 | 106 | 102 |
| JNK3 | 52 | 23 | 3 |
| KDR | 90 | 60 | 18 |
| Lck | 92 | 93 | 25 |
| LIMK1 | 108 | 104 | 53 |
| LKB1 | 126 | 122 | 98 |
| LOK | 103 | 72 | 27 |
| Lyn | 4 | 1 | 2 |
| MAPK1 | 115 | 38 | 15 |
| MAPK2 | 108 | 90 | 48 |
| MAPK2 | 99 | 78 | 45 |
| MAPKAP-K2 | 67 | 12 | 1 |
| MAPKAP-K3 | 82 | 28 | 1 |
| MARK1 | 52 | 20 | 4 |
| MEK1 | 117 | 94 | 41 |
| MELK | 61 | 27 | 2 |
| Mer | 95 | 74 | 5 |
| Met | 168 | 21 | 7 |
| MINK | 79 | 57 | 18 |
| MKK4 | 103 | 135 | 13 |
| MKK6 | 113 | 105 | 50 |
| MKK7β | 91 | 44 | 9 |
| MLCK | 83 | 38 | 52 |
| MLK1 | 92 | 75 | 42 |
| Mnk2 | 103 | 71 | 29 |
| MRCKβ | 95 | 52 | 18 |
| MRCKα | 96 | 76 | 32 |
| MSK1 | 105 | 97 | 33 |
| MSK2 | 56 | 22 | 12 |
| MSSK1 | 12 | 4 | 4 |
| MST1 | 58 | 36 | 17 |
| MST2 | 106 | 104 | 38 |
| MST3 | 50 | 10 | 2 |
| MuSK | 97 | 83 | 63 |
| NEK11 | 89 | 58 | 19 |
| NEK2 | 99 | 100 | 37 |
| NEK3 | 79 | 41 | 18 |
| NEK6 | 78 | 43 | 4 |
| NEK7 | 110 | 94 | 27 |
| NLK | 103 | 90 | 44 |
| p70S6K | 43 | 17 | 10 |
| PAK2 | 103 | 79 | 16 |
| PAK3 | 43 | 5 | 3 |
| PAK4 | 99 | 91 | 58 |
| PAK5 | 69 | 6 | 2 |
| PAK6 | 77 | 22 | 1 |
| PAR-1Bα | 70 | 20 | 8 |
| PASK | 136 | 114 | 26 |
| PDGFRβ | 59 | 19 | 9 |
| PDGFRα(D842V) | 60 | 11 | 5 |
| PDGFRα | 100 | 106 | 51 |
| PDGFRα(V561D) | 59 | 11 | 7 |
| PDK1 | 97 | 57 | 16 |
| PhKγ2 | 67 | 62 | 16 |
| Pim-1 | 44 | 9 | 2 |
| Pim-2 | 82 | 17 | 10 |
| PKA(b) | 104 | 52 | 7 |
| PKA | 99 | 85 | 16 |
| PKBβ | 61 | 9 | −1 |
| PKBα | 98 | 67 | 8 |
| PKBγ | 86 | 50 | 5 |
| PKCμ | 90 | 81 | 44 |
| PKCβI | 108 | 112 | 100 |
| PKCβII | 71 | 47 | 30 |
| PKCα | 75 | 34 | 32 |
| PKCγ | 72 | 47 | 27 |
| PKCδ | 105 | 94 | 63 |
| PKCε | 108 | 90 | 59 |
| PKCζ | 34 | 10 | 2 |
| PKCη | 107 | 99 | 84 |
| PKCθ | 88 | 31 | 21 |
| PKCι | 66 | 69 | 63 |
| PKD2 | 106 | 108 | 81 |
| PKG1β | 31 | 16 | 5 |
| PKG1α | 41 | 18 | 7 |
| Plk3 | 114 | 106 | 115 |
| PRAK | 18 | 18 | 35 |
| PRK2 | 92 | 35 | 8 |
| PrKX | 49 | 14 | 16 |
| PTK5 | 99 | 95 | 88 |
| Pyk2 | 90 | 45 | 9 |
| Ret | 23 | −1 | −2 |
| RIPK2 | 103 | 95 | 64 |
| ROCK-I | 95 | 90 | 54 |
| ROCK-II | 100 | 66 | 39 |
| ROCK-II | 91 | 59 | 39 |
| Ron | 32 | 2 | 4 |
| Ros | 95 | 40 | 35 |
| Rse | 35 | 14 | 0 |
| Rsk1 | 45 | 9 | 4 |
| Rsk1 | 75 | 8 | 5 |
| Rsk2 | 60 | 4 | 3 |
| Rsk3 | 78 | 31 | 7 |
| Rsk4 | 71 | 25 | 12 |
| SAPK2a | 99 | 106 | 106 |
| SAPK2a(T106M) | 110 | 106 | 80 |
| SAPK2b | 99 | 100 | 77 |
| SAPK3 | 108 | 79 | 40 |
| SAPK4 | 103 | 86 | 57 |
| SGK | 89 | 34 | 2 |
| SGK2 | 102 | 36 | 5 |
| SGK3 | 103 | 96 | 34 |
| SIK | 115 | 28 | 5 |
| Snk | 93 | 96 | 61 |
| SRPK1 | 56 | 14 | 6 |
| SRPK2 | 37 | 15 | 4 |
| STK33 | 100 | 94 | 64 |
| Syk | 2 | 2 | 3 |
| TAK1 | 105 | 101 | 86 |
| TAO2 | 97 | 64 | 25 |
| TBK1 | 37 | 5 | 12 |
| Tie2 | 97 | 67 | 7 |

TABLE 4-continued

Dose response effect (as % of Control) of acacia on selected protein kinases

| Kinase | 1 ug/ml | 5 ug/ml | 25 ug/ml |
|---|---|---|---|
| TrkA | 20 | 4 | 2 |
| TrkB | 22 | 0 | 0 |
| TSSK1 | 89 | 10 | 5 |
| TSSK2 | 97 | 29 | 2 |
| VRK2 | 98 | 88 | 67 |
| WNK2 | 96 | 75 | 21 |
| WNK3 | 110 | 98 | 38 |
| Yes | 63 | 33 | 3 |
| ZAP-70 | 57 | 19 | 10 |
| ZIPK | 104 | 81 | 28 |

TABLE 5

Dose response effect (as % of Control) of IAA on selected protein kinases

| Kinase | 1 ug/ml | 5 ug/ml | 25 ug/ml | 50 ug/ml |
|---|---|---|---|---|
| Abl(T315I) | 104 | 119 | 84 | 56 |
| ALK4 | 92 | 110 | 113 | |
| AMPK | 122 | 121 | 86 | 49 |
| Aurora-A | 103 | 106 | 61 | 20 |
| Bmx | 90 | 125 | 108 | 43 |
| BTK | 96 | 102 | 62 | 48 |
| CaMKI | 126 | 139 | 146 | 54 |
| CDK1/cyclinB | 96 | 102 | 86 | 69 |
| CDK2/cyclinA | 102 | 111 | 98 | 59 |
| CDK2/cyclinE | 81 | 89 | 72 | 55 |
| CDK3/cyclinE | 99 | 121 | 107 | 62 |
| CDK5/p25 | 88 | 108 | 95 | 69 |
| CDK5/p35 | 92 | 117 | 100 | 73 |
| CDK6/cyclinD3 | 111 | 119 | 108 | 64 |
| CDK9/cyclin T1 | 87 | 109 | 77 | 51 |
| CHK1 | 105 | 117 | 140 | 159 |
| CHK2 | 102 | 106 | 75 | 46 |
| CK1(y) | 94 | 105 | 103 | |
| CK1γ1 | 98 | 102 | 69 | 21 |
| CK1γ2 | 89 | 88 | 39 | 42 |
| CK1γ3 | 91 | 87 | 26 | 17 |
| CK1δ | 95 | 111 | 90 | 56 |
| cKit(D816H) | 98 | 117 | 100 | 59 |
| CSK | 95 | 111 | 72 | 86 |
| cSRC | 99 | 111 | 100 | 53 |
| DAPK1 | 73 | 52 | 36 | 21 |
| DAPK2 | 59 | 54 | 50 | 47 |
| DRAK1 | 102 | 123 | 129 | 75 |
| EphA2 | 104 | 118 | 108 | 88 |
| EphA8 | 113 | 120 | 117 | 98 |
| EphB1 | 112 | 151 | 220 | 208 |
| ErbB4 | 93 | 107 | 110 | 20 |
| Fer | 95 | 76 | 49 | 38 |
| Fes | 101 | 110 | 120 | 59 |
| FGFR2 | 85 | 122 | 97 | 5 |
| Fgr | 99 | 120 | 119 | 70 |
| Flt4 | 85 | 37 | 74 | 33 |
| Fyn | 90 | 88 | 92 | 90 |
| GSK3β | 86 | 77 | 47 | 14 |
| GSK3α | 85 | 83 | 56 | 17 |
| Hck | 88 | 81 | 76 | 4 |
| HIPK2 | 101 | 107 | 107 | 84 |
| HIPK3 | 97 | 101 | 127 | 84 |
| IGF-1R | 132 | 229 | 278 | 301 |
| IKKβ | 103 | 116 | 93 | 56 |
| IR | 110 | 107 | 121 | 131 |
| IRAK1 | 115 | 143 | 156 | 122 |
| JAK3 | 88 | 98 | 83 | 74 |
| Lyn | 82 | 114 | 41 | 73 |
| MAPK1 | 81 | 87 | 55 | 55 |
| MAPKAP-K2 | 100 | 98 | 82 | 36 |
| MAPKAP-K3 | 108 | 113 | 106 | 80 |
| MINK | 102 | 122 | 118 | 127 |

TABLE 5-continued

Dose response effect (as % of Control) of IAA on selected protein kinases

| Kinase | 1 ug/ml | 5 ug/ml | 25 ug/ml | 50 ug/ml |
|---|---|---|---|---|
| MSK1 | 99 | 103 | 66 | 61 |
| MSK2 | 95 | 90 | 44 | 45 |
| MSSK1 | 90 | 78 | 52 | 52 |
| p70S6K | 94 | 98 | 84 | 58 |
| PAK3 | 91 | 66 | 21 | 11 |
| PAK5 | 101 | 108 | 106 | 59 |
| PAK6 | 98 | 109 | 106 | 102 |
| PhKγ2 | 103 | 109 | 102 | 66 |
| Pim-1 | 104 | 106 | 77 | 46 |
| Pim-2 | 101 | 108 | 88 | 60 |
| PKA(b) | 104 | 115 | 86 | 12 |
| PKA | 110 | 102 | 99 | 106 |
| PKBβ | 104 | 110 | 57 | 76 |
| PKBα | 98 | 103 | 91 | 72 |
| PKBγ | 103 | 108 | 104 | 76 |
| PKCβII | 103 | 103 | 102 | 59 |
| PKCα | 106 | 104 | 89 | 46 |
| PRAK | 99 | 91 | 38 | 18 |
| PrKX | 94 | 92 | 91 | 58 |
| Ron | 117 | 113 | 113 | 40 |
| Ros | 101 | 108 | 84 | 75 |
| Rsk1 | 96 | 101 | 72 | 48 |
| Rsk2 | 95 | 101 | 76 | 36 |
| SGK | 102 | 110 | 100 | 96 |
| SGK2 | 99 | 128 | 105 | 60 |
| Syk | 85 | 92 | 53 | 7 |
| TBK1 | 100 | 105 | 82 | 86 |
| Tie2 | 101 | 124 | 113 | 40 |
| TrkA | 112 | 139 | 24 | 20 |
| TrkB | 97 | 111 | 90 | 59 |
| TSSK2 | 99 | 112 | 109 | 75 |
| ZIPK | 102 | 102 | 95 | 73 |

TABLE 6

Dose response effect (as % of Control) of HHIAA on selected protein kinases

| Kinase | 1 ug/ml | 5 ug/ml | 25 ug/ml | 50 ug/ml |
|---|---|---|---|---|
| Abl(T315I) | 113 | 109 | 84 | 38 |
| ALK4 | 123 | 121 | 108 | |
| AMPK | 133 | 130 | 137 | 87 |
| Aurora-A | 111 | 107 | 64 | 27 |
| Bmx | 103 | 102 | 106 | 44 |
| BTK | 110 | 105 | 67 | 61 |
| CaMKI | 148 | 151 | 140 | 56 |
| CDK1/cyclinB | 118 | 115 | 98 | 85 |
| CDK2/cyclinA | 109 | 112 | 82 | 60 |
| CDK2/cyclinE | 83 | 84 | 70 | 88 |
| CDK3/cyclinE | 115 | 119 | 108 | 85 |
| CDK5/p25 | 101 | 94 | 69 | 51 |
| CDK5/p35 | 110 | 103 | 73 | 68 |
| CDK6/cyclinD3 | 119 | 124 | 117 | 83 |
| CDK9/cyclin T1 | 106 | 96 | 66 | 40 |
| CHK1 | 127 | 124 | 140 | 144 |
| CHK2 | 119 | 117 | 110 | 82 |
| CK1(y) | 102 | 102 | 100 | |
| CK1γ1 | 105 | 103 | 68 | 30 |
| CK1γ2 | 99 | 99 | 45 | 49 |
| CK1γ3 | 104 | 98 | 28 | 22 |
| CK1δ | 110 | 115 | 89 | 56 |
| cKit(D816H) | 116 | 109 | 91 | 67 |
| CSK | 100 | 108 | 109 | 112 |
| cSRC | 105 | 114 | 103 | 37 |
| DAPK1 | 94 | 67 | 37 | 27 |
| DAPK2 | 72 | 58 | 46 | 47 |
| DRAK1 | 110 | 119 | 103 | 69 |
| EphA2 | 106 | 127 | 115 | 68 |
| EphA8 | 133 | 109 | 89 | 74 |
| EphB1 | 154 | 162 | 200 | 164 |
| ErbB4 | 141 | 122 | 85 | 14 |

TABLE 6-continued

Dose response effect (as % of Control) of HHIAA on selected protein kinases

| Kinase | 1 ug/ml | 5 ug/ml | 25 ug/ml | 50 ug/ml |
|---|---|---|---|---|
| Fer | 90 | 62 | 13 | 20 |
| Fes | 137 | 126 | 111 | 81 |
| FGFR2 | 116 | 120 | 71 | 7 |
| Fgr | 122 | 127 | 118 | 91 |
| Flt4 | 135 | 116 | 88 | 58 |
| Fyn | 104 | 119 | 82 | 81 |
| GSK3β | 138 | 84 | 51 | 10 |
| GSK3α | 89 | 82 | 58 | 18 |
| Hck | 93 | 99 | 73 | 77 |
| HIPK2 | 103 | 105 | 100 | 98 |
| HIPK3 | 117 | 121 | 118 | 29 |
| IGF-1R | 138 | 173 | 207 | 159 |
| IKKβ | 123 | 116 | 98 | 79 |
| IR | 129 | 95 | 105 | 81 |
| IRAK1 | 142 | 140 | 152 | 120 |
| JAK3 | 104 | 103 | 61 | 90 |
| Lyn | 115 | 113 | 56 | 80 |
| MAPK1 | 100 | 88 | 55 | 67 |
| MAPKAP-K2 | 104 | 99 | 71 | 29 |
| MAPKAP-K3 | 111 | 109 | 99 | 77 |
| MINK | 107 | 102 | 114 | 123 |
| MSK1 | 105 | 101 | 58 | 69 |
| MSK2 | 101 | 86 | 39 | 48 |
| MSSK1 | 98 | 78 | 41 | 60 |
| p70S6K | 108 | 99 | 78 | 56 |
| PAK3 | 113 | 24 | 14 | 10 |
| PAK5 | 109 | 105 | 89 | 36 |
| PAK6 | 106 | 106 | 88 | 71 |
| PhKγ2 | 105 | 109 | 85 | 54 |
| Pim-1 | 107 | 110 | 81 | 50 |
| Pim-2 | 111 | 106 | 98 | 58 |
| PKA(b) | 105 | 119 | 67 | 12 |
| PKA | 98 | 107 | 102 | 91 |
| PKBβ | 121 | 142 | 50 | 42 |
| PKBα | 105 | 108 | 81 | 57 |
| PKBγ | 115 | 116 | 107 | 42 |
| PKCβII | 113 | 115 | 109 | 95 |
| PKCα | 110 | 90 | 105 | 103 |
| PRAK | 109 | 89 | 41 | 33 |
| PrKX | 86 | 88 | 77 | 59 |
| Ron | 114 | 106 | 129 | 74 |
| Ros | 113 | 107 | 109 | 98 |
| Rsk1 | 101 | 102 | 53 | 60 |
| Rsk2 | 105 | 103 | 58 | 25 |
| SGK | 108 | 114 | 112 | 64 |
| SGK2 | 120 | 121 | 96 | 63 |
| Syk | 100 | 95 | 68 | 17 |
| TBK1 | 115 | 103 | 99 | 114 |
| Tie2 | 109 | 120 | 95 | 43 |
| TrkA | 87 | 73 | 41 | 24 |
| TrkB | 100 | 107 | 97 | 13 |
| TSSK2 | 115 | 112 | 109 | 71 |
| ZIPK | 109 | 109 | 96 | 8 |

TABLE 7

Dose response effect (as % of Control) of beta acids on selected protein kinases

| Kinase | 1 ug/ml | 5 ug/ml | 25 ug/ml | 50 ug/ml |
|---|---|---|---|---|
| Abl(T315I) | 101 | 101 | 70 | 29 |
| ALK4 | 108 | 114 | 90 | |
| AMPK | 136 | 131 | 135 | 77 |
| Aurora-A | 110 | 85 | 43 | 2 |
| Bmx | 111 | 100 | 93 | 54 |
| BTK | 96 | 90 | 14 | 37 |
| CaMKI | 142 | 142 | 131 | 57 |
| CDK1/cyclinB | 116 | 120 | 95 | 65 |
| CDK2/cyclinA | 106 | 104 | 94 | 64 |
| CDK2/cyclinE | 93 | 86 | 81 | 65 |
| CDK3/cyclinE | 119 | 115 | 96 | 53 |

TABLE 7-continued

Dose response effect (as % of Control) of beta acids on selected protein kinases

| Kinase | 1 ug/ml | 5 ug/ml | 25 ug/ml | 50 ug/ml |
|---|---|---|---|---|
| CDK5/p25 | 97 | 97 | 95 | 96 |
| CDK5/p35 | 109 | 106 | 90 | 50 |
| CDK6/cyclinD3 | 107 | 117 | 101 | 76 |
| CDK9/cyclin T1 | 101 | 104 | 88 | 35 |
| CHK1 | 111 | 125 | 144 | 164 |
| CHK2 | 103 | 100 | 94 | 69 |
| CK1(y) | 102 | 104 | 83 | |
| CK1γ1 | 100 | 95 | 82 | 33 |
| CK1γ2 | 97 | 83 | 55 | 44 |
| CK1γ3 | 99 | 75 | 40 | 21 |
| CK1δ | 103 | 98 | 81 | 54 |
| cKit(D816H) | 103 | 112 | 100 | 18 |
| CSK | 107 | 111 | 108 | 145 |
| cSRC | 104 | 99 | 90 | 19 |
| DAPK1 | 109 | 106 | 88 | 59 |
| DAPK2 | 97 | 76 | 57 | 45 |
| DRAK1 | 124 | 134 | 107 | 51 |
| EphA2 | 116 | 122 | 115 | 80 |
| EphA8 | 107 | 105 | 86 | 36 |
| EphB1 | 130 | 164 | 204 | 207 |
| ErbB4 | 111 | 118 | 116 | 28 |
| Fer | 78 | 69 | 30 | 18 |
| Fes | 120 | 106 | 114 | 79 |
| FGFR2 | 130 | 118 | 99 | 7 |
| Fgr | 119 | 119 | 127 | 62 |
| Flt4 | 104 | 96 | 65 | 22 |
| Fyn | 99 | 94 | 86 | 78 |
| GSK3β | 83 | 67 | 27 | 4 |
| GSK3α | 70 | 71 | 31 | 1 |
| Hck | 102 | 88 | 61 | 22 |
| HIPK2 | 101 | 104 | 99 | 94 |
| HIPK3 | 109 | 119 | 118 | 83 |
| IGF-1R | 101 | 163 | 262 | 260 |
| IKKβ | 110 | 113 | 85 | 59 |
| IR | 106 | 106 | 108 | 95 |
| IRAK1 | 143 | 155 | 165 | 158 |
| JAK3 | 100 | 98 | 64 | 38 |
| Lyn | 114 | 120 | 68 | 59 |
| MAPK1 | 88 | 75 | 51 | 37 |
| MAPKAP-K2 | 111 | 104 | 65 | 22 |
| MAPKAP-K3 | 108 | 106 | 102 | 69 |
| MINK | 102 | 103 | 123 | 140 |
| MSK1 | 106 | 97 | 54 | 36 |
| MSK2 | 96 | 86 | 28 | 25 |
| MSSK1 | 95 | 82 | 61 | 67 |
| p70S6K | 89 | 95 | 69 | 44 |
| PAK3 | 103 | 40 | 16 | 11 |
| PAK5 | 103 | 99 | 81 | 44 |
| PAK6 | 103 | 98 | 82 | 83 |
| PhKγ2 | 108 | 103 | 79 | 40 |
| Pim-1 | 104 | 97 | 57 | 21 |
| Pim-2 | 103 | 101 | 68 | 73 |
| PKA(b) | 120 | 104 | 51 | 3 |
| PKA | 103 | 105 | 102 | 28 |
| PKBβ | 114 | 108 | 56 | 52 |
| PKBα | 98 | 95 | 80 | 58 |
| PKBγ | 105 | 104 | 101 | 52 |
| PKCβII | 107 | 105 | 100 | 49 |
| PKCα | 108 | 104 | 98 | 54 |
| PRAK | 105 | 81 | 24 | 11 |
| PrKX | 93 | 86 | 68 | 29 |
| Ron | 108 | 119 | 98 | 44 |
| Ros | 107 | 103 | 80 | 98 |
| Rsk1 | 103 | 99 | 69 | 17 |
| Rsk2 | 98 | 96 | 56 | 8 |
| SGK | 109 | 111 | 98 | 100 |
| SGK2 | 123 | 113 | 84 | 0 |
| Syk | 92 | 81 | 62 | 16 |
| TBK1 | 110 | 103 | 80 | 78 |
| Tie2 | 110 | 100 | 106 | 79 |
| TrkA | 97 | 66 | 53 | 18 |
| TrkB | 105 | 100 | 86 | 11 |
| TSSK2 | 112 | 109 | 103 | 62 |
| ZIPK | 105 | 110 | 85 | 37 |

TABLE 8

Dose response effect (as % of Control) of xanthohumol on selected protein kinases

| Kinase | 1 ug/ml | 5 ug/ml | 25 ug/ml | 50 ug/ml |
|---|---|---|---|---|
| Abl(T315I) | 126 | 115 | 16 | 4 |
| ALK4 | 116 | 100 | 71 | 49 |
| AMPK | 122 | 113 | 90 | 81 |
| Aurora-A | 83 | 27 | 3 | 8 |
| Bmx | 108 | 97 | 22 | 0 |
| BTK | 109 | 57 | 2 | 20 |
| CaMKI | 142 | 83 | 3 | 4 |
| CDK1/cyclinB | 118 | 103 | 46 | 18 |
| CDK2/cyclinA | 107 | 96 | 57 | 6 |
| CDK2/cyclinE | 82 | 86 | 18 | 9 |
| CDK3/cyclinE | 101 | 100 | 37 | 8 |
| CDK5/p25 | 97 | 97 | 24 | 87 |
| CDK5/p35 | 103 | 102 | 41 | 44 |
| CDK6/cyclinD3 | 110 | 79 | 23 | 7 |
| CDK9/cyclin T1 | 110 | 107 | 45 | 31 |
| CHK1 | 121 | 126 | 142 | 149 |
| CHK2 | 25 | 5 | 3 | 2 |
| CK1(γ) | 91 | 63 | 37 | 9 |
| CK1γ1 | 101 | 79 | 50 | 26 |
| CK1γ2 | 92 | 48 | 30 | 12 |
| CK1γ3 | 98 | 51 | 22 | 15 |
| CK1δ | 75 | 32 | 16 | 12 |
| cKit(D816H) | 94 | 45 | 14 | 0 |
| CSK | 113 | 113 | 93 | 100 |
| cSRC | 92 | 50 | 27 | 21 |
| DAPK1 | 113 | 85 | 49 | 20 |
| DAPK2 | 105 | 88 | 45 | 26 |
| DRAK1 | 133 | 40 | 19 | −5 |
| EphA2 | 124 | 113 | 121 | 52 |
| EphA8 | 103 | 92 | 29 | 19 |
| EphB1 | 92 | 122 | 175 | 161 |
| ErbB4 | 132 | 85 | 52 | 27 |
| Fer | 55 | 20 | 10 | 1 |
| Fes | 131 | 106 | 102 | 26 |
| FGFR2 | 116 | 89 | 36 | 4 |
| Fgr | 101 | 36 | 10 | 0 |
| Flt4 | 74 | 10 | 11 | 4 |
| Fyn | 104 | 66 | 42 | 18 |
| GSK3β | 120 | 99 | 25 | 3 |
| GSK3α | 102 | 81 | 11 | −4 |
| Hck | 85 | 35 | 17 | 0 |
| HIPK2 | 110 | 98 | 75 | 37 |
| HIPK3 | 106 | 102 | 90 | 59 |
| IGF-1R | 107 | 113 | 129 | 139 |
| IKKβ | 145 | 118 | 61 | 44 |
| IR | 120 | 108 | 97 | 103 |
| IRAK1 | 129 | 104 | 81 | 36 |
| JAK3 | 104 | 84 | 17 | 5 |
| Lyn | 97 | 40 | 4 | 2 |
| MAPK1 | 91 | 64 | 19 | 17 |
| MAPKAP-K2 | 99 | 95 | 6 | 8 |
| MAPKAP-K3 | 100 | 99 | 17 | 7 |
| MINK | 42 | 10 | 5 | 7 |
| MSK1 | 114 | 92 | 31 | 9 |
| MSK2 | 126 | 61 | 8 | 19 |
| MSSK1 | 47 | 11 | 7 | 5 |
| p70S6K | 94 | 48 | 19 | 7 |
| PAK3 | 21 | 18 | 8 | 4 |
| PAK5 | 106 | 99 | 42 | 5 |
| PAK6 | 105 | 94 | 14 | 2 |
| PhKγ2 | 106 | 60 | 11 | 5 |
| Pim-1 | 88 | 35 | 4 | 3 |
| Pim-2 | 104 | 48 | 14 | 6 |
| PKA(b) | 137 | 113 | 33 | 2 |
| PKA | 105 | 109 | 98 | 21 |
| PKBβ | 146 | 102 | 1 | 8 |
| PKBα | 102 | 81 | 18 | 5 |
| PKBγ | 104 | 104 | 12 | 4 |
| PKCβII | 108 | 108 | 71 | 79 |
| PKCα | 100 | 100 | 75 | 83 |
| PRAK | 101 | 53 | 2 | 2 |
| PrKX | 92 | 75 | 2 | 3 |
| Ron | 135 | 127 | 60 | 69 |
| Ros | 101 | 99 | 85 | 94 |
| Rsk1 | 34 | 49 | 4 | 0 |
| Rsk2 | 96 | 43 | 3 | 4 |
| SGK | 111 | 84 | 0 | 3 |
| SGK2 | 130 | 110 | 2 | −4 |
| Syk | 95 | 60 | 32 | 17 |
| TBK1 | 104 | 71 | 45 | 42 |
| Tie2 | 94 | 96 | 100 | 35 |
| TrkA | 36 | 19 | 8 | 3 |
| TrkB | 95 | 89 | 58 | 3 |
| TSSK2 | 102 | 95 | 61 | 48 |
| ZIPK | 115 | 74 | 20 | 70 |

Results—The effect on kinase activity modulation by the various compounds tested displayed a wide range of modulatory effects depending on the specific kinase and compound tested (Tables 2-8) with representative examples enumerated below.

PI3Kδ, a kinase strongly implicated in autoimmune diseases such as, for example, rheumatoid arthritis and lupus erythematosus, exhibited a response inhibiting 36%, 78% and 87% of kinase activity at 10, 50, and 100 ug/ml respectively for MgRho. MgRho inhibited Syk in a dose dependent manner with 21%, 54% and 72% inhibition at 10, 50, and 100 µg/ml respectively. Additionally, GSK or glycogen synthase kinase (both GSK alpha and beta) displayed inhibition following mgRho exposure (alpha, 35, 36, 87% inhibition; beta, 35, 83, 74% inhibition respectively at 10, 50, 100 µg/ml). See Table 2.

THIAA displayed a dose dependent inhibition of kinase activity for many of the kinases examined with inhibition of FGFR2 of 7%, 16%, 77%, and 91% at 1, 5, 25, and 50 µg/ml respectively. Similar results were observed for FGFR3 (0%, 6%, 61%, and 84%) and TrkA (24%, 45%, 93%, and 94%) at 1, 5, 25, and 50 µg/ml respectively. See Table 3.

The acacia extract tested (*A. nilotica*) appeared to be the most potent inhibitor of kinase activity examined (Table 4), demonstrating 80% or greater inhibition of activity for such kinases as Syk (98%), Lyn (96%), GSK3α(95%), Aurora-A (92%), Flt4 (88%), MSSK1 (88%), GSK3β (87%), BTK (85%), PRAK (82%), and TrkA (80%), all at a 1 µg/ml exposure.

Example 3

Effect of Hops Components on PI3K Activity

Figure 3:
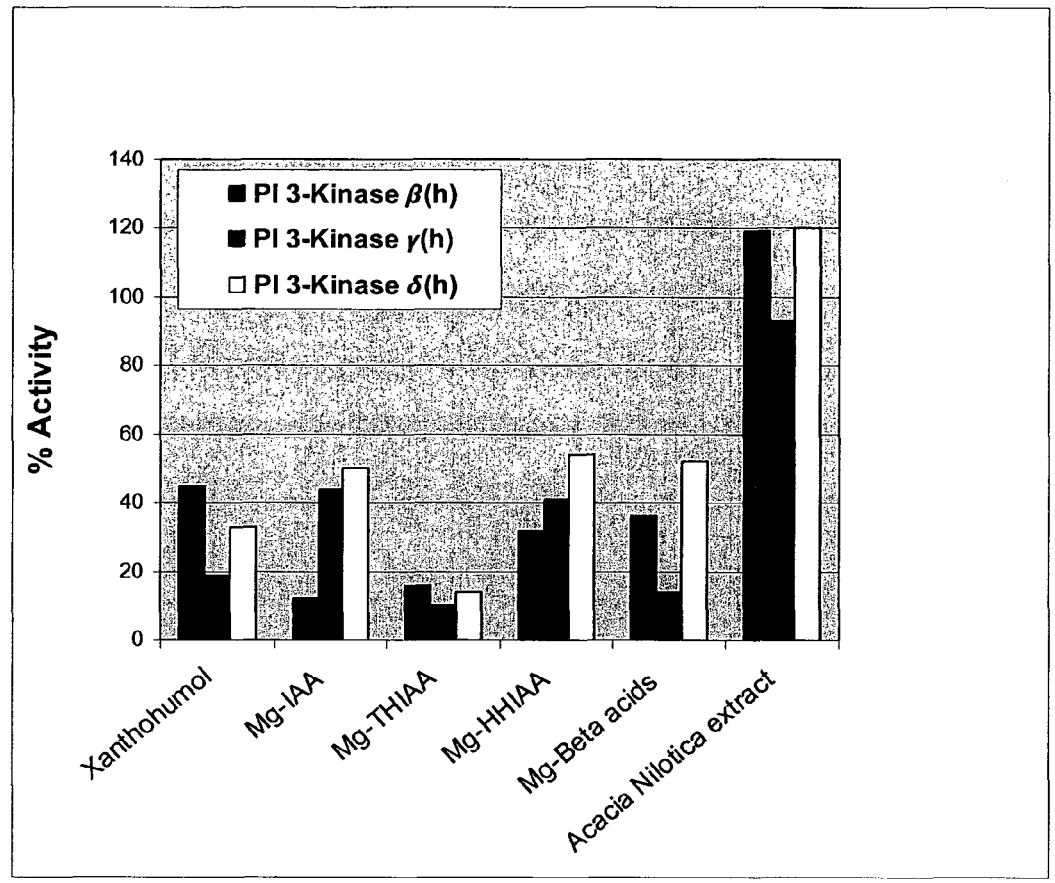
FIG. 3 graphically depicts the inhibition of PI3K isoforms by five hops components and a *Acacia nilotica* extract.

The inhibitory effect on human PI3K-β, PI3K-γ, and PI3K-δ of the hops components xanthohumol and the magnesium salts of beta acids, isoalpha acids (Mg-IAA), tetrahydro-isoalpha acids (Mg-THIAA), and hexahydro-isoalpha acids (Mg-HHIAA) were examined according to the procedures and protocols of Example 1. Additionally examined was an *Acacia nilotica* heartwood extract. All compounds were tested at 50 µg/ml. The results are presented graphically as FIG. 3.

It should be noted that all of the hops compounds tested showed >50% inhibition of PI3K activity with Mg-THIAA producing the greatest overall inhibition (>80% inhibition for all PI3K isoforms tested). Further note that both xanthohumol and Mg-beta acids were more inhibitory to PI3K-γ than to PI3K-β or PI3K-δ. Mg-IAA was approximately 3-fold more inhibitory to PI3K-β than to PI3K-γ or PI3K-δ. The *Acacia nilotica* heartwood extract appeared to stimulate PI3K-β or PI3K-δ activity. Comparable results were obtained for Syk and GSK kinases (data not shown).

Example 4

Inhibition of $PGE_2$ Synthesis in Stimulated and Nonstimmulated Murine Macrophages by Hops Compounds and Derivatives The objective of this example was to assess the extent to which hops derivatives inhibited COX-2 synthesis of $PGE_2$ preferentially over COX-1 synthesis of $PGE_2$ in the murine RAW 264.7 macrophage model. The RAW 264.7 cell line is a well-established model for assessing anti-inflammatory activity of test agents. Stimulation of RAW 264.7 cells with bacterial lipopolysaccharide induces the expression of COX-2 and production of $PGE_2$. Inhibition of $PGE_2$ synthesis is used as a metric for anti-inflammatory activity of the test agent. Equipment, Chemicals and Reagents, $PGE_2$ assay, and calculations are described below.

Equipment—Equipment used in this example included an OHAS Model #E01140 analytical balance, a Forma Model #F1214 biosafety cabinet (Marietta, Ohio), various pipettes to deliver 0.1 to 100 µl (VWR, Rochester, N.Y.), a cell hand tally counter (VWR Catalog #23609-102, Rochester, N.Y.), a Forma Model #F3210 $CO_2$ incubator (Marietta, Ohio), a hemocytometer (Hausser Model #1492, Horsham, Pa.), a Leica Model #DM IL inverted microscope (Wetzlar, Germany), a PURELAB Plus Water Polishing System (U.S. Filter, Lowell, Mass.), a 4° C. refrigerator (Forma Model #F3775, Marietta, Ohio), a vortex mixer (VWR Catalog #33994-306, Rochester, N.Y.), and a 37° C. water bath (Shel Lab Model #1203, Cornelius, Oreg.).

Chemicals and Reagents—Bacterial lipopolysaccharide (LPS; B *E. coli* 055:B5) was from Sigma (St. Louis, Mo.). Heat inactivated Fetal Bovine Serum (FBS-HI Cat. #35-011CV), and Dulbecco's Modification of Eagle's Medium (DMEM Cat #10-013CV) was purchased from Mediatech (Herndon, Va.). Hops fractions (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), (7) tetrahop (tetrahydro-iso-alpha acids THIAA) and (8) spent hops were obtained from Betatech Hops Products (Washington, D.C., U.S.A.). The spent hops were extracted two times with equal volumes of absolute ethanol. The ethanol was removed by heating at 40° C. until a only thick brown residue remained. This residue was dissolved in DMSO for testing in RAW 264.7 cells.

Test materials—Hops derivatives as described in Table 12 were used. The COX-1 selective inhibitor aspirin and COX-2 selective inhibitor celecoxib were used as positive controls. Aspirin was obtained from Sigma (St. Louis, Mo.) and the commercial formulation of celecoxib was used (Celebrex™, Searle & Co., Chicago, Ill.).

Cell culture and treatment with test material—RAW 264.7 cells, obtained from American Type Culture Collection (Catalog #TIB-71, Manassas, Va.), were grown in Dulbecco's Modification of Eagle's Medium (DMEM, Mediatech, Herndon, Va.) and maintained in log phase. The DMEM growth medium was made by adding 50 ml of heat inactivated FBS and 5 ml of penicillin/streptomycin to a 500 ml bottle of DMEM and storing at 4° C. The growth medium was warmed to 37° C. in water bath before use.

For COX-2 associated $PGE_2$ synthesis, 100 µl of medium was removed from each well of the cell plates prepared on day one and replaced with 100 µl of equilibrated 2× final concentration of the test compounds. Cells were then incubated for 90 minutes. Twenty µl of LPS were added to each well of cells to be stimulated to achieve a final concentration of 1 µg LPS/ml and the cells were incubated for 4 h. The cells were further incubated with 5 µM arachadonic acid for 15 minutes. Twenty-five µl of supernatant medium from each well was transferred to a clean microfuge tube for the determination of $PGE_2$ released into the medium.

For COX-1 associated $PGE_2$ synthesis, 100 µl of medium were removed from each well of the cell plates prepared on day one and replaced with 100 µl of equilibrated 2× final concentration of the test compounds. Cells were then incubated for 90 minutes. Next, instead of LPS stimulation, the cells were incubated with 100 µM arachadonic acid for 15 minutes. Twenty-five µl of supernatant medium from each well was transferred to a clean microfuge tube for the determination of $PGE_2$ released into the medium.

The appearance of the cells was observed and viability was assessed visually. No apparent toxicity was observed at the highest concentrations tested for any of the compounds. Twenty-five µl of supernatant medium from each well was transferred to a clean microfuge tube for the determination of $PGE_2$ released into the medium. $PGE_2$ was determined and reported as previously described below.

$PGE_2$ assay—A commercial, non-radioactive procedure for quantification of $PGE_2$ was employed (Caymen Chemical, Ann Arbor, Mich.) and the recommended procedure of the manufacturer was used without modification. Briefly, 25 µl of the medium, along with a serial dilution of $PGE_2$ standard samples, were mixed with appropriate amounts of acetylcholinesterase-labeled tracer and $PGE_2$ antiserum, and incubated at room temperature for 18 h. After the wells were emptied and rinsed with wash buffer, 200 µl of Ellman's reagent containing substrate for acetylcholinesterase were added. The reaction was maintained on a slow shaker at room temperature for 1 h and the absorbance at 415 nm was determined in a Bio-Tek Instruments (Model #Elx800, Winooski, Vt.) ELISA plate reader. The $PGE_2$ concentration was represented as picograms per ml. The manufacturer's specifications for this assay include an intra-assay coefficient of variation of <10%, cross reactivity with $PGD_2$ and $PGF_2$ of less than 1% and linearity over the range of 10-1000 pg $ml^{-1}$. The median inhibitory concentrations ($IC_{50}$) for $PGE_2$ synthesis from both COX-2 and COX-1 were calculated as described below.

Calculations—The median inhibitory concentrations ($IC_{50}$) for $PGE_2$ synthesis were calculated using CalcuSyn (BIOSOFT, Ferguson, Mo.). A minimum of four concentrations of each test material or positive control was used for computation. This statistical package performs multiple drug dose-effect calculations using the Median Effect methods described by T. C Chou and P. Talalay [Chou, T. C. and P. Talalay. Quantitative analysis of dose-effect relationships; the combined effects of multiple drugs or enzyme inhibitors. Adv Enzyme Regul 22: 27-55, (1984)] and is incorporated herein by reference. Experiments were repeated three times on three different dates. The percent inhibition at each dose was averaged over the three independent experiments and used to calculate the median inhibitory concentrations reported.

Median inhibitory concentrations were ranked into four arbitrary categories: (1) highest anti-inflammatory response for those agents with an $IC_{50}$ values within 0.3 µg/ml of 0.1; (2) high anti-inflammatory response for those agents with an $IC_{50}$ value within 0.7 µg/ml of 1.0; (3) intermediate anti-inflammatory response for those agents with $IC_{50}$ values between 2 and 7 µg/ml; and (4) low anti-inflammatory response for those agents with $IC_{50}$ values greater than 12 μg/ml, the highest concentration tested Results—The aspirin and celecoxib positive controls demonstrated their respective cyclooxygenase selectivity in this model system (Table 9). While aspirin was approximately 1000-fold more selective for COX-1, celecoxib was 114 times more selective for COX-2. All hops materials were COX-2 selective with Rho isoalpha acids and isoalpha acids demonstrating the highest COX-2 selectivity, 363- and 138-fold respectively. Such high COX-2 selectivity combined with low median inhibitory concentrations, has not been previously reported for natural products from other sources. Of the remaining hops derivatives, only the aromahop oil exhibited a marginal COX-2 selectivity of 3-fold. For extrapolating in vitro data to clinical efficacy, it is generally assumed that a COX-2 selectivity of 5-fold or greater indicates the potential for clinically significant protection of gastric mucosa. Under this criterion, beta acids, $CO_2$ hop extract, spent hops $CO_2$/ethanol, tetrahydro isoalpha acids and hexahydro isoalpha acids displayed potentially clinically relevant COX-2 selectivity.

TABLE 9

COX-2 and COX-1 inhibition in RAW 264.7 cells by hop fractions and derivatives

| Test Material | $IC_{50}$ COX-2 [μg/ml] | $IC_{50}$ COX-1 [μg/ml] | COX-1/COX-2 |
|---|---|---|---|
| Rho Isoalpha acids | 0.08 | 29 | 363 |
| Isoalpha acids | 0.13 | 18 | 138 |
| Beta acids | 0.54 | 29 | 54 |
| $CO_2$ hop extract | 0.22 | 6.3 | 29 |
| Alpha acids | 0.26 | 6.2 | 24 |
| Spent hops $CO_2$/Ethanol | 0.88 | 21 | 24 |
| Tetrahydro isoalpha acids | 0.20 | 4.0 | 20 |
| Hexahydro isoalpha acids | 0.29 | 3.0 | 10 |
| Aromahop Oil | 1.6 | 4.1 | 3.0 |
| Positive Controls | | | |
| Aspirin | 1.16 | 0.0009 | 0.0008 |
| Celecoxib | 0.005 | 0.57 | 114 |

Example 5

Lack of Direct $PGE_2$ Inhibition by Reduced Isomerized Alpha Acids or Isomerized Alpha Acids in LPS-Stimulated Raw 264.7 Cells The objective of this study was to assess the ability of the hops derivatives reduced isoalpha acids and isomerized alpha acids to function independently as direct inhibitors of COX-2 mediated $PGE_2$ biosynthesis in the RAW 264.7 cell model of inflammation. The RAW 264.7 cell line as described in Example 4 was used in this example. Equipment, chemicals and reagents, $PGE_2$ assay, and calculations were as described in Example 4.

Test materials—Hops derivatives reduced isoalpha acids and isomerized alpha acids, as described in Table 12, were used. Aspirin, a COX-1 selective positive control, was obtained from Sigma (St. Louis, Mo.).

Cell culture and treatment with test material—RAW 264.7 cells (TIB-71) were obtained from the American Type Culture Collection (Manassas, Va.) and sub-cultured as described in Example 4. Following overnight incubation at 37° C. with 5% $CO_2$, the growth medium was aspirated and replaced with 200 μl DMEM without FBS or penicillin/streptomycin. RAW 264.7 cells were stimulated with LPS and incubated overnight to induce COX-2 expression. Eighteen hours post LPS-stimulation, test materials were added followed 60 minutes later by the addition of the calcium ionophore A23187. Test materials were dissolved in DMSO as a 250-fold stock solution. Four μl of this 250-fold stock test material preparation was added to 1 ml of DMEM and 200 μl of this solution was subsequently added to eight wells for each dose of test material. Supernatant media was sampled for $PGE_2$ determination after 30 minutes. Median inhibitory concentrations were computed from a minimum of four concentrations over two independent experiments as described in Example 4.

Determination of $PGE_2$—A commercial, non-radioactive procedure for quantification of $PGE_2$ was employed (Caymen Chemical, Ann Arbor, Mich.) for the determination of $PGE_2$ and the recommended procedure of the manufacturer was used without modification as described in Example 4.

Cell viability—Cell viability was assessed by microscopic inspection of cells prior to or immediately following sampling of the medium for $PGE_2$ assay. No apparent cell mortality was noted at any of the concentrations tested.

Calculations—Four concentrations 0.10, 1.0, 10 and 100 μg/ml were used to derive dose-response curves and compute medium inhibitory concentrations ($IC_{50s}$) with 95% confidence intervals using CalcuSyn (BIOSOFT, Ferguson, Mo.).

Results—LPS-stimulation of $PGE_2$ production in RAW 264.7 cells ranged from 1.4-fold to 2.1-fold relative to non-stimulated cells. The $IC_{50}$ value of 8.7 μg/ml (95% CL=3.9-19) computed for the aspirin positive control was consistent with published values for direct COX-2 inhibition ranging from 1.4 to 50 μg/ml [Warner, T. D. et al. Nonsteroidal drug selectivities for cyclo-oxygenase-1 rather than cyclo-oxygenase-2 are associated with human gastrointestinal toxicity: A full in vitro analysis. *Proc. Natl. Acad. Sci. USA* 96:7563-7568, (1999)] and historical data of this laboratory of 3.2 μg/ml (95% CL=0.55-19) in the A549 c line.

When added following COX-2 induction in RAW 264.7 cells by LPS, both RIAA and IAA produced only modest, dose-related inhibition of $PGE_2$. Over the 1000-fold increase in concentration of test material, only a 14 and 10 percent increase in inhibition was noted, respectively, for RIAA and IAA. The shallowness of the dose-response slopes resulted in $IC_{50}$ values (Table 10) in the mg/ml range for RIAA (36 mg/ml) and IAA (>1000 mg/ml). The minimal changes observed in response over three-log units of doses suggests that the observed $PGE_2$ inhibitory effect of the hops derivatives in this cell-based assay may be a secondary effect on the cells and not a direct inhibition of COX-2 enzyme activity.

Figure 4:
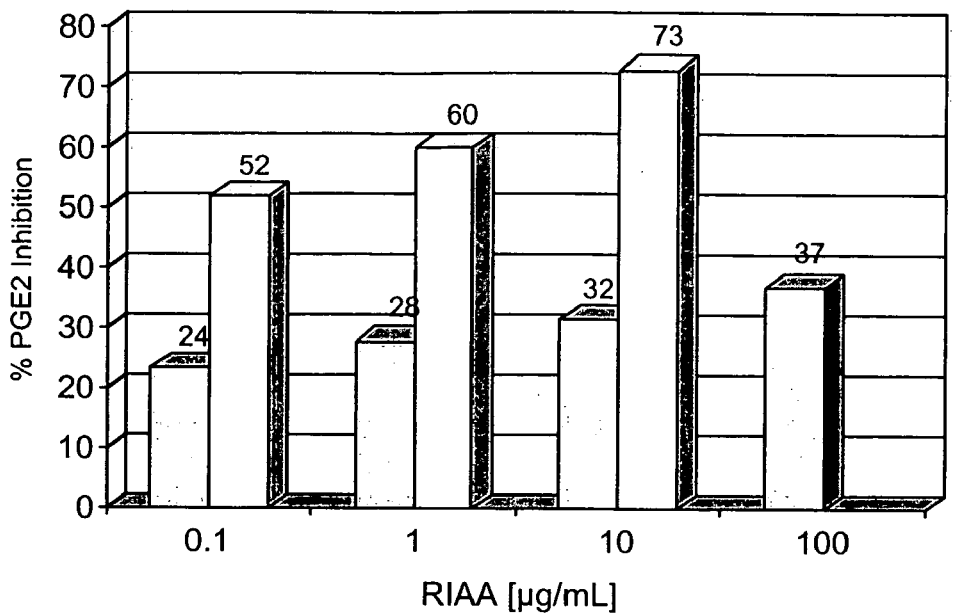
FIG. 4 depicts RIAA [panel A] and IAA [panel B] dose-related inhibition of $PGE_2$ biosynthesis when added before LPS stimulation of COX-2 expression (white bars) or following overnight LPS-stimulation prior to the addition of test material (grey bars).
Figure 4:
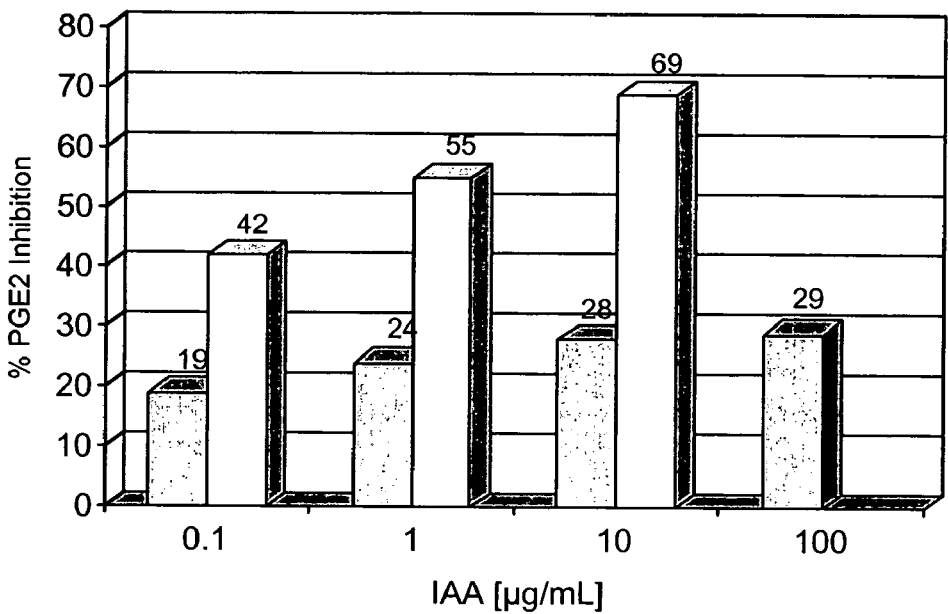

FIGS. 4A and 4B depict the dose-response data respectively, for RIAA and IAA as white bars and the dose-response data from this example as gray bars. The effect of sequence of addition is clearly seen and supports the inference that IAAA and IAA are not direct COX-2 enzyme inhibitors.

It appears that (1) hop materials were among the most active, anti-inflammatory natural products tested as assessed by their ability to inhibit $PGE_2$ biosynthesis in vitro; (2) RIAA and IAA do not appear to be direct COX-2 enzyme inhibitors based on their pattern of inhibition with respect to COX-2 induction; and (3) RIAA and IAA have a COX-2 selectivity that appears to be based on inhibition of COX-2 expression, not COX-2 enzyme inhibition. This selectivity differs from celecoxib, whose selectivity is based on differential enzyme inhibition.

TABLE 10

Median inhibitory concentrations for RIAA, IAA in RAW 264.7 cells when test material is added post overnight LPS-stimulation.

| | $IC_{50}$ [μg/ml] | 95% Confidence Interval [μg/ml] |
|---|---|---|
| Test Material | | |
| RIAA | 36,000 | 17,000–79,000 |
| IAA | >1,000,000 | — |
| Positive Control | | |
| Aspirin | 8.7 μg/ml | 3.9–19 |

RAW 264.7 cells were stimulated with LPS and incubated overnight to induce COX-2 expression. Eighteen hours post LPS-stimulation, test material was added followed 60 minutes later by the addition of A23187. Supernatant media was sampled for $PGE_2$ determination after 30 minutes. Median inhibitory concentrations were computed from a minimum of eight replicates at four concentrations over two independent experiments.

Example 6

Hops Compounds and Derivatives are Not Direct Cyclooxygenase Enzyme Inhibitors in A549 Pulmonary Epithelial Cells Chemicals—Hops and hops derivatives used in this example were previously described in Example 4. All other chemicals were obtained from suppliers as described in Example 4.

Equipment, $PGE_2$ assay, and Calculations were as described in Example 4.

Cells—A549 (human pulmonary epithelial) cells were obtained from the American Type Culture Collection (Manassas, Va.) and sub-cultured according to the instructions of the supplier. The cells were routinely cultured at 37° C. with 5% $CO_2$ in RPMI 1640 containing 10% FBS, with 50 units penicillin/ml, 50 μg streptomycin/ml, 5 mM sodium pyruvate, and 5 mM L-glutamine. On the day of the experiments, exponentially growing cells were harvested and washed with serum-free RPMI 1640.

Log phase A549 cells were plated at $8 \times 10^4$ cells per well in 0.2 ml growth medium per well in a 96-well tissue culture plate. For the determination of $PGE_2$ inhibition by the test compounds, the procedure of Warner, et al. [Nonsteroid drug selectivities for cyclo-oxygenase-1 rather than cyclo-oxygenase-2 are associated with human gastrointestinal toxicity: a full in vitro analysis. Proc Natl Acad Sci U S A 96, 7563-7568, (1999)], also known as the WHMA-COX-2 protocol was followed with no modification. Briefly, 24 hours after plating of the A549 cells, interleukin-1β (10 ng/ml) was added to induce the expression of COX-2. After 24 hr, the cells were washed with serum-free RPMI 1640. Subsequently, the test materials, dissolved in DMSO and serum-free RPMI, were added to the wells to achieve final concentrations of 25, 5.0, 0.5 and 0.05 μg/ml. Each concentration was run in duplicate. DMSO was added to the control wells in an equal volume to that contained in the test wells. Sixty minutes later, A23187 (50 μM) was added to the wells to release arachadonic acid. Twenty-five μl of media were sampled from the wells 30 minutes later for $PGE_2$ determination.

Cell viability was assessed visually and no apparent toxicity was observed at the highest concentrations tested for any of the compounds. $PGE_2$ in the supernatant medium was determined and reported as previously described in Example 4. The median inhibitory concentration ($IC_{50}$) for $PGE_2$ synthesis was calculated as previously described in Example 4.

Results—At the doses tested, the experimental protocol failed to capture a median effective concentration for any of the hops extracts or derivatives. Since the protocol requires the stimulation of COX-2 expression prior to the addition of the test compounds, it is believed that the failure of the test materials to inhibit $PGE_2$ synthesis is that their mechanism of action is to inhibit the expression of the COX-2 isozyme and not activity directly. While some direct inhibition was observed using the WHMA-COX-2 protocol, this procedure appears inappropriate in evaluating the anti-inflammatory properties of hops compounds or derivatives of hops compounds.

Example 7

Hops Derivatives Inhibit Mite Dust Allergen Activation of $PGE_2$ Biosynthesis in A549 Pulmonary Epithelial Cells Chemicals—Hops and hops derivatives, (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), and (7) tetrahop (tetrahydro-iso-alpha acids THIAA), used in this example were previously described in Example 1. All other chemicals were obtained from suppliers as described in Example 4. Test materials at a final concentration of 10 μg/ml were added 60 minutes prior to the addition of the mite dust allergen.

Equipment, $PGE_2$ assay, and Calculations were as described in Example 4.

Mite dust allergen isolation—*Dermatophagoides farinae* is the American house dust mite. *D. farinae* were raised on a 1:1 ratio of Purina Laboratory Chow (Ralston Purina, Co, St. Louis, Mo.) and Fleischmann's granulated dry yeast (Standard Brands, Inc. New York, N.Y.) at room temperature and 75% humidity. Live mites were aspirated from the culture container as they migrated from the medium, killed by freezing, desiccated and stored at 0% humidity. The allergenic component of the mite dust was extracted with water at ambient temperature. Five-hundred mg of mite powder were added to 5 ml of water (1:10 w/v) in a 15 ml conical centrifuge tube (VWR, Rochester, N.Y.), shaken for one minute and allowed to stand overnight at ambient temperature. The next day, the aqueous phase was filtered using a 0.2 μm disposable syringe filter (Nalgene, Rochester, N.Y.). The filtrate was termed mite dust allergen and used to test for induction of $PGE_2$ biosynthesis in A549 pulmonary epithelial cells.

Cell culture and treatment—The human airway epithelial cell line, A549 (American Type Culture Collection, Bethesda, Md.) was cultured and treated as previously described in Example 6. Mite allergen was added to the culture medium to achieve a final concentration of 1000 ng/ml. Eighteen hours later, the media were sampled for $PGE_2$ determination.

Results—Table 11 depicts the extent of inhibition by hops derivatives of $PGE_2$ biosynthesis in A549 pulmonary cells stimulated by mite dust allergen. All hops derivatives tested were capable of significantly inhibiting the stimulatory effects of mite dust allergens.

TABLE 11

PGE$_2$ inhibition by hops derivatives in A549 pulmonary epithelial cells stimulated by mite dust allergen.

| Test Material | Percent PGE$_2$ Inhibition |
|---|---|
| Alpha hop (AA) | 81 |
| Aromahop OE | 84 |
| Isohop (IAA) | 78 |
| Beta acids (BA) | 83 |
| Hexahop (HHIAA) | 82 |
| Redihop (RIAA) | 81 |
| Tetrahop (THIAA) | 76 |

This example illustrates that hops derivatives are capable of inhibiting the PGE$_2$ stimulatory effects of mite dust allergens in A549 pulmonary cells.

Example 8

Lack of Direct COX-2 Inhibition by Reduced Isoalpha Acids

The objective of this example was to determine whether magnesium reduced isoalpha acids can act as a direct inhibitor of COX-2 enzymatic activity.

Materials—Test compounds were prepared in dimethyl sulfoxide (DMSO) and stored at −20° C. LPS was purchased from Sigma-Aldrich (St. Louis, Mo.). MgRIAA was supplied by Metagenics (San Clemente, Calif.), and the commercial formulation of celecoxib was used (Celebrex™, Searle & Co., Chicago, Ill.).

Cell Culture—The murine macrophage RAW 264.7 cell line was purchased from ATCC (Manassas, Va.) and maintained according to their instructions. Cells were subcultured in 96-well plates at a density of 8×10$^4$ cells per well and allowed to reach 90% confluence, approximately 2 days. LPS (1 μg/ml) or PBS alone was added to the cell media and incubated for 12 hrs. The media was removed from the wells and LPS (1 μg/ml) with the test compounds dissolved in DMSO and serum-free RPMI, were added to the wells to achieve final concentrations of MgRIAA at 20, 5.0, 1.0 and 0.1 μg/ml and celecoxib at 100, 10, 1 and 0.1 ng/ml. Each concentration was run in 8 duplicates. Following 1 hr of incubation with the test compounds, the cell media were removed and replaced with fresh media with test compounds with LPS (1 μg/ml) and incubated for 1 hr. The media were removed from the wells and analyzed for the PGE$_2$ synthesis.

PGE$_2$ assay—A commercial, non-radioactive procedure for quantification of PGE$_2$ was employed (Cayman Chemical, Ann Arbor, Mich.). Samples were diluted 10 times in EIA buffer and the recommended procedure of the manufacturer was used without modification. The PGE$_2$ concentration was represented as picograms per ml. The manufacturer's specifications for this assay. include an intra-assay coefficient of variation of <10%, cross reactivity with PGD$_2$ and PGF$_2$ of less than 1% and linearity over the range of 10-1000 pg ml$^{-1}$.

Figure 5:
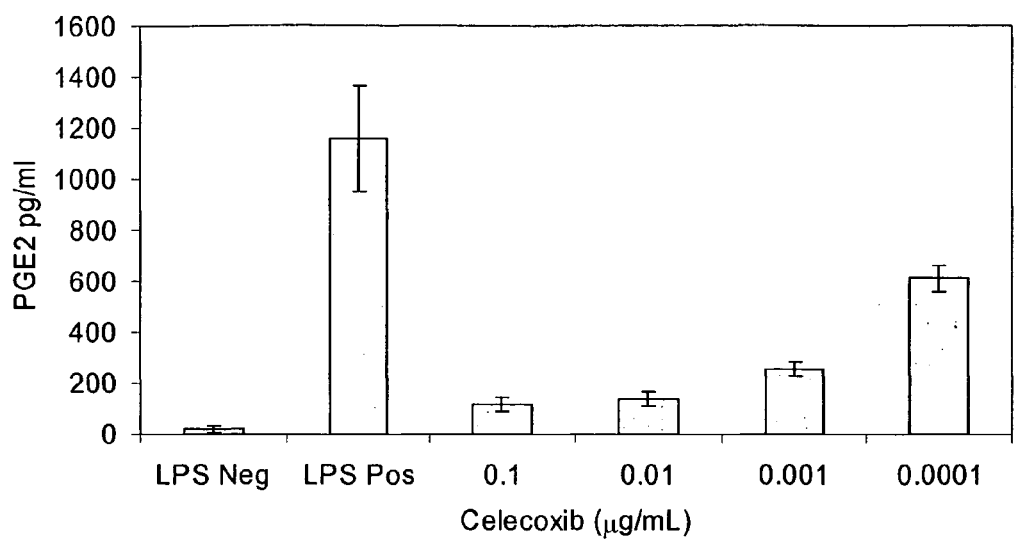
FIG. 5 provides a graphic representation of direct enzymatic inhibition of celecoxib [panel A] and MgRIAA [panel B] on LPS induced COX-2 mediated $PGE_2$ production analyzed in RAW 264.7 cells. $PGE_2$ was measured and expressed in pg/ml. The error bars represent the standard deviation (n=8).
Figure 5:
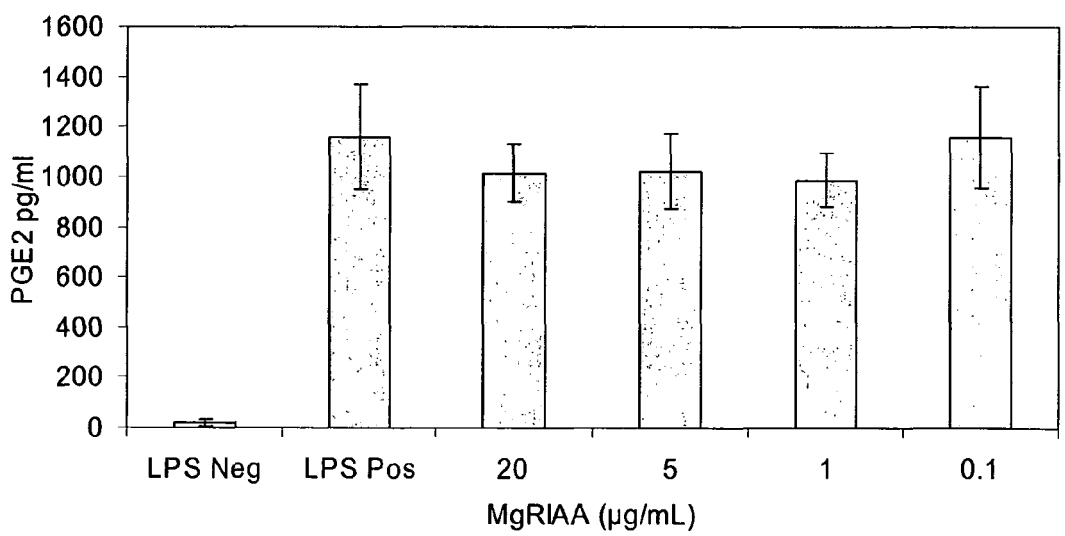

COX-2 specific inhibitor celecoxib dose-dependently inhibited COX-2 mediated PGE$_2$ synthesis (100, 10, 1 and 0.1 ng/ml) while no significant PGE$_2$ inhibition was observed with MgRIAA. The data suggest that MgRIAA is not a direct COX-2 enzymatic inhibitor like celocoxib (FIG. 5)

Example 9

Inhibition of iNOS and COX-2 Protein Expression by MgRIAA

Cellular extracts from RAW 264.7 cells treated with MgRIAA and stimulated with LPS were assayed for iNOS and COX-2 protein by Western blot.

Materials—Test compounds were prepared in dimethyl sulfoxide (DMSO) and stored at −20° C. MgRIAA was supplied by Metagenics (San Clemente, Calif.). Parthenolide was purchased from Sigma-Aldrich (St. Louis, Mo.). The PI3K inhibitors wortmannin and LY294002 were purchased from EMD Biosciences (San Diego, Calif.). Antibodies generated against COX-2 and iNOS were purchased from Cayman Chemical (Ann Arbor, Mich.). Antibodies generated against GAPDH were purchased from Novus Biological (Littleton, Colo.). Secondary antibodies coupled to horseradish peroxidase were purchased from Amersham Biosciences (Piscataway, N.J.).

Cell Culture—The murine macrophage RAW 264.7 cell line was purchased from ATCC (Manassas, Va.) and maintained according to their instructions. Cells were grown and subcultured in 24-well plates at a density of 3×10$^5$ cells per well and allowed to reach 90% confluence, approximately 2 days. Test compounds were added to the cells in serum free medium at a final concentration of 0.4% DMSO. Following 1 hr of incubation with the test compounds, LPS (1 μg/ml) or phosphate buffered saline alone was added to the cell wells and incubation continued for the indicated times.

Western Blot—Cell extracts were prepared in Buffer E (50 mM HEPES, pH 7.0; 150 mM NaCl; 1% triton X-100; 1 mM sodium orthovanadate; aprotinin 5 μg/ml; pepstatin A 1 μg/ml; leupeptin 5 μg/ml; phenylmethanesulfonyl fluoride 1 mM). Briefly, cells were washed twice with cold PBS and Buffer E was added. Cells were scraped into a clean tube, following a centrifugation at 14,000 rpm for 10 minutes at 4° C., the supernatant was taken as total cell extract. Cell extracts (50 μg) were electrophoresed through a pre-cast 4%-20% Tris-HCl Criterion gel (Bio-Rad, Hercules, Calif.) until the front migration dye reached 5 mm from the bottom of the gel. The proteins were transferred to nitrocellulose membrane using a semi-dry system from Bio-Rad (Hercules, Calif.). The membrane was washed and blocked with 5% dried milk powder for 1 hour at room temperature. Incubation with the primary antibody followed by the secondary antibody was each for one hour at room temperature. Chemiluminescence was performed using the SuperSignal West Femto Maximum Sensitivity Substrate from Pierce Biotechnology (Rockford, Ill.) by incubation of equal volume of luminol/enhancer solution and stable peroxide solution for 5 minutes at room temperature. The Western blot image was captured using a cooled CCD Kodak® (Rochester, N.Y.) IS1000 imaging system. Densitometry was performed using Kodak® software.

Figure 6:
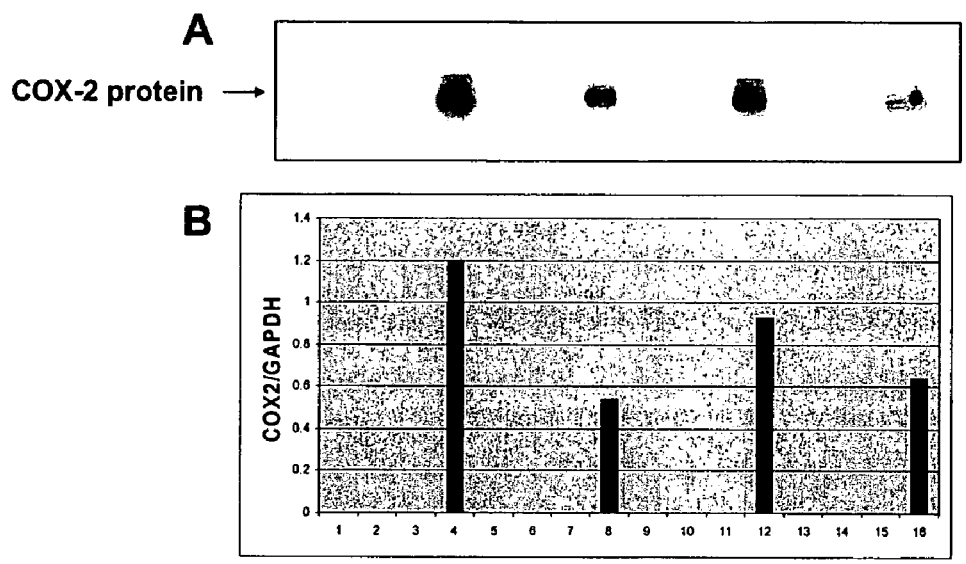
FIG. 6 provides Western blot detection of COX-2 protein expression. RAW 264.7 cells were stimulated with LPS for the indicated times, after which total cell extract was visualized by western blot for COX-2 and GAPDH expression [panel A]. Densitometry of the COX-2 and GAPDH bands was performed. The graph [panel B] represents the ratio of COX-2 to GAPDH.
Figure 7:
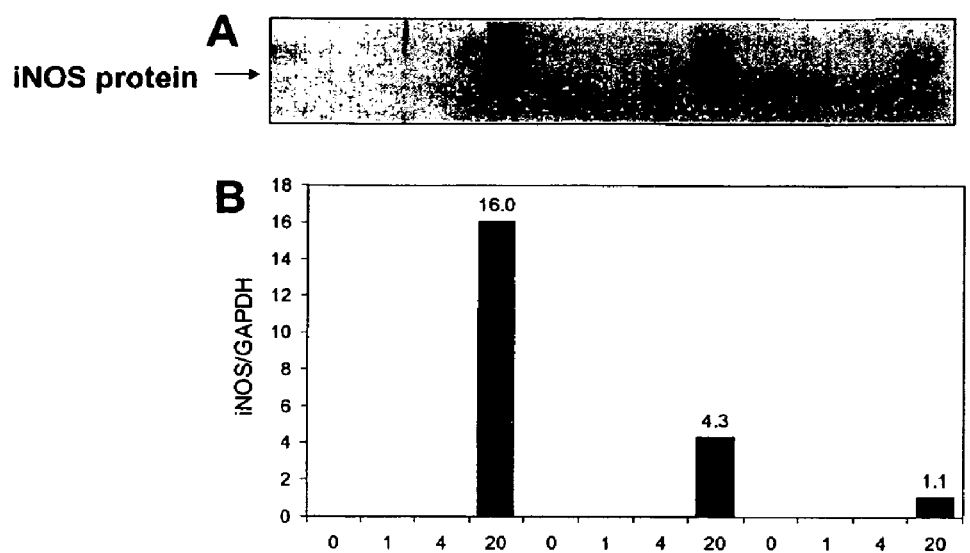
FIG. 7 provides Western blot detection of iNOS protein expression. RAW 264.7 cells were stimulated with LPS for the indicated times, after which total cell extract was visualized by western blot for iNOS and GAPDH expression [panel A]. Densitometry of the iNOS and GAPDH bands was performed. The graph [panel B] represents the ratio of iNOS to GAPDH.

The percent of COX-2 and iNOS protein expression was assessed using Western blot detection. The expression of COX-2 was observed after 20 hours stimulation with LPS. As compared to the solvent control of DMSO, a reduction of 55% was seen in COX-2 protein expression by MgRIAA (FIG. 6). A specific NF-kB inhibitor parthenolide, inhibited protein expression 22.5%, while the PI3-kinase inhibitor decreased COX-2 expression about 47% (FIG. 6). Additionally, a reduction of 73% of iNOS protein expression was observed after 20 hr stimulation with LPS (FIG. 7) by MgRIAA.

Example 10

NF-κB Nuclear Translocation and DNA Binding

Nuclear extracts from RAW 264.7 cells treated with MgRIAA and stimulated with LPS for 4 hours were assayed for NF-κB binding to DNA.

Materials—Test compounds were prepared in dimethyl sulfoxide (DMSO) and stored at −20° C. MgRIAA was supplied by Metagenics (San Clemente, Calif.). Parthenolide, a specific inhibitor for NF-kB activation was purchased from Sigma-Aldrich (St. Louis, Mo.). The PI3K inhibitor LY294002 was purchased from EMD Biosciences (San Diego, Calif.).

Cell Culture—The murine macrophage RAW 264.7 cell line was purchased from ATCC (Manassas, Va.) and maintained according to their instructions. Cells were subcultured in 6-well plates at a density of $1.5 \times 10^6$ cells per well and allowed to reach 90% confluence, approximately 2 days. Test compounds MgRIAA (55 and 14 µg/ml), parthenolide (80 µM) and LY294002 (25 µM) were added to the cells in serum free media at a final concentration of 0.4% DMSO. Following 1 hr of incubation with the test compounds, LPS (1 µg/ml) or PBS alone was added to the cell media and incubation continued for an additional four hours.

Figure 8:
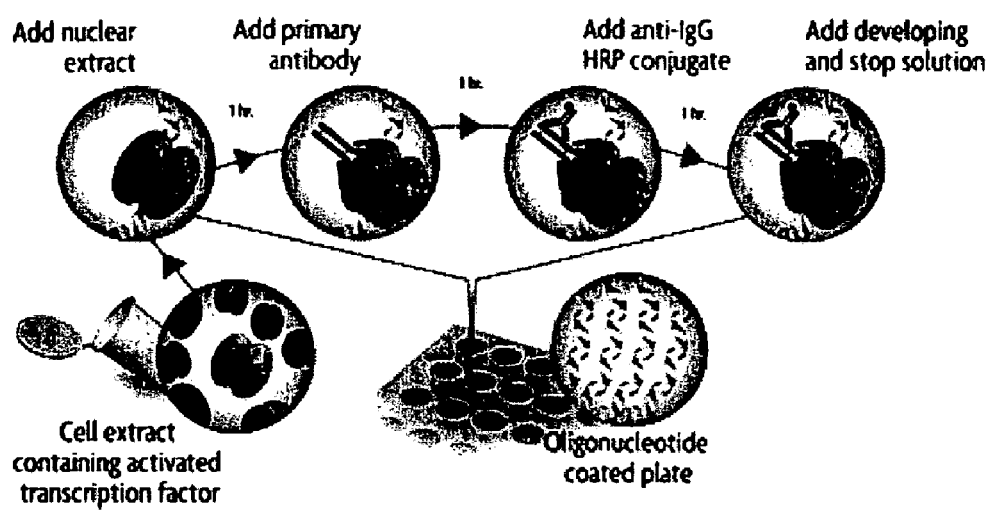
FIG. 8 provides a representative schematic of the TransAM NF-κB kit utilizing a 96-well format. The oligonucleotide bound to the plate contains the consensus binding site for NF-κB. The primary antibody detected the p50 subunit of NF-κB.

NF-κB-DNA binding—Nuclear extracts were prepared essentially as described by Dignam, et al [Nucl Acids Res 11:1475-1489, (1983)]. Briefly, cells were washed twice with cold PBS, then Buffer A (10 mM HEPES, pH 7.0; 1.5 mM $MgCl_2$; 10 mM KCl; 0.1% NP-40; aprotinin 5 µg/ml; pepstatin A 1 µg/ml; leupeptin 5 µg/ml; phenylmethanesulfonyl fluoride 1 mM) was added and allowed to sit on ice for 15 minutes. Cells were then scraped into a clean tube and processed through three cycles of freeze/thaw. The supernatant layer following centrifugation at 10,000×g for 5 min at 4° C. was the cytoplasmic fraction. The remaining pellet was resuspended in Buffer C (20 mM HEPES, pH 7.0; 1.5 mM KCl; 420 mM KCl; 25% glycerol; 0.2 M EDTA; aprotinin 5 µg/ml; pepstatin A 1 µg/ml; leupeptin 5 µg/ml; phenylmethanesulfonyl fluoride 1 mM) and allowed to sit on ice for 15 minutes. The nuclear extract fraction was collected as the supernatant layer following centrifugation at 10,000×g for 5 min at 4° C. NF-kB DNA binding of the nuclear extracts was assessed using the TransAM NF-κB kit from Active Motif (Carlsbad, Calif.) as per manufacturer's instructions. As seen in FIG. 8, the TransAM kit detected the p50 subunit of NF-κB binding to the consensus sequence in a 96-well format. Protein concentration was measured (Bio-Rad assay) and 10 µg of nuclear protein extracts were assayed in duplicate.

Figure 9:
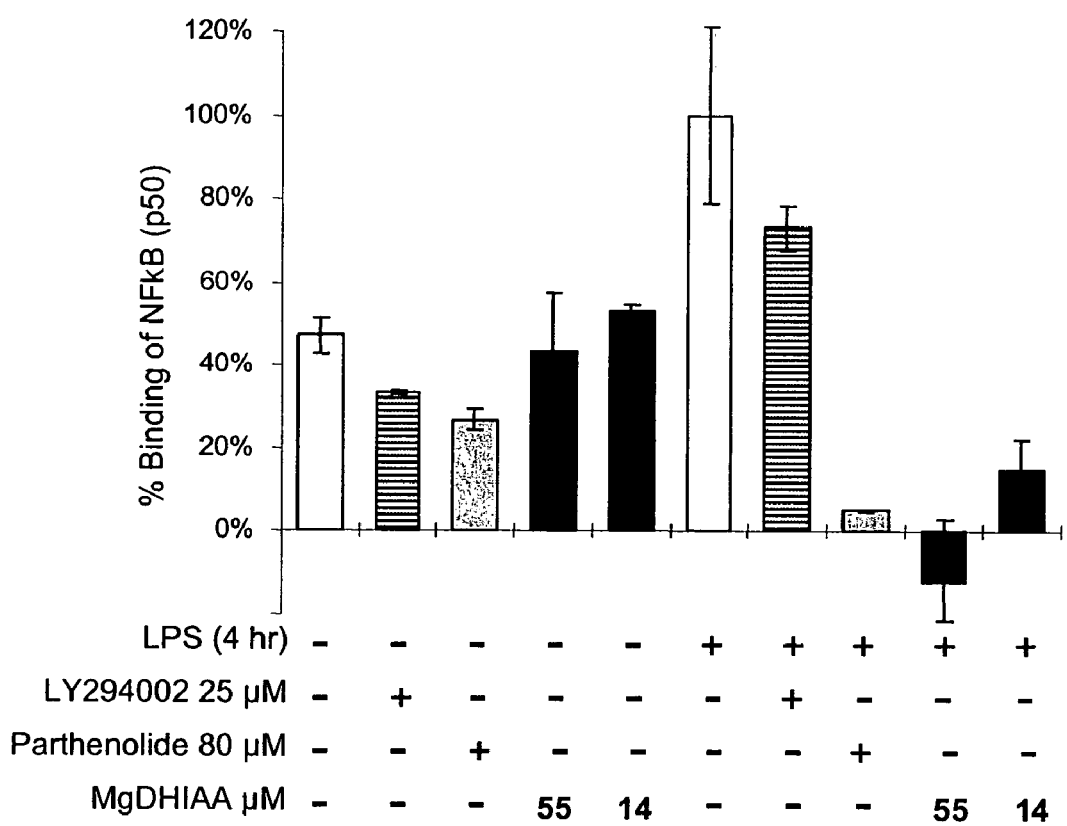
FIG. 9 provides representative binding activity of NF-κB as determined by the TransAM NF-κB kit. The percent of DNA binding was calculated relative to the LPS control (100%). The error bars represent the standard deviation (n=2). RAW 264.7 cells were treated with test compounds and LPS for 4 hr as described in the Examples section.

Analysis of nuclear extracts (10 µg protein) was performed in duplicate and the results are presented graphically in FIG. 9. Stimulation with LPS (1 µg/ml) resulted in a two-fold increase in NF-κB DNA binding. Treatment with LY294002 (a PI3 kinase inhibitor) resulted in a modest decrease of NF-κB binding as expected from previous literature reports. Parthenolide also resulted in a significant reduction in NF-κB binding as expected. A large reduction of NF-κB binding was observed with MgRIAA. The effect was observed in a dose-response manner. The reduction in NF-κB binding may result in reduced transcriptional activation of target genes, including COX-2, iNOS and TNFα.

The results suggest that the decreased NF-κB binding observed with MgDHIAA may result in decreased COX-2 protein expression, ultimately leading to a decrease in $PGE_2$ production.

Example 11

Increased Lipogenesis in 3T3-L1 Adipocytes Elicited by a Dimethyl Sulfoxide-Soluble Fraction of an Aqueous Extract of *Acacia* Bark The Model—The 3T3-L1 murine fibroblast model is used to study the potential effects of compounds on adipocyte differentiation and adipogenesis. This cell line allows investigation of stimuli and mechanisms that regulate preadipocytes replication separately from those that regulate differentiation to adipocytes [Fasshauer, M., Klein, J., Neumann, S., Eszlinger, M., and Paschke, R. Hormonal regulation of adiponectin gene expression in 3T3-L1 adipocytes. Biochem Biophys Res Commun, 290: 1084-1089, (2002); Li, Y. and Lazar, M. A. Differential gene regulation by PPARgamma agonist and constitutively active PPARgamma2. Mol Endocrinol, 16: 1040-1048, (2002)] as well as insulin-sensitizing and triglyceride-lowering ability of the test agent [Raz, I., Eldor, R., Cemea, S., and Shafrir, E. Diabetes: insulin resistance and derangements in lipid metabolism. Cure through intervention in fat transport and storage. Diabetes Metab Res Rev, 21: 3-14, (2005)].

As preadipocytes, 3T3-L1 cells have a fibroblastic appearance. They replicate in culture until they form a confluent monolayer, after which cell-cell contact triggers $G_0/G_1$ growth arrest. Terminal differentiation of 3T3-L1 cells to adipocytes depends on proliferation of both pre- and post-confluent preadipocytes. Subsequent stimulation with 3-isobutyl-1-methylxanthane, dexamethasone, and high does of insulin (MDI) for two days prompts these cells to undergo post-confluent mitotic clonal expansion, exit the cell cycle, and begin to express adipocyte-specific genes. Approximately five days after induction of differentiation, more than 90% of the cells display the characteristic lipid-filled adipocyte phenotype. Assessing triglyceride synthesis of 3T3-L1 cells provides a validated model of the insulin-sensitizing ability of the test agent It appears paradoxical that an agent that promotes lipid uptake in fat cells should improve insulin sensitivity. Several hypotheses have been proposed in an attempt to explain this contradiction. One premise that has continued to gain research support is the concept of "fatty acid steal" or the incorporation of fatty acids into the adipocyte from the plasma causing a relative depletion of fatty acids in the muscle with a concomitant improvement of glucose uptake [Martin, G., K. Schoonjans, et al. PPARgamma activators improve glucose homeostasis by stimulating fatty acid uptake in the adipocytes. Atherosclerosis 137 Suppl: S75-80, (1998)]. Thiazolidinediones, such as troglitazone and pioglitazone, have been shown to selectively stimulate lipogenic activities in fat cells resulting in greater insulin suppression of lipolysis or release of fatty acids into the plasma [Yamauchi, T., J. Kamon, et al. The mechanisms by which both heterozygous peroxisome proliferator-activated receptor gamma (PPARgamma) deficiency and PPARgamma agonist improve insulin resistance. J Biol Chem 276(44): 41245-54, (2001); Oakes, N. D., P. G. Thalen, et al. Thiazolidinediones increase plasma-adipose tissue FFA exchange capacity and enhance insulin-mediated control of systemic FFA availability. Diabetes 50(5): 1158-65, (2001)]. This action would leave less free fatty acids available for other tissues [Yang, W. S., W. J. Lee, et al. Weight reduction increases plasma levels of an adipose-derived anti-inflammatory protein, adiponectin. J Clin Endocrinol Metab 86(8): 3815-9, (2001)]. Thus, insulin desensitizing effects of free fatty acids in muscle and liver would be reduced as a consequence of thiazolidinedione treatment. These in vitro results have been confirmed clinically [Boden, G. Role of fatty acids in the pathogenesis of insulin resistance and NIDDM. Diabetes 46(1): 3-10, (1997); Stumvoll, M. and H. U. Haring Glitazones: clinical effects and molecular mechanisms. Ann Med 34(3): 217-24, (2002)].

Test Materials—Troglitazone was obtained from Cayman Chemicals (Ann Arbor, Mich., while methylisobutylxanthine, dexamethasone, indomethacin, Oil red O and insulin were obtained from Sigma (St. Louis, Mo.). The test material was a dark brown powder produced from a 50:50 (v/v) water/ alcohol extract of the gum resin of *Acacia* (AcE) sample #4909 and was obtained from Bayir Chemicals (No. 68, South Cross Road, Basavanagudi, India). The extract was standardized to contain not less than 20% apecatechin. Batch No. A Cat/2304 used in this example contained 20.8% apecatechin as determined by UV analysis. Penicillin, streptomycin, Dulbecco's modified Eagle's medium (DMEM) was from Mediatech (Hemdon, Va.) and 10% FBS-HI (fetal bovine serum-heat inactivated) from Mediatech and Hyclone (Logan, Utah). All other standard reagents, unless otherwise indicted, were purchased from Sigma.

Cell culture and Treatment—The murine fibroblast cell line 3T3-L1 was purchased from the American Type Culture Collection (Manassas, Va.) and sub-cultured according to instructions from the supplier. Prior to experiments, cells were cultured in DMEM containing 10% FBS-HI added 50 units penicillin/ml and 50 µg streptomycin/ml, and maintained in log phase prior to experimental setup. Cells were grown in a 5% $CO_2$ humidified incubator at 37° C. Components of the pre-confluent medium included (1) 10% FBS/DMEM containing 4.5 g glucose/L; (2) 50 U/ml penicillin; and (3) 50 µg/ml streptomycin. Growth medium was made by adding 50 ml of heat inactivated FBS and 5 ml of penicillin/streptomycin to 500 ml DMEM. This medium was stored at 4° C. Before use, the medium was warmed to 37° C. in a water bath.

3T3-T1 cells were seeded at an initial density of $6 \times 10^4$ cells/$cm^2$ in 24-well plates. For two days, the cells were allowed grow to reach confluence. Following confluence, the cells were forced to differentiate into adipocytes by the addition of differentiation medium; this medium consisted of (1) 10% FBS/DMEM (high glucose); (2) 0.5 mM methylisobutylxanthine; (3) 0.5 µM dexamethasone and (4) 10 µg/ml insulin (MDI medium). After three days, the medium was changed to post-differentiation medium consisting of 10 µg/ml insulin in 10% FBS/DMEM.

Figure 10:
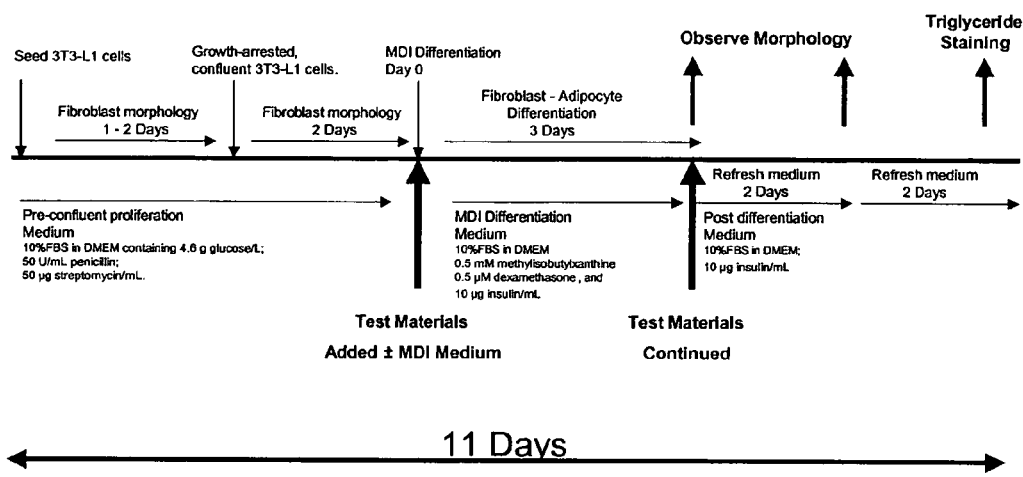
FIG. 10 is a schematic of a representative testing procedure for assessing the lipogenic effect of an *Acacia* sample #4909 extract on developing and mature adipocytes. The 3T3-L1 murine fibroblast model was used to study the potential effects of the test compounds on adipocyte adipogenesis.

AcE was partially dissolved in dimethyl sulfoxide (DMSO) and added to the culture medium to achieve a concentration of 50 µg/ml at Day 0 of differentiation and throughout the maturation phase (Days 6 or 7 (D6/7)). Whenever fresh media were added, fresh test material was also added. DMSO was chosen for its polarity and the fact that it is miscible with the aqueous cell culture media. As positive controls, indomethacin and troglitazone were added, respectively, to achieve final concentrations of 5.0 and 4.4 µg/ml. Differentiated, D6/D7 3T3-L1 cells were stained with 0.36% Oil Red 0 or 0.001% BODIPY. The complete procedure for differentiation and treatment of cells with test materials is outlined schematically in FIG. 10.

Oil Red O Staining—Triglyceride content of D6/D7-differentiated 3T3-L1 cells was estimated with Oil Red O according to the method of Kasturi and Joshi [Kasturi, R. and Joshi, V. C. Hormonal regulation of stearoyl coenzyme A desaturase activity and lipogenesis during adipose conversion of 3T3-L1 cells. J Biol Chem, 257: 12224-12230, 1982]. Monolayer cells were washed with PBS (phosphate buffered saline, Mediatech) and fixed with 10% formaldehyde for ten minutes. Fixed cells were stained with an Oil Red O working solution of three parts 0.6% Oil Red O/isopropanol stock solution and two parts water for one hour and the excess stain was washed once with water. The resulting stained oil droplets were extracted from the cells with isopropanol and quantified by spectrophotometric analysis at 540 nm (MEL312e BIO-KINETICS READER, Bio-Tek Instruments, Winooski, Vt.). Results for test materials and the positive controls indomethacin and troglitazone were represented relative to the 540 nm absorbance of the solvent controls.

BODIPY Staining—4,4-Difluoro-1,3,5,7,8-penta-methyl-4-bora-3a,4a-diaza-s-indacene (BODIPY 493/503; Molecular Probes, Eugene, Oreg.) was used for quantification of cellular neutral and nonpolar lipids. Briefly, media were removed and cells were washed once with non-sterile PBS. A stock 1000× BODIPY/DMSO solution was made by dissolving 1 mg BODIPY in 1 ml DMSO (1,000 µg BODIPY/ml). A working BODIPY solution was then made by adding 10 µl of the stock solution to 990 µl PBS for a final BODIPY concentration in the working solution of 0.01 µg/µl. One-hundred µl of this working solution (1 µg BODIPY) was added to each well of a 96-well microtiter plate. After 15 min on an orbital shaker (DS-500, VWR Scientific Products, South Plainfield, N.J.) at ambient temperature, the cells were washed with 100 µl PBS followed by the addition of 100 µl PBS for reading for spectrofluorometric determination of BODIPY incorporation into the cells. A Packard Fluorocount spectrofluorometer (Model#BF1000, Meridan, Conn.) set at 485 nm excitation and 530 nm emission was used for quantification of BODIPY fluorescence. Results for test materials, indomethacin, and troglitazone were reported relative to the fluorescence of the solvent controls.

A chi-square analysis of the relationship between the BODIPY quantification of all neutral and nonpolar lipids and the Oil Red O determination of triglyceride content in 3T3-L1 cells on D7 indicated a significant relationship between the two methods with $p<0.001$ and Odds Ratio of 4.64.

Statistical Calculations and Interpretation—AcE and indomethacin were assayed a minimum of three times in duplicate. Solvent and troglitazone controls were replicated eight times also in duplicate. Nonpolar lipid incorporation was represented relative to the nonpolar lipid accumulation of fully differentiated cells in the solvent controls. A positive response was defined as an increase in lipid accumulation assessed by Oil Red O or BODIPY staining greater than the respective upper 95% confidence interval of the solvent control (one-tail, Excel; Microsoft, Redmond, Wash.). AcE was further characterized as increasing adipogenesis better than or equal to the troglitazone positive control relative to the solvent response; the student t-test function of Excel was used for this evaluation.

Figure 11:
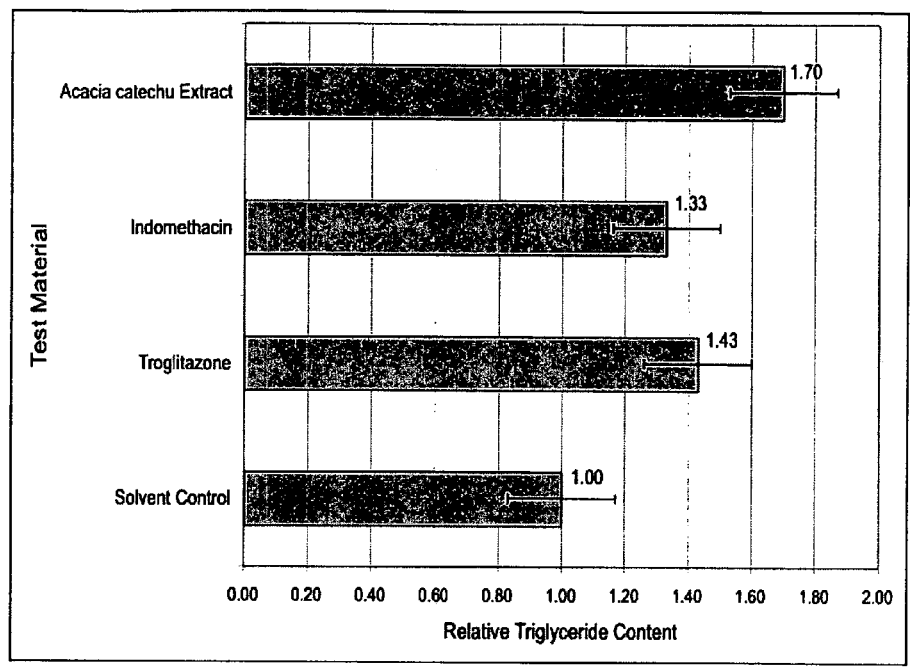
FIG. 11 is a graphic representation depicting the nonpolar lipid content of 3T3-L1 adipocytes treated with an *Acacia* sample #4909 extract or the positive controls indomethacin and troglitazone relative to the solvent control. Error bars represent the 95% confidence limits (one-tail).

Results—The positive controls indomethacin and troglitazone induced lipogenesis to a similar extent in 3T3-L1 cells (FIG. 11). Unexpectedly, the AcE produced an adipogenic response greater than either of the positive controls indomethacin and troglitazone.

The lipogenic potential demonstrated in 3T3-L1 cells, dimethyl sulfoxide-soluble components of an aqueous *Acacia* sample #4909 extract demonstrates a potential to increase insulin sensitivity in humans or other animals exhibiting signs or symptoms of insensitivity to insulin.

Example 12

Increased Adiponectin Secretion from Insulin-Resistant 3T3-L1 Adipocytes Elicited by a Dimethyl Sulfoxide-Soluble Fraction of an Aqueous Extract of *Acacia*

The Model—The 3T3-L1 murine fibroblast model as described in Example 11 was used in these experiments.

Test Materials—Troglitazone was purchased from Cayman Chemical (Ann Arbor, Mich.) while methylisobutylxanthine, dexamethasone, and insulin were obtained from Sigma (St. Louis, Mo.). The test material was a dark brown powder produced from a 50:50 (v/v) water/alcohol extract of the gum resin of *Acacia* sample #4909 and was obtained from Bayir Chemicals (No. 68, South Cross Road, Basavanagudi, India). The extract was standardized to contain not less than 20% apecatechin. Batch No. A Cat/2304 used in this example contained 20.8% apecatechin as determined by UV analysis. Penicillin, streptomycin, Dulbecco's modified Eagle's medium (DMEM) was from Mediatech (Herndon, Va.) and 10% FBS-HI (fetal bovine serum-heat inactivated from Mediatech and Hyclone (Logan, Utah). All other standard reagents, unless otherwise indicted, were purchased from Sigma.

Cell culture and Treatment—Culture of the murine fibroblast cell line 3T3-L1 to produce Day 6 differentiated adipocytes was performed as described in Example 10. 3T3-L1 cells were seeded at an initial density of $1 \times 10^4$ cells/cm$^2$ in 96-well plates. For two days, the cells were allowed grow to reach confluence. Following confluence, the cells were forced to differentiate into adipocytes by the addition of differentiation medium; this medium consisted of (1) 10% FBS/DMEM (high glucose); (2) 0.5 mM methylisobutylxanthine; (3) 0.5 µM dexamethasone and (4) 10 µg/ml insulin (MDI medium). From Day 3 through Day 5, the medium was changed to post-differentiation medium consisting of 10 µg/ml insulin in 10% FBS/DMEM.

Figure 12:
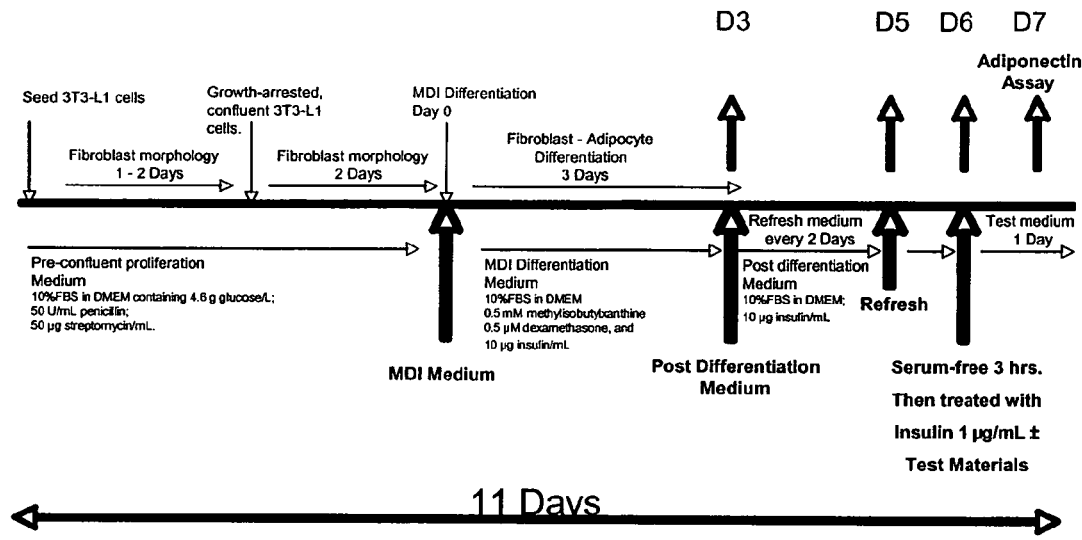
FIG. 12 is a schematic of a representative testing procedure for assessing the effect of a dimethyl sulfoxide-soluble fraction of an aqueous extract of *Acacia* sample #4909 on the secretion of adiponectin from insulin-resistant 3T3-L1 adipocytes.

Assessing the effect of *Acacia* on insulin-resistant, mature 3T3-L1 cells was performed using a modification of the procedure described by Fasshauer et al. [Fasshauer, et al. Hormonal regulation of adiponectin gene expression in 3T3-L1 adipocytes. BBRC 290:1084-1089, (2002)]. Briefly, on Day 6, cells were maintained in serum-free media containing 0.5% bovine serum albumin (BSA) for three hours and then treated with 1 µg insulin/ml plus solvent or insulin plus test material. Troglitazone was dissolved in dimethyl sulfoxide and added to achieve concentrations of 5, 2.5, 1.25 and 0.625 µg/ml. The *Acacia* extract was tested at 50, 25, 12.5 and 6.25 µg/ml. Twenty-four hours later, the supernatant medium was sampled for adiponectin determination. The complete procedure for differentiation and treatment of cells with test materials is outlined schematically in FIG. 12.

Adiponectin Assay—The adiponectin secreted into the medium was quantified using the Mouse Adiponectin Quantikine® Immunoassay kit with no modifications (R&D Systems, Minneapolis, Minn.). Information supplied by the manufacturer indicated that recovery of adiponectin spiked in mouse cell culture media averaged 103% and the minimum detectable adiponectin concentration ranged from 0.001 to 0.007 ng/ml.

Statistical Calculations and Interpretation—All assays were preformed in duplicate. For statistical analysis, the effect of *Acacia* on adiponectin secretion was computed relative to the solvent control. Differences between the doses were determined using the student's t-test without correction for multiple comparisons; the nominal five percent probability of a type I error was selected.

Potency of the test materials was estimated using a. modification of the method of Hofstee [Hofstee, B. H. Non-inverted versus inverted plots in enzyme kinetics. Nature 184: 1296-1298, (1959)] for determination of the apparent Michaelis constants and maximum velocities. Substituting {relative adiponectin secretion/[concentration]} for the independent variable v/[S] and {relative adiponectin secretion} for the dependant variable {v}, produced a relationship of the form y=mx+b. Maximum adiponectin secretion relative to the solvent control was estimated from the y-intercept, while the concentration of test material necessary for half maximal adiponectin secretion was computed from the negative value of the slope.

Figure 13:
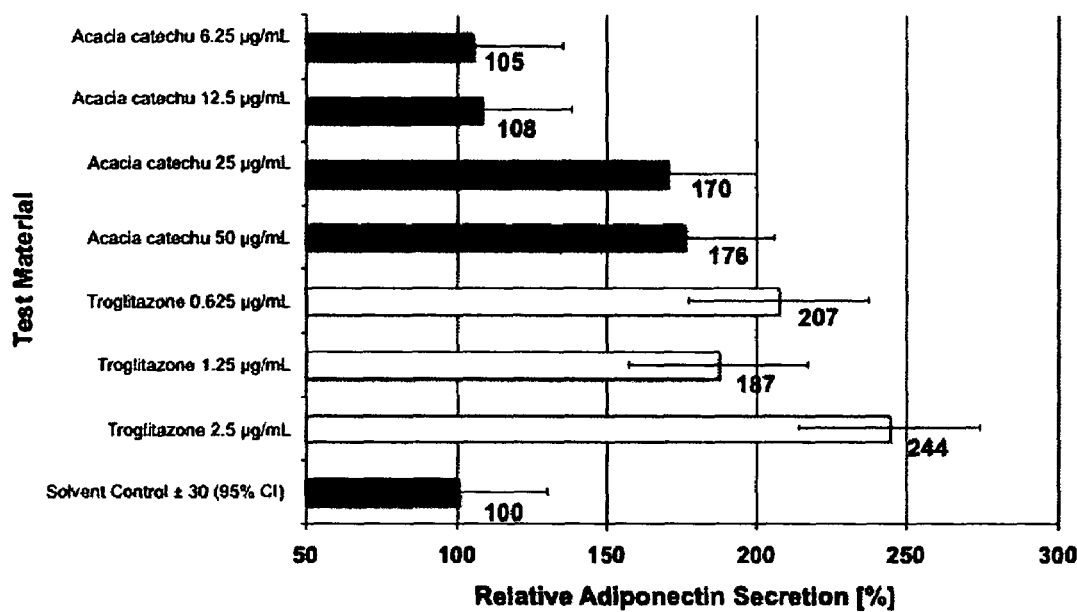
FIG. 13 is a representative bar graph depicting maximum adiponectin secretion by insulin-resistant 3T3-L1 cells in 24 hr elicited by three doses of troglitazone and four doses of a dimethyl sulfoxide-soluble fraction of an aqueous extract of *Acacia* sample #4909. Values presented are percent relative to the solvent control; error bars represent 95% confidence intervals.

Results—All concentrations tested for the positive control troglitazone enhanced adiponectin secretion with maximal stimulation of 2.44-fold at 2.5 µg/ml relative to the solvent control in insulin-resistant 3T3-L1 cells (FIG. 13). Both the 50 and 25 µg *Acacia*/ml concentrations increased adiponectin secretion relative to the solvent controls 1.76- and 1.70-fold respectively. While neither of these concentrations of *Acacia* was equal to the maximal adiponectin secretion observed with troglitazone, they were comparable to the 1.25 and 0.625 µg/ml concentrations of troglitazone.

Estimates of maximal adiponectin secretion derived from modified Hofstee plots indicated a comparable relative increase in adiponectin secretion with a large difference in concentrations required for half maximal stimulation. Maximum adiponectin secretion estimated from the y-intercept for troglitazone and *Acacia catechu* was, respectively, 2.29- and 1.88-fold relative to the solvent control. However, the concentration required for stimulation of half maximal adiponectin secretion in insulin-resistant 3T3-L1 cells was 0.085 µg/ml for troglitazone and 5.38 µg/ml for *Acacia*. Computed upon minimum apecatechin content of 20%, this latter figure for *Acacia* becomes approximately 1.0 µg/ml.

Based upon its ability to enhance adiponectin secretion in insulin-resistant 3T3-L1 cells, *Acacia*, and/or apecatechin, may be expected to have a positive effect on clinical pathologies in which plasma adiponectin concentrations are depressed.

Example 13

Increased Adiponectin Secretion from TNFα-Treated 3T3-L1 Adipocytes Elicited by a Dimethyl Sulfoxide-Soluble Fraction of an Aqueous Extract of *Acacia*

The Model—The 3T3-L1 murine fibroblast model as described in Example 11 was used in these experiments.

Test Materials—Indomethacin, methylisobutylxanthine, dexamethasone, and insulin were obtained from Sigma (St. Louis, Mo.). The test material was a dark brown powder produced from a 50:50 (v/v) water/alcohol extract of the gum resin of *Acacia* sample #4909 and was obtained from Bayir Chemicals (No. 68, South Cross Road, Basavanagudi, India). The extract was standardized to contain not less than 20% apecatechin. Batch No. A Cat/2304 used in this example contained 20.8% apecatechin as determined by UV analysis. Penicillin, streptomycin, Dulbecco's modified Eagle's medium (DMEM) was from Mediatech (Herndon, Va.) and 10% FBS (fetal bovine serum) characterized from Mediatech and Hyclone (Logan, Utah). All other standard reagents, unless otherwise indicted, were purchased from Sigma.

Figure 14:
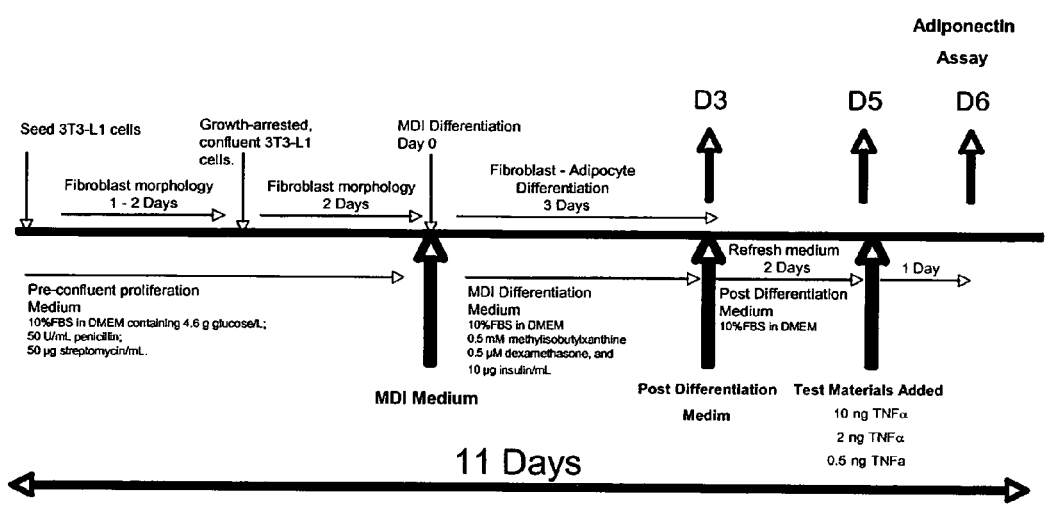
FIG. 14 is a schematic of a representative testing protocol for assessing the effect of a dimethyl sulfoxide-soluble fraction of an aqueous extract of *Acacia* sample #4909 on the secretion of adiponectin from 3T3-L1 adipocytes treated with test material plus 10, 2 or 0.5 ng TNFα/ml.

Cell culture and Treatment—Culture of the murine fibroblast cell line 3T3-L1 to produce Day 3 differentiated adipocytes was performed as described in Example 10. 3T3-L1 cells were seeded at an initial density of $1 \times 10^4$ cells/cm$^2$ in 96-well plates. For two days, the cells were allowed grow to reach confluence. Following confluence, the cells were forced to differentiate into adipocytes by the addition of differentiation medium; this medium consisted of (1) 10% FBS/DMEM (high glucose); (2) 0.5 mM methylisobutylxanthine; (3) 0.5 µM dexamethasone and (4) 10 µg/ml insulin (MDI medium). From Day 3 through Day 5, the medium was changed to post-differentiation medium consisting of 10% FBS in DMEM. On Day 5 the medium was changed to test medium containing 10, 2 or 0.5 ng TNFα/ml in 10% FBS/DMEM with or without indomethacin or *Acacia* extract. Indomethacin was dissolved in dimethyl sulfoxide and added to achieve concentrations of 5, 2.5, 1.25 and 0.625 µg/ml. The *Acacia* extract was tested at 50, 25, 12.5 and 6.25 µg/ml. On Day 6, the supernatant medium was sampled for adiponectin determination. The complete procedure for differentiation and treatment of cells with test materials is outlined schematically in FIG. 14.

Adiponectin Assay—The adiponectin secreted into the medium was quantified using the Mouse Adiponectin Quantikine® Immunoassay kit with no modifications (R&D Systems, Minneapolis, Minn.). Information supplied by the manufacturer indicated that recovery of adiponectin spiked in mouse cell culture media averaged 103% and the minimum detectable adiponectin concentration ranged from 0.001 to 0.007 ng/ml.

Statistical Calculations and Interpretation—All assays were preformed in duplicate. For statistical analysis, the effect of indomethacin or *Acacia catechu* on adiponectin secretion was computed relative to the solvent control. Differences among the doses and test agents were determined using the Student's t-test without correction for multiple comparisons; the nominal five percent probability of a type I error was selected.

Figure 15:
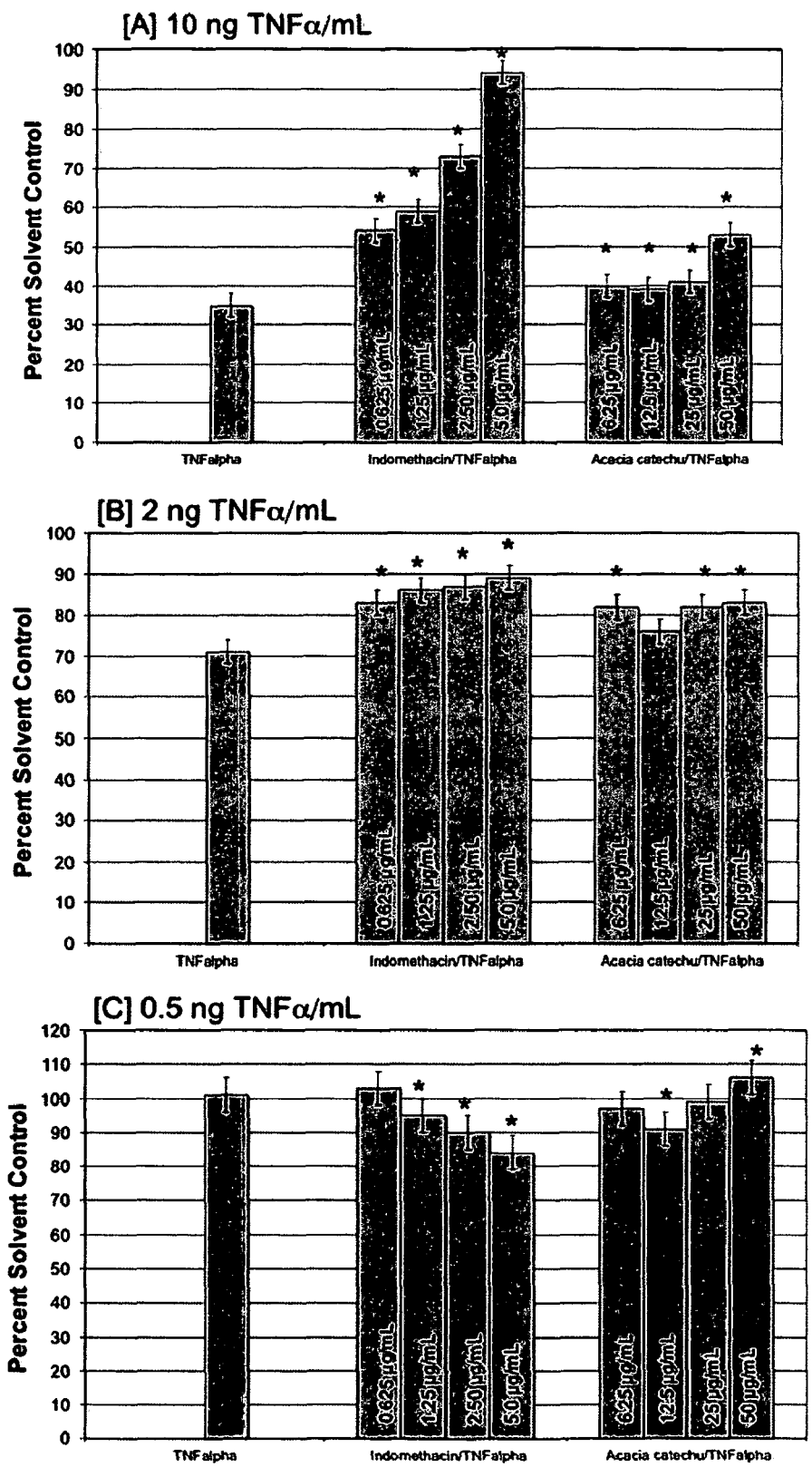
FIG. 15 depicts representative bar graphs representing adiponectin secretion by TNFα treated mature 3T3-L1 cells elicited by indomethacin or an *Acacia* sample #4909 extract. Values presented are percent relative to the solvent control; error bars represent 95% confidence intervals. *Significantly different from TNFα alone treatment (p<0.05).

Results—TNFα significantly (p<0.05) depressed adiponectin secretion 65 and 29%, respectively, relative to the solvent controls in mature 3T3-L1 cells at the 10 and 2 ng/ml concentrations and had no apparent effect on adiponectin secretion at 0.5 ng/ml (FIG. 15). At 10 and 2 ng TNFα/ml, indomethacin enhanced (p<0.05) adiponectin secretion relative to TNFα alone at all doses tested, but failed to restore adiponectin secretion to the level of the solvent control. *Acacia* treatment in the presence of 10 ng TNFα/ml, produced a similar, albeit attenuated, adiponectin increase relative to that of indomethacin. The differences in adiponectin stimulation between *Acacia catechu* and indomethacin were 14, 20, 32, and 41%, respectively, over the four increasing doses. Since the multiple between doses was the same for indomethacin and *Acacia*, these results suggest that the potency of indomethacin was greater than the active material(s) in *Acacia* at restoring adiponectin secretion to 3T3-L1 cells in the presence of supraphysiological concentrations of TNFα.

Treatment of 3T3-L1 cells with 2 ng TNFα and *Acacia* produced increases in adiponectin secretion relative to TNFα alone that were significant (p<0.05) at 6.25, 25 and 50 µg/ml. Unlike the 10 ng TNFα/ml treatments, however, the differences between *Acacia* and indomethacin were smaller and not apparently related to dose, averaging 5.5% over all four concentrations tested. As observed with indomethacin, *Acacia* did not restore adiponectin secretion to the levels observed in the solvent control.

At 0.5 ng TNFα/ml, indomethacin produced a dose-dependant decrease in adiponectin secretion that was significant (p<0.05) at the 2.5 and 5.0 µg/ml concentrations. Interestingly, unlike indomethacin, *Acacia catechu* increased adiponectin secretion relative to both the TNFα and solvent treated 3T3-L1 adipocytes at 50 µg/ml. Thus, at concentrations of TNFα approaching physiologic levels, *Acacia catechu* enhanced adiponectin secretion relative to both TNFα and the solvent controls and, surprisingly, was superior to indomethacin.

Based upon its ability to enhance adiponectin secretion in TNFα-treated 3T3-L1 cells, *Acacia catechu*, and/or apecatechin, would be expected to have a positive effect on all clinical pathologies in which TNFα levels are elevated and plasma adiponectin concentrations are depressed.

Example 14

A Variety of Commercial *Acacia* Samples Increase Lipogenesis in the 3T3-L1 Adipocyte Model The Model—The 3T3-L1 murine fibroblast model as described in Example 11 was used in these experiments. All chemicals and procedures used were as described in Example 11 with the exception that only the Oil Red O assay was performed to assess *Acacia catechu*-induced, cellular triglyceride content. *Acacia catechu* sample #5669 was obtained from Natural Remedies (364, 2nd Floor, 16th Main, 4th T Block Bangalore, Karnataka 560041 India); and samples #4909, #5667, and #5668 were obtained from Bayir Chemicals (No. 10, Doddanna Industrial Estate, Penya II Stage, Bangalore, 560091 Karnataka, India). *Acacia nilotica* samples #5639, #5640 and #5659 were purchased from KDN-Vita International, Inc. (121 Stryker Lane, Units 4 & 6 Hillsborough, N.J. 08844). Sample #5640 was described as bark, sample #5667 as a gum resin and sample #5669 as heartwood powder. All other samples unless indicated were described as proprietary methanol extracts of *Acacia catechu* bark.

Figure 16:
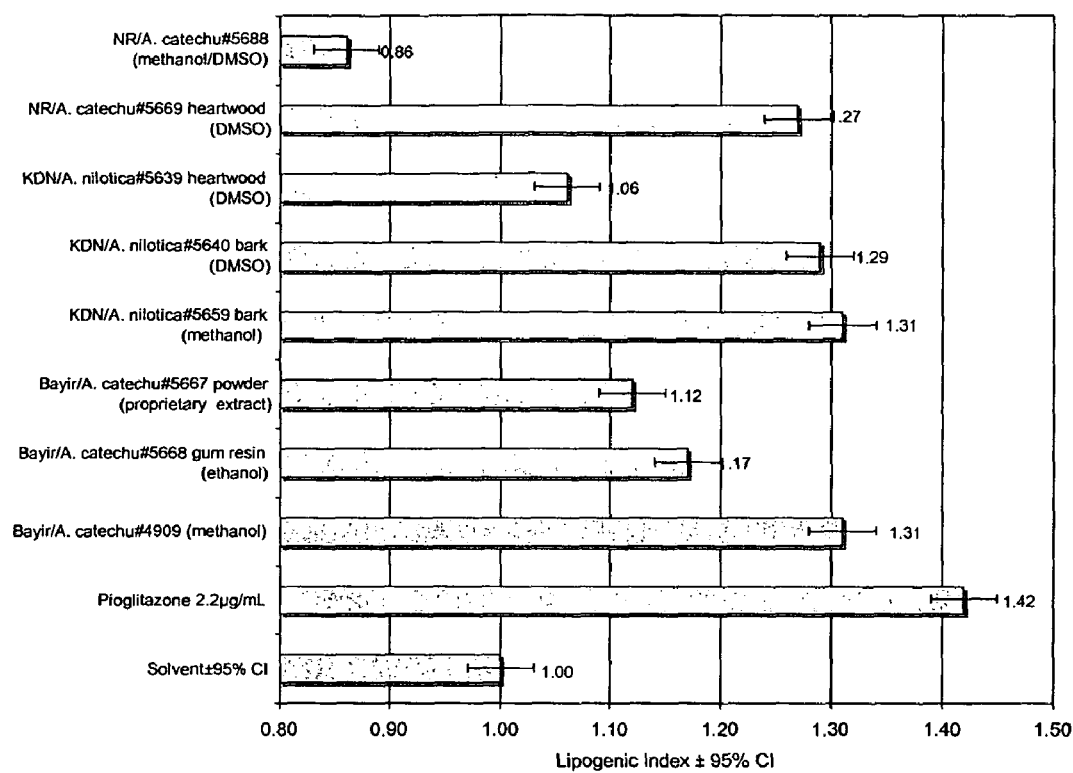
FIG. 16 graphically illustrates the relative increase in triglyceride content in insulin resistant 3T3-L1 adipocytes by various compositions of *Acacia catechu* and *A. nilotica* from different commercial sources. Values presented are percent relative to the solvent control; error bars represent 95% confidence intervals.

Results—All *Acacia* samples examined produced a positive lipogenic response (FIG. 16). The highest lipogenic responses were achieved from samples #5669 the heartwood powder (1.27), #5659 a methanol extract (1.31), #5640 a DMSO extract (1.29) and #4909 a methanol extract (1.31).

This example further demonstrates the presence of multiple compounds in *Acacia catechu* that are capable of positive modification of adipocyte physiology supporting increased insulin actions.

Example 15

A Variety of Commercial *Acacia* Samples Increase Adiponectin Secretion the TNFα-3T3-L1 Adipocyte Model The Model—The 3T3-L1 murine fibroblast model as described in Example 11 was used in these experiments. Standard chemicals used and treatment of cells was performed as noted in Examples 11 and 13. Treatment of 3T3-L1 adipocytes with TNFα differed from Example 12, however, in that cells were exposed to 2 or 10 ng TNFα/ml only. On Day 6 culture supernatant media were assayed for adiponectin as detailed in Example 12. Formulations of *Acacia* samples #4909, #5639, #5659, #5667, #5668, #5640, and #5669 were as described in Example 13.

Results—The 2 ng/ml TNFα reduced adiponectin secretion of 3T3-L1 adipocytes by 27% from the solvent control, while adiponectin secretion was maximally elevated 11% from the TNFα solvent control by 1.25 µg indomethacin/ml (Table 12). Only *Acacia* formulation #5559 failed to increase adiponectin secretion at any of the four doses tested. All other formulations of *Acacia* produced a comparable maximum increase of adiponectin secretion ranging from 10 to 15%. Differences were observed, however, with regard to the concentrations at which maximum adiponectin secretion was elicited by the various *Acacia* formulations. The most potent formulation was #5640 with a maximal stimulation of adiponectin stimulation achieved at 12.5 µg/ml, followed by #4909 and #5668 at 25 µg/ml and finally #5639, #5667 and #5669 at 50 µg/ml.

TABLE 12

Relative maximum adiponectin secretion from 3T3-L1 adipocytes elicited by various formulations of Acacia in the presence of 2 ng TNFα/ml.

| Test Material | Concentration [µg/ml] | Adiponectin Index† |
|---|---|---|
| 2 ng TNFα/ml ± 95% CI | — | 1.00 ± 0.05 |
| Solvent control | — | 1.27* |
| Indomethacin | 1.25 | 1.11* |
| Acacia catechu #4909 Bark (methanol extract) | 25.0 | 1.15* |
| Acacia nilotica #5639 Heartwood (DMSO extract) | 50.0 | 1.14* |
| Acacia nilotica #5659 Bark (methanol extract) | 25 | 1.02 |
| Acacia catechu #5667 Bark (methanol extract) | 50.0 | 1.10* |
| Acacia catechu #5668 (Gum resin) | 25.0 | 1.15* |
| Acacia nilotica #5640 Bark (DMSO extract) | 12.5 | 1.14* |
| Acacia catechu #5669 Heartwood powder (DMSO extract) | 50.0 | 1.14* |

†Adiponectin Index = [Adiponectin]$_{Test}$/[Adiponectin]$_{TNF\alpha\ control}$
*Significantly increased (p < 0.05) from TNFα solvent response.

The 10 ng/ml TNFα reduced adiponectin secretion of 3T3-L1 adipocytes by 54% from the solvent control, while adiponectin secretion was maximally elevated 67% from the TNFα solvent control by 5.0 µg indomethacin/ml (Table 13). Troglitazone maximally increased adiponectin secretion 51% at the lowest dose tested 0.625 µg/ml. Acacia formulation #5559 produced the lowest significant increase (p<0.05) of 12% at 25 µg/ml. All other formulations of Acacia produced a maximum increase of adiponectin secretion at 50 µg/ml ranging from 17 to 41%. The most potent formulations were #4909 and #5669 with increases in adiponectin secretion of 41 and 40%, respectively over the TNFα solvent control.

TABLE 13

Relative maximum adiponectin secretion from 3T3-L1 adipocytes elicited by various formulations of Acacia in the presence of 10 ng TNFα/ml.

| Test Material | Concentration [µg/ml] | Adiponectin Index† |
|---|---|---|
| 10 ng TNFα/ml ± 95% CI | — | 1.00 ± 0.10 |
| Solvent control | — | 1.54* |
| Indomethacin | 5.0 | 1.67* |
| Troglitazone | 0.625 | 1.51* |
| Acacia catechu #4909 Bark (methanol extract) | 50 | 1.41* |
| Acacia nilotica #5639 Heartwood (DMSO extract) | 50 | 1.26* |
| Acacia nilotica #5659 Bark (methanol extract) | 25 | 1.12* |
| Acacia catechu #5667 Bark (methanol extract) | 50 | 1.26* |
| Acacia catechu #5668 (Gum resin) | 50 | 1.30* |
| Acacia nilotica #5640 Bark (DMSO extract) | 50 | 1.17* |
| Acacia catechu #5669 Heartwood powder (DMSO extract) | 50 | 1.40* |

†Adiponectin Index = [Adiponectin]$_{Test}$/[Adiponectin]$_{TNF\alpha\ control}$
*Significantly increased (p < 0.05) from TNFα solvent response.

The observation that different samples or formulations of Acacia elicit similar responses in this second model of metabolic syndrome, further demonstrates the presence of multiple compounds in Acacia that are capable of positive modification of adipocyte physiology supporting increased insulin actions.

Example 16

Polar and Non-Polar Solvents Extract Compounds from Acacia catechu Capable of Increasing Adiponectin Secretion in the TNFα/3T3-L1 Adipocyte Model The Model—The 3T3-L1 murine fibroblast model as described in Example 11 was used in these experiments. Standard chemicals used are as noted in Examples 11 and 13. 3T3-L1 adipocytes were treated with 10 ng TNFα/ml as described in Example 13. Culture supernatant media were assayed for adiponectin on Day 6 as detailed in Example 13.

Test Materials—Large chips of Acacia catechu sample #5669 heartwood (each chip weighing between 5-10 grams) were subjected to drilling with a ⅝" metal drill bit using a standard power drill at low speed. The wood shavings were collected into a mortar, and ground into a fine powder while frozen under liquid $N_2$. This powder was then sieved through a 250 micron screen to render approximately 10 g of a fine free-flowing powder.

TABLE 14

Description of Acacia catechu extraction samples for 3T3-L1 adiponectin assay.

| Extraction solvent | Weight of extract [mg] | Percent Extracted |
|---|---|---|
| Gastric fluid[1] | 16 | 11 |
| Dimethyl sulfoxide | 40 | 27 |
| Chloroform | 0.2 | 0.13 |
| Methanol/water pH = 2 95:5 | 20 | 13 |
| Water | 10 | 6.7 |
| Ethyl acetate | 4 | 2.7 |

[1]Gastric fluid consisted of 2.90 g NaCl, 7.0 ml concentrated, aqueous HCl, 3.2 g pepsin (800-2500 activity units/mg) diluted to 1000 ml with water. Final pH was 1.2. For this extraction, the gastric fluid-heartwood suspension remained at 40° C. for one hour followed by removal of the gastric fluid in vacuo. The remaining residue was then dissolved in MeOH, filtered through a 0.45 micron PTFE syringe filter and concentrated in vacuo.

This powder was dispensed into six glass amber vials (150 mg/vial) and extracted at 40° C. for approximately 10 hr with 2 ml of the solvents listed in Table 14. Following this extraction, the heartwood/solvent suspensions were subjected to centrifugation (5800×g, 10 min.). The supernatant fractions from centrifugation were filtered through a 0.45 micron PTFE syringe filter into separate amber glass vials. Each of these samples was concentrated in vacuo. As seen in Table 7, DMSO extracted the most material from the Acacia catechu heartwood and chloroform extracted the least. All extract samples were tested at 50, 25, 12.5, and 6.25 µg/ml.

Pioglitazone was obtained as 45 mg pioglitazone tables from a commercial source as Actos® (Takeda Pharmaceuticals, Lincolnshire, Ill.). The tablets were ground to a fine powder and tested at 5.0, 2.5, 1.25 and 0.625 µg pioglitazone/ml. Indomethacin was also included as an additional positive control.

Figure 17:
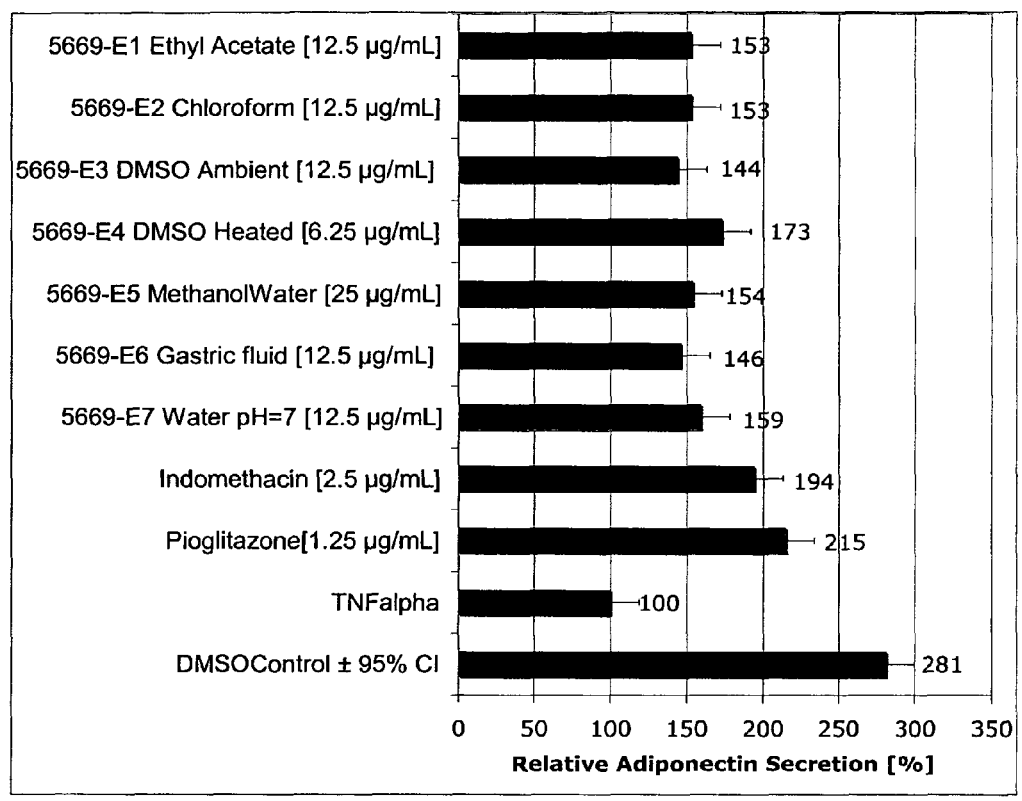
FIG. 17 graphically depicts a representation of the maximum relative adiponectin secretion elicited by various extracts of *Acacia catechu*. Values presented are percent relative to the solvent control; error bars represent 95% confidence intervals.

Results—Both positive controls pioglitazone and indomethacin increased adiponectin secretion by adipocytes in the presence of TNFα, 115 and 94% respectively (FIG. 17). Optimal pioglitazone and indomethacin concentrations were, 1.25 and 2.5 µg/ml respectively. All extracts of Acacia catechu sample #5669 increased adiponectin secretion relative to the TNFα treatment. Among the extracts, the DMSO extract was the most potent inducer of adiponectin secretion with maximal activity observed at 6.25 µg extract/ml. This result may be due to the ability of DMSO to extract a wide range of materials of varying polarity. An examination of FIG. 17 indicates that both the water extract (polar compounds) and the chloroform extract (nonpolar compounds)

were similar in their ability to increase adiponectin secretion in the TNFα/3T3-L1 adipocyte model. It is unlikely that these extracts contained similar compounds. This example illustrates the ability of solvents with differing polarities to extract compounds from *Acacia catechu* heartwood that are capable of increasing adiponectin secretion from adipocytes in the presence of a pro-inflammatory stimulus.

Example 17

*Acacia catechu* Acidic and Basic Fractions are Capable of Increasing Adiponectin Secretion in the TNFα/3T3-L1 Adipocyte Model The Model—The 3T3-L1 murine fibroblast model as described in Example 11 was used in these experiments. Standard chemicals used were as noted in Examples 11 and 13. 3T3-L1 adipocytes were treated with 10 ng TNFα/ml as described in Example 13. Culture supernatant media were assayed for adiponectin on Day 6 as detailed in Example 13.

Test Materials—*Acacia catechu* sample #5669 was extracted according to the following procedure: Alkaline isopropyl alcohol solution, (1% (v/v) 1.5N NaOH in isopropanol) was added to approximately 50 mg of the dry *Acacia catechu* heartwood powder #5669 in a 50 ml tube. The sample was then mixed briefly, sonicated for 30 minutes, and centrifuged for an hour to pellet the remaining solid material. The supernatant liquid was then filtered through 0.45 micron filter paper. The pH of the basic isopropanol used was pH 8.0, while the pH of the collected liquid was pH 7.0. A portion of the clear, filtered liquid was taken to dryness in vacuo and appeared as a white solid. This sample was termed the dried alkaline extract.

The remaining pelleted material was brought up in acidic isopropyl alcohol solution, (1% (v/v) 10% HCl in isopropanol) as a red solution. This sample was mixed until the pellet material was sufficiently dispersed in the liquid and then centrifuged for 30 minutes to again pellet the remaining solid. The pale yellow supernatant fluid was passed through a 0.45 micron filter paper. The pH of the collected liquid was pH 3.0 and it was found that in raising the pH of the sample to pH 8-9 a reddish-brown precipitate was formed (dried precipitate). The precipitate was collected and dried, providing a reddish-brown solid. The supernatant liquid was again passed through a 0.45 micron filter to remove any remaining precipitate; this liquid was a deep yellow color. This remaining liquid was taken to dryness resulting in a solid brown sample and termed dried acidic extract. Recoveries for the three factions are listed in Table 15. All test materials were assayed at 50, 25, 12.5 and 6.25 μg/ml, while the pioglitazone positive control was tested at 5.0, 2.5, 1.25 and 0.625 μg/ml.

TABLE 15

Test material recovery from *Acacia catechu* heartwood powder.

| Test Material | mg collected (% *Acacia catechu* sample #5669) |
|---|---|
| Dried alkaline extract | 0.9 (1.8) |
| Dried precipitate | 1.2 (2.4) |
| Dried acidic extract | 1.5 (3.0) |

Results: TNFα reduced adiponectin secretion by 46% relative to the solvent control. Maximal restoration of adiponectin secretion by pioglitazone was 1.47 times the TNFα treatment observed at 1.25 μg/ml (Table 16). Of the test materials, only the dried precipitant failed to increase adiponectin secretion significantly above the TNFα only control. The acidic extract and heartwood powder (starting material) were similar in their ability to increase adiponectin secretion in the presence of TNFα, while the alkaline extract increased adiponectin secretion only at the highest dose of 50 μg/ml.

TABLE 16

Maximum adiponectin secretion elicited over four doses in TNFα/3T3-L1 model.

| Test Material | Concentration [μg/ml] | Adiponectin Index† |
|---|---|---|
| DMSO Control | — | 1.86 |
| TNFα ± 95% CI | — | 1.00 ± 0.11†† |
| *Acacia catechu* sample #5669 heartwood powder | 6.25 | 1.14 |
| Dried alkaline extract | 50 | 1.19 |
| Dried precipitate | 6.25 | 1.09 |
| Dried acidic extract | 6.25 | 1.16 |
| Pioglitazone | 1.25 | 1.47 |

†Adiponectin Index = [Adiponectin]$_{Test}$/[Adiponectin]$_{TNFα\ control}$
††Values > 1.11 are significantly different (p < 0.05) from TNFα control.

Example 18

Decreased Interleukin-6 Secretion from TNFα-Treated 3T3-L1 Adipocytes by a Dimethyl Sulfoxide-Soluble Fraction of an Aqueous Extract of *Acacia*

Interleukin-6 (IL-6) is a multifunctional cytokine that plays important roles in host defense, acute phase reactions, immune responses, nerve cell functions, hematopoiesis and metabolic syndrome. It is expressed by a variety of normal and transformed lymphoid and nonlymphoid cells such as adipocytes. The production of IL-6 is up-regulated by numerous signals such as mitogenic or antigenic stimulation, lipopolysaccharides, calcium ionophores, cytokines and viruses [Hibi, M., Nakajima, K., Hirano T. IL-6 cytokine family and signal transduction: a model of the cytokine system. J Mol Med. 74(1):1-12, (January 1996)]. Elevated serum levels have been observed in a number of pathological conditions including bacterial and viral infection, trauma, autoimmune diseases, malignancies and metabolic syndrome [Arner, P. Insulin resistance in type 2 diabetes—role of the adipokines. Curr Mol Med.; 5(3):333-9, (May 2005)].

The Model—The 3T3-L1 murine fibroblast model as described in Example 11 was used in these experiments. Standard chemicals used were as noted in Examples 11 and 13. 3T3-L1 adipocytes were treated with 10 ng TNFα/ml as described in Example 13. Culture supernatant media were assayed for adiponectin on Day 6 as detailed in Example 13.

Test Materials—Indomethacin, methylisobutylxanthine, dexamethasone, and insulin were obtained from Sigma (St. Louis, Mo.). The test material was a dark brown powder produced from a 50:50 (v/v) water/alcohol extract of the gum resin of *Acacia catechu* sample #4909 and was obtained from Bayir Chemicals (No. 68, South Cross Road, Basavanagudi, India). The extract was standardized to contain not less than 20% apecatechin. Batch No. A Cat/2304 used in this example contained 20.8% apecatechin as determined by UV analysis. Penicillin, streptomycin, Dulbecco's modified Eagle's medium (DMEM) was from Mediatech (Herndon, Va.) and 10% FBS (fetal bovine serum) characterized from Mediatech and Hyclone (Logan, Utah). All other standard reagents, unless otherwise indicted, were purchased from Sigma.

Interleukin-6 Assay—The IL-6 secreted into the medium was quantified using the Quantikine® Mouse IL-6 Immunoassay kit with no modifications (R&D Systems, Minneapolis, Minn.). Information supplied by the manufacturer indicated that recovery of IL-6 spiked in mouse cell culture media averaged 99% with a 1:2 dilution and the minimum detectable IL-6 concentration ranged from 1.3 to 1.8 pg/ml. All supernatant media samples were assayed undiluted.

Statistical Calculations and Interpretation—All assays were preformed in duplicate. For statistical analysis, the effect of Acacia on adiponectin or IL-6 secretion was computed relative to the solvent control. Differences among the doses were determined using the student's t-test without correction for multiple comparisons; the nominal five percent probability of a type I error (one-tail) was selected.

Results—As seen in previous examples, TNFα dramatically reduced adiponectin secretion, while both indomethacin and the Acacia catechu extract increased adiponectin secretion in the presence of TNFα. Although both the indomethacin positive control and Acacia catechu extract demonstrated dose-related increases in adiponectin secretion, neither material restored adiponectin concentrations to those seen in the dimethyl sulfoxide controls with no TNFα (Table 17). The Acacia catechu extract demonstrated a potent, dose-related inhibition of IL-6 secretion in the presence of TNFα, whereas indomethacin demonstrated no anti-inflammatory effect.

An examination of the ratio of the anti-inflammatory adiponectin to the pro-inflammatory IL-6 resulted in an excellent dose-related increase in relative anti-inflammatory activity for both indomethacin and the Acacia catechu extract.

TABLE 17

Decreased IL-6 and increased adiponectin secretion elicited by Acacia catechu sample #4909 in the TNFα/3T3-L1 model.

| Test Material | Concentration [μg/ml] | Adiponectin Index† | IL-6 Index†† | Adiponectin/IL-6 |
|---|---|---|---|---|
| DMSO control | — | 2.87* | 0.46* | 6.24* |
| TNFα control ± 95% CI | — | 1.00 ± 0.079 | 1.00 ± 0.08 | 1.00 ± 0.08 |
| Indomethacin | 5.00 | 2.69* | 1.10* | 2.45* |
|  | 2.50 | 2.08* | 1.04 | 2.00* |
|  | 1.25 | 1.71* | 1.01 | 1.69* |
|  | 0.625 | 1.54* | 1.37* | 1.12* |
| Acacia catechu sample #4909 | 50.0 | 1.51* | 0.27* | 5.55* |
|  | 25.0 | 1.19* | 0.71* | 1.68* |
|  | 12.5 | 1.13* | 0.78* | 1.45* |
|  | 6.25 | 1.15* | 0.93 | 1.23* |

The Acacia catechu test material or indomethacin was added in concert with 10 ng TNFα/ml to D5 3T3-L1 adipocytes. On the following day, supernatant media were sampled for adiponectin and IL-6 determination. All values were indexed to the TNFα control.
†Adiponectin Index = [Adiponectin]$_{Test}$/[Adiponectin]$_{TNFα\ control}$
††IL-6 Index = [IL-6$_{Test}$ − IL-6$_{Control}$]/[IL-6$_{TNFα}$ − IL-6$_{Control}$]
*Significantly different from TNFα control $p < 0.05$).

Acacia catechu sample #4909 demonstrated a dual anti-inflammatory action in the TNFα/3T3-L1 adipocyte model. Components of the Acacia catechu extract increased adiponectin secretion while decreasing IL-6 secretion. The overall effect of Acacia catechu was strongly anti-inflammatory relative to the TNFα controls. These results support the use of Acacia catechu for modification of adipocyte physiology to decrease insulin resistance weight gain, obesity, cardiovascular disease and cancer.

Example 19

Effect of a Dimethyl Sulfoxide-Soluble Fraction of an Aqueous Acacia Extract on Secretion of Adiponectin, IL-6 and Resistin from Insulin-Resistant 3T3-L1 Adipocytes The Model—The 3T3-L1 murine fibroblast model as described in Example 11 was used in these experiments. Standard chemicals and statistical procedures used were as noted in Examples 11 and 12. Il-6 was assayed as described in Example 18.

Resistin Assay—The amount of resistin secreted into the medium was quantified using the Quantikine®R Mouse Resistin Immunoassay kit with no modifications (R&D Systems, Minneapolis, Minn.). Information supplied by the manufacturer indicated that recovery of resistin spiked in mouse cell culture media averaged 99% with a 1:2 dilution and the minimum detectable resistin concentration ranged from 1.3 to 1.8 pg/ml. All supernatant media samples were diluted 1:20 with dilution media supplied by the manufacturer before assay.

Statistical Calculations and Interpretation—All assays were preformed in duplicate. For statistical analysis, the effect of Acacia catechu on adiponectin or IL-6 secretion was computed relative to the solvent control. Differences among the doses were determined using the Student's t-test without correction for multiple comparisons; the nominal five percent probability of a type I error (one-tail) was selected.

Results—Both troglitazone and the Acacia sample #4909 increased adiponectin secretion in a dose-related manner in the presence of high concentrations of insulin (Table 18). While Acacia catechu exhibited an anti-inflammatory effect through the reduction of IL-6 at only the 6.25 μg/ml, concentration, troglitazone was pro-inflammatory at the 5.00 and 1.25 μg/ml concentrations, with no effect observed at the other two concentrations. Resistin secretion was increased in a dose-dependent fashion by troglitazone; however, Acacia catechu decreased resistin expression likewise in a dose-dependent manner.

As seen in Example 18, Acacia catechu sample #4909 again demonstrated a dual anti-inflammatory action in the hyperinsulemia/3T3-L1 adipocyte model. Components of the Acacia catechu extract increased adiponectin secretion while decreasing IL-6 secretion. Thus, the overall effect of Acacia catechu was anti-inflammatory relative to the high insulin controls. The effect of Acacia catechu on resistin secretion in the presence of high insulin concentrations was contrary to those of troglitazone: troglitazone increased resistin expression, while Acacia catechu further decreased resistin expression. These data suggest that the complex Acacia catechu extract are not functioning through PPARγ receptors. These results provide further support the use of Acacia catechu for modification of adipocyte physiology to decrease insulin resistance weight gain, obesity, cardiovascular disease and cancer.

TABLE 18

Effect of Acacia catechu extract on adiponectin, IL-6 and resistin secretion in the insulin resistant 3T3-L1 model.

| Test Material | Concentration [μg/ml] | Adiponectin Index† | IL-6 Index†† | Resistin Index††† |
|---|---|---|---|---|
| Insulin control | — | 1.00 ± 0.30* | 1.00 ± 0.23 | 1.00 ± 0.13 |
| Troglitazone | 5.00 | 1.47 | 1.31 | 1.43 |

TABLE 18-continued

Effect of *Acacia catechu* extract on adiponectin, IL-6 and resistin secretion in the insulin resistant 3T3-L1 model.

| Test Material | Concentration [µg/ml] | Adiponectin Index† | IL-6 Index†† | Resistin Index††† |
|---|---|---|---|---|
| | 2.50 | 2.44 | 1.06 | 1.22 |
| | 1.25 | 1.87 | 1.46 | 1.28 |
| | 0.625 | 2.07 | 1.00 | 0.89 |
| *Acacia catechu* sample #4909 | 50.0 | 1.76 | 1.23 | 0.50 |
| | 25.0 | 1.70 | 0.96 | 0.61 |
| | 12.5 | 1.08 | 0.92 | 0.86 |
| | 6.25 | 1.05 | 0.64 | 0.93 |

The *Acacia catechu* test material or indomethacin was added in concert with 166 nM insulin to D5 3T3-L1 adipocytes. On the following day, supernatant media were sampled for adiponectin, IL-6 and resistin determination. All values were indexed to the insulin only control.
†Adiponectin Index = [Adiponectin]$_{Test}$/[Adiponectin]$_{Insulin\ Control}$
††IL-6 Index = [IL-6$_{Test}$]/[IL-6$_{Insulin\ Control}$]
†††Resistin Index = [Resistin$_{Test}$]/[Resistin$_{Insulin\ Control}$]
*Index values represent the mean ± 95% confidence interval computed from residual mean square of the analysis of variance. Values greater or less than Insulin control ± 95% CI are significantly different with $p < 0.05$.

Example 20

Increased Lipogenesis in Adipocytes by Phytochemicals Derived from Hops

The Model—The 3T3-L1 murine fibroblast model as described in Example 11 was used in these experiments. Standard chemicals and statistical procedures used were as noted in Example 11.

Test Materials—The hops phytochemicals used in this testing are described in Table 19 and were acquired from Betatech Hops Products (Washington, D.C., U.S.A.).

TABLE 19

Description of hops test materials.

| Hops Test Material | Description |
|---|---|
| Alpha acid solution | 82% alpha acids/2.7% beta acids/2.95% isoalpha acids by volume. Alpha acids include humulone, adhumulone, and cohumulone. |
| Rho isoalpha acids (RIAA) | Rho-isohumulone, rho-isoadhumulone, and rho-isocohumulone. |
| Isoalpha acids (IAA) | 25.3% isoalpha acids by volume. Includes cis & trans isohumulone, cis & trans isoadhumulone, and cis & trans isocohumulone. |
| Tetrahydroisoalpha acids (THIAA) | Complex hops - 8.9% THIAA by volume. Includes cis & trans tetrahydro-isohumulone, cis & trans tetrahydro-isoadhumulone and cis & trans tetrahydro-isocohumulone |
| Hexahydroisoalpha acids (HHIAA) | 3.9% THIAA; 4.4% HHIAA by volume. The HHIAA isomers include hexahydro-isohumulone, hexahydro-isoadhumulone and hexahydro-isocohumulone. |
| Beta acid solution | 10% beta acids by volume; <2% alpha acids. The beta acids include lupulone, colupulone, adlupulone and prelupulone. |
| Xanthohumol (XN) | >80% xanthohumols by weight. Includes xanthohumol, xanthohumol A, xanthohumol B, xanthohumol C, xanthohumol D, xanthohumol E, xanthohumol G, xanthohumol H, desmethylxanthohumol, xanthogalenol, 4'-O-methylxanthohumol, 3'-geranylchalconaringenin, 3',5'diprenyl-chalconaringenin, 5'-prenylxanthohumol, flavokawin, ab-dihydroxanthohumol, and iso-dehydrocycloxanthohumol hydrate. |
| Spent hops | Xanthohumol, xanthohumol A, xanthohumol B, xanthohumol C, xanthohumol D, xanthohumol E, xanthohumol G, xanthohumol H, trans-hydroxyxanthohumol, 1",2"-dihydroxyxanthohumol C, desmethylxanthohumol B, desmethylxanthohumol J, xanthohumol I, desmethylxanthohumol, isoxanthohumol, ab dihydro-xanthohumol, diprenylxanthohumol, 5"-hydroxyxanthohumol, 5'-prenylxanthohumol, 6,8-diprenylnaringenin, 8-preylnaringenin, 6-prenylnaringen, isoxanthohumol, humulinone, cohumulinone, 4-hydroxybenzaldehyde, and sitosterol-3-O-b-glucopyranoside. |
| Hexahydro-colupulone | 1% hexahydrocolupulone by volume in KOH |

Cell Culture and Treatment—Hops compounds were dissolved in dimethyl sulfoxide (DMSO) and added to achieve concentrations of 10, 5, 4 or 2 µg/ml at Day 0 of differentiation and maintained throughout the maturation phase (Days 6 or 7). Spent hops was tested at 50 µg/ml. Whenever fresh media were added, fresh test material was also added. DMSO was chosen for its polarity and the fact that it is miscible with the aqueous cell culture media. As positive controls, indomethacin and troglitazone were added, respectively, to achieve final concentrations of 5.0 and 4.4 µg/ml. Differentiated, D6/D7 3T3-L1 cells were stained with 0.36% Oil Red O or 0.001% BODIPY.

Figure 18:
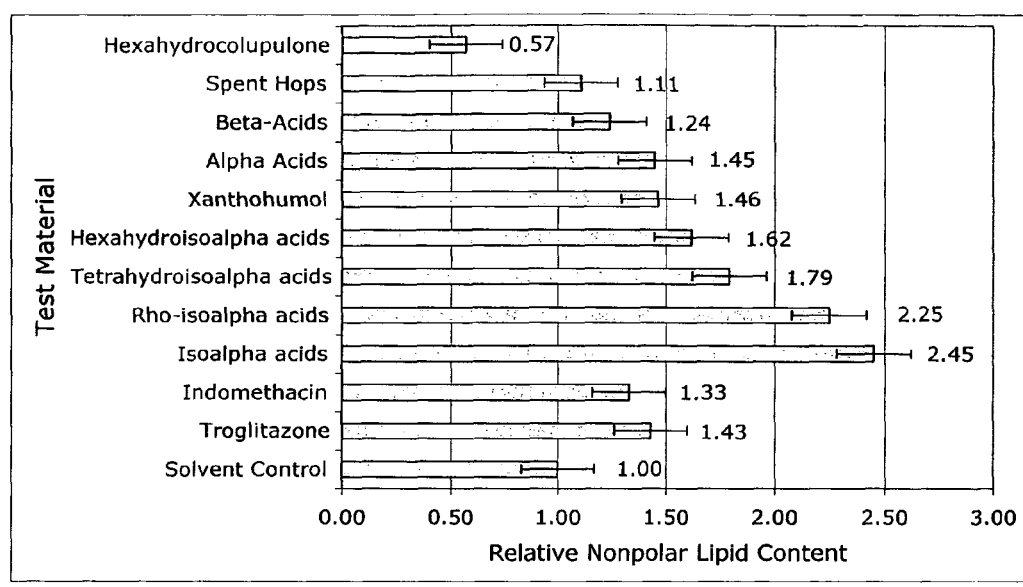
FIG. 18 graphically depicts the lipid content (relative to the solvent control) of 3T3-L1 adipocytes treated with hops compounds or the positive controls indomethacin and troglitazone. The 3T3-L1 murine fibroblast model was used to study the potential effects of the test compounds on adipocyte adipogenesis. Results are represented as relative nonpolar lipid content of control cells; error bars represent the 95% confidence interval.

Results—The positive controls indomethacin and troglitazone induced lipogenesis to a similar extent in 3T3-L1 cells (FIG. 18). Unexpectedly, four of the hops genera produced an adipogenic response in 3T3-L1 adipocytes greater than the positive controls indomethacin and troglitazone. These four genera included isoalpha acids, Rho-isoalpha acids, tetrahydroisoalpha acids, and hexahydroisoalpha acids. This finding is surprising in light of the published report that the binding of individual isohumulones with PPARγ was approximately one-third to one-fourth that of the potent PPARγ agonist pioglitazone [Yajima, H., Ikeshima, E., Shiraki, M., Kanaya, T., Fujiwara, D., Odai, H., Tsuboyama-Kasaoka, N., Ezaki, O., Oikawa, S., and Kondo, K. Isohumulones, bitter acids derived from hops, activate both peroxisome proliferator-activated receptor alpha and gamma and reduce insulin resistance. J Biol Chem, 279. 33456-33462, (2004)].

The adipogenic responses of xanthohumols, alpha acids and beta acids were comparable to indomethacin and troglitazone, while spent hops and hexahydrocolupulone failed to elicit a lipogenic response greater than the solvent controls.

Based upon their adipogenic potential in 3T3-L1 cells, the positive hops phytochemical genera in this study, which included isomerized alpha acids, alpha acids and beta acids as well as xanthohumols, may be expected to increase insulin sensitivity and decrease serum triglycerides in humans or other animals exhibiting signs or symptoms of insensitivity to insulin.

Example 21

Hops Phytochemicals Increase Adiponectin Secretion in Insulin-Resistant 3T3-L1 Adipocytes The Model—The 3T3-L1 murine fibroblast model as described in Examples 11 and 12 were used in this example. Standard chemicals, hops compounds RIAA, IAA, THIAA, HHIAA, xanthohumols, hexahydrocolupulone, spent hops were as described, respectively, in Examples 12 and 20.

Cell Culture and Treatment—Cells were cultured as described in Example 12 and treated with hops phytochemicals as previously described. Adiponectin assays and statistical interpretations were as described in Example 12. Potency of the test materials was estimated using a modification of the method of Hofstee for determination of the apparent Michaelis constants and maximum velocities. Substituting {relative adiponectin secretion/[concentration]} for the independent variable v/[S] and {relative adiponectin secretion} for the dependant variable {v}, produced a relationship of the form y=mx+b. Maximum adiponectin secretion relative to the solvent control was estimated from the y-intercept, while the concentration of test material necessary for half maximal adiponectin secretion was computed from the negative value of the slope.

Figure 19:
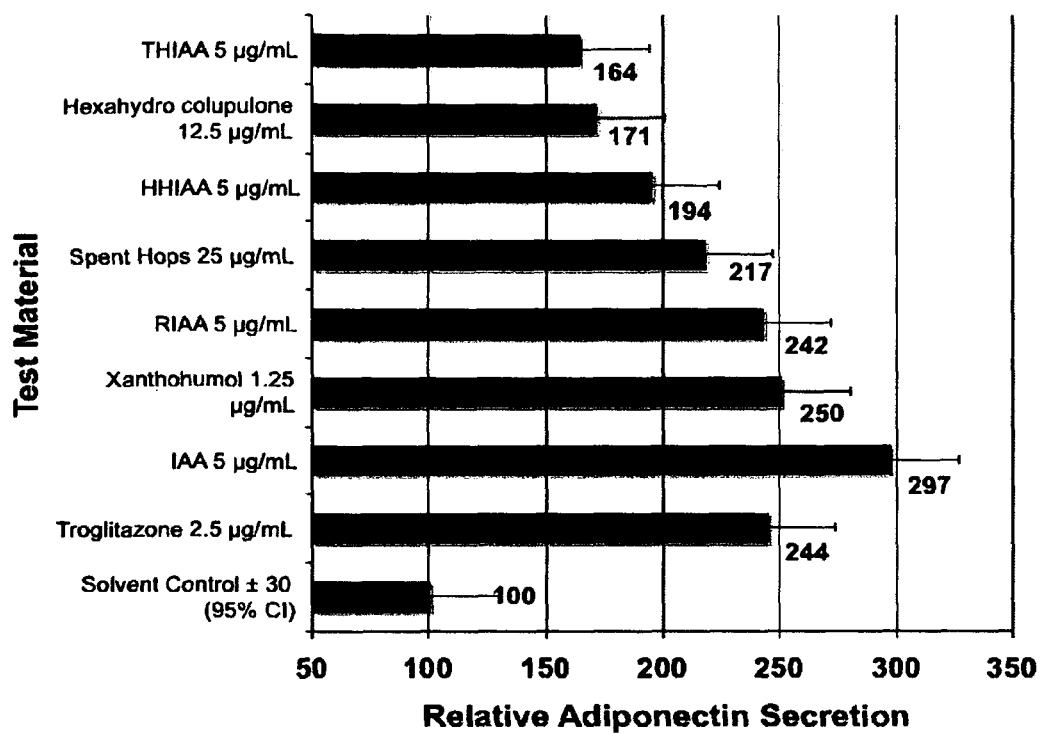
FIG. 19 is a representative bar graph of maximum adiponectin secretion by insulin-resistant 3T3-L1 cells in 24 hr elicited by the test material over four doses. Values presented are as a percent relative to the solvent control; error bars represent 95% confidence intervals. IAA=isoalpha acids, RIAA=Rho isoalpha acids, HHIA=hexahydroisoalpha acids, and THIAA=tetrahydroisoalpha acids.

Results—The positive control troglitazone maximally enhanced adiponectin secretion 2.44-fold at 2.5 µg/ml over the solvent control in insulin-resistant 3T3-L1 cells (FIG. 19). All hops phytochemicals tested demonstrated enhanced adiponectin secretion relative to the solvent control, with isoalpha acids producing significantly more adiponectin secretion than troglitazone (2.97-fold relative to controls). Of the four doses tested, maximal adiponectin secretion was observed at 5 µg/ml, the highest dose, for isoalpha acids, Rho isoalpha acids, hexahydroisoalpha acids and tetrahydroisoalpha acids. For xanthohumols, spent hops and hexahydro colupulone the maximum observed increase in adiponectin secretion was seen at 1.25, 25 and 12.5 µg/ml, respectively. Observed maximal relative adiponectin expression was comparable to troglitazone for xanthohumols, Rho isoalpha acids, and spent hops and less than troglitazone, but greater than control, for hexahydroisoalpha acids, hexahydro colupulone and tetrahydroisoalpha acids.

TABLE 20

Maximum adiponectin secretion and concentration of test material necessary for half maximal adiponectin secretion estimated, respectively, from the y-intercept and slope of Hofstee plots.

| Test Material | Maximum Adiponectin Secretion[1] [Fold relative to control] | Test Material at Half Maximal Secretion [µg/mL] |
|---|---|---|
| Isoalpha acids | 3.17 | 0.49 |
| Xanthohumol | 2.47 | 0.037 |
| Rho isoalpha acids | 2.38 | 0.10 |
| Troglitazone[2] | 2.29 | 0.085 |
| Spent hops | 2.21 | 2.8 |
| Hexahydroisoalpha acids[2] | 1.89 | 0.092 |
| Hexahydro colupulone[2] | 1.83 | 3.2 |
| Tetrahydroisoalpha acids | 1.60 | 0.11 |

Figure 20:
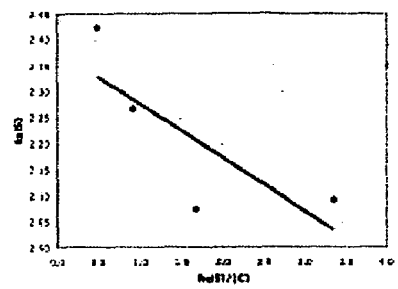
FIG. 20 depicts the Hofstee plots for Rho isoalpha acids, isoalpha acids, tetrahydroisoalpha acids, hexahydroisoalpha acids, xanthohumols, spent hops, hexahydrocolupulone and the positive control troglitazone. Maximum adiponectin secretion relative to the solvent control was estimated from the y-intercept, while the concentration of test material necessary for half maximal adiponectin secretion was computed from the negative value of the slope.
Figure 20:
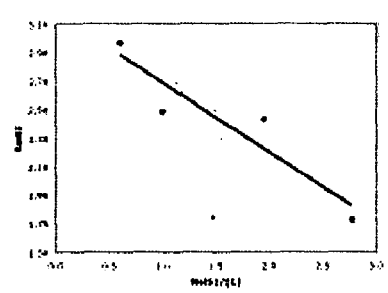
Figure 20:
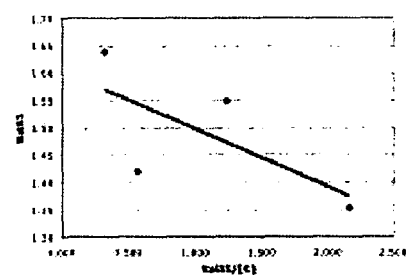
Figure 20:
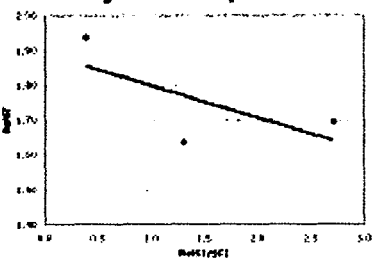
Figure 20:
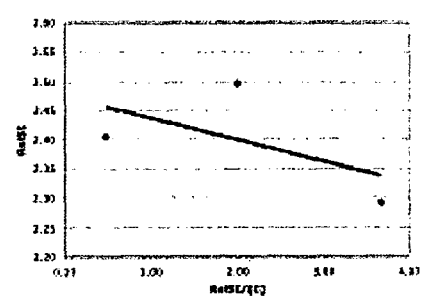
Figure 20:
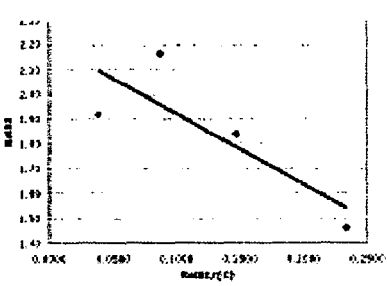
Figure 20:
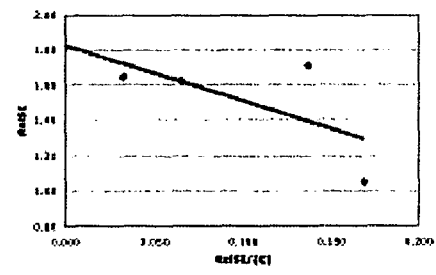
Figure 20:
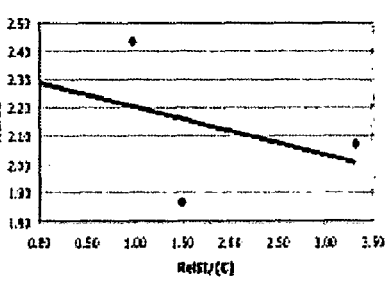

[1]Estimated from linear regression analysis of Hofstee plots using all four concentrations tested
[2]One outlier omitted and three concentrations used for dose-response estimates As seen in Table 20, estimates of maximal adiponectin secretion derived from modified Hofstee plots (FIG. 20) supported the observations noted above. y-Intercept estimates of maximum adiponectin secretion segregated roughly into three groups: (1) isoalpha acids, (2) xanthohumols, Rho isoalpha acids, troglitazone, and spent hops, and (3) hexahydroisoalpha acids, hexahydro colupulone and tetrahydroisoalpha acids. The concentration of test material required for stimulation of half maximal adiponectin secretion in insulin-resistant 3T3-L1 cells, approximately 0.1 µg/ml, was similar for troglitazone, Rho isoalpha acids, tetrahydroisoalpha acid and hexahydroisoalpha acids. The concentration of isoalpha acids at half maximal adiponectin secretion 0.49 µg/ml was nearly 5-fold greater. Xanthohumols exhibited the lowest dose for half maximal adiponectin secretion estimated at 0.037 µg/ml. The highest concentrations for the estimated half maximal adiponectin secretion variable were seen for spent hops and hexahydro colupulone, respectively, 2.8 and 3.2 µg/ml.

Based upon their ability to enhance adiponectin secretion in insulin-resistant 3T3-L1 cells, the positive hops phytochemical genera seen in this study, isoalpha acids, Rho-isoalpha acids, tetrahydroisoalpha acids, hexahydroisoalpha acids, xanthohumols, spent hops and hexahydro colupulone, may be expected to have a positive effect on all clinical pathologies in which plasma adiponectin concentrations are depressed.

Example 22

Hops Phytochemicals Exhibit Anti-Inflammatory Activity Through Enhanced Adiponectin Secretion and Inhibition of Interleukin-6 Secretion in Insulin-Resistant 3T3-L1 Adipocytes The Model—The 3T3-L1 murine fibroblast model as described in Example 11 was used in these experiments. Adiponectin and IL-6 were assayed as described, respectively in Examples 12 and 18. Standard chemicals, hops compounds RIAA, IAA, THIAA, HHIAA, xanthohumols, hexahydrocolupulone, spent hops were as described in Examples 12 and 20.

Statistical Calculations and Interpretation—All assays were preformed in duplicate. For statistical analysis, the effect of hops derivatives on adiponectin or IL-6 secretion was computed relative to the solvent control. Differences among the doses were determined using analysis of variance without correction for multiple comparisons; the nominal five percent probability of a type I error was selected.

Results—Troglitazone and all hops derivatives tested increased adiponectin secretion in the presence of high concentrations of insulin (Table 21). Troglitazone did not decrease IL-6 secretion in this model. In fact, troglitazone, and HHCL exhibited two concentrations in which IL-6 secretion was increased, while THIAA and spent hops increased IL-6 at the highest concentration and had no effect at the other concentrations. The effect of other hops derivatives on IL-6 secretion was generally biphasic. At the highest concentrations tested, RIAA, HHIAA, and XN increased IL-6 secretion; only IAA did not. Significant decreases in IL-6 secretion were noted for RIAA, IAA, THIAA, and XN.

TABLE 21

Effect of hops compounds on adiponectin and interleukin-6 secretion insulin-resistant 3T3-L1 adipocytes.

| Test Material | Concentration [µg/ml] | Adiponectin Index† | IL-6 Index†† | Adiponectin/IL-6 |
|---|---|---|---|---|
| Insulin control ± 95% CI | — | 1.00 ± 0.30* | 1.00 ± 0.23 | 1.00 ± 0.30 |
| Troglitazone | 5.00 | 1.47# | 1.31# | 1.12 |
|  | 2.50 | 2.44# | 1.06 | 2.30# |
|  | 1.25 | 1.87# | 1.46# | 1.28 |
|  | 0.625 | 2.07# | 1.00 | 2.07# |
| Rho isoalpha acids (RIAA) | 5.0 | 2.42# | 1.28# | 1.89# |
|  | 2.5 | 2.27# | 0.83 | 2.73# |
|  | 1.25 | 2.07# | 0.67# | 3.09# |
|  | 0.625 | 2.09# | 0.49# | 4.27# |
| Isoalpha acids (IAA) | 5.0 | 2.97# | 0.78 | 3.81# |
|  | 2.5 | 2.49# | 0.63# | 3.95# |
|  | 1.25 | 2.44# | 0.60# | 4.07# |
|  | 0.625 | 1.73# | 0.46# | 3.76# |

TABLE 21-continued

Effect of hops compounds on adiponectin and interleukin-6 secretion insulin-resistant 3T3-L1 adipocytes.

| Test Material | Concentration [μg/ml] | Adiponectin Index† | IL-6 Index†† | Adiponectin/IL-6 |
|---|---|---|---|---|
| Tetrahydro-isoalpha acids (THIAA) | 5.0 | 1.64# | 1.58# | 1.04 |
| | 2.5 | 1.42# | 0.89 | 1.60# |
| | 1.25 | 1.55# | 0.94 | 1.65# |
| | 0.625 | 1.35# | 0.80 | 1.69# |
| Hexahydro-isoalpha acids (HHIAA) | 5.0 | 1.94# | 1.49# | 1.30# |
| | 2.5 | 1.53# | 0.74# | 2.07# |
| | 1.25 | 1.64# | 0.67# | 2.45# |
| | 0.625 | 1.69# | 0.73# | 2.32# |
| Xanthohumols (XN) | 5.0 | 2.41# | 1.23# | 1.96# |
| | 2.5 | 2.11# | 0.96 | 2.20# |
| | 1.25 | 2.50# | 0.92 | 2.72# |
| | 0.625 | 2.29# | 0.64# | 3.58# |
| Hexahydro-colupulone (HHCL) | 50.0 | 1.65# | 2.77# | 0.60# |
| | 25.0 | 1.62# | 1.19 | 1.36# |
| | 12.5 | 1.71# | 0.94 | 1.82# |
| | 6.25 | 1.05 | 1.00 | 1.05 |
| Spent Hops | 50.0 | 1.92# | 1.58# | 1.22# |
| | 25.0 | 2.17# | 0.86 | 2.52# |
| | 12.5 | 1.84# | 1.03 | 1.79# |
| | 6.25 | 1.46# | 1.03 | 1.42# |

The *Acacia catechu* test material or indomethacin was added in concert with 166 nM insulin to D5 3T3-L1 adipocytes. On the following day, supernatant media were sampled for adiponectin, IL-6 and resistin determination. All values were indexed to the insulin only control.
†Adiponectin Index = [Adiponectin]$_{Test}$/[Adiponectin]$_{Insulin\ Control}$
††IL-6 Index = [IL-6$_{Test}$]/[IL-6$_{Insulin\ Control}$]
*Index value is mean ± 95% confidence interval computed from residual mean square of the analysis of variance. For adiponectin or adiponectin/IL-6, values <0.7 or >1.3 are significantly different from insulin control and for IL-6, values <0.77 or >1.23 are significantly different from insulin control.
Significantly different from insulin control p < 0.05.

The adiponectin/IL-6 ratio, a metric of overall anti-inflammatory effectiveness, was strongly positive (>2.00) for RIAA, IAA HHIA, and XN. THIAA, HHCL and spent hops exhibited positive, albeit lower, adiponectin/IL-6 ratios. For troglitazone the adiponectin/IL-6 ratio was mixed with a strongly positive response at 2.5 and 0.625 μg/ml and no effect at 5.0 or 1.25 μg/ml.

The data suggest that the pro-inflammatory effect of hyperinsulinemia can be attenuated in adipocytes by hops derivatives RIAA, IAA, HHIA, THIAA, XN, HHCL and spent hops. In general, the anti-inflammatory effects of hops derivatives in hyperinsulinemia conditions hyperinsulinemia uncomplicated by TNFα were more consistent than those of troglitazone.

Example 23

Hops Phytochemicals Increase Adiponectin Secretion in TNFα-Treated 3T3-L1 Adipocytes The Model—The 3T3-L1 murine fibroblast model as described in Example 11 was used in these experiments. Standard chemicals and hops compounds IAA, RIAA, HHIAA, and THIAA, were as described, respectively, in Examples 13 and 20. Hops derivatives were tested at concentrations of 0.625, 1.25, 2.5, and 5.0 μg/ml. Adiponectin was assayed as described in Example 12.

Figure 21:
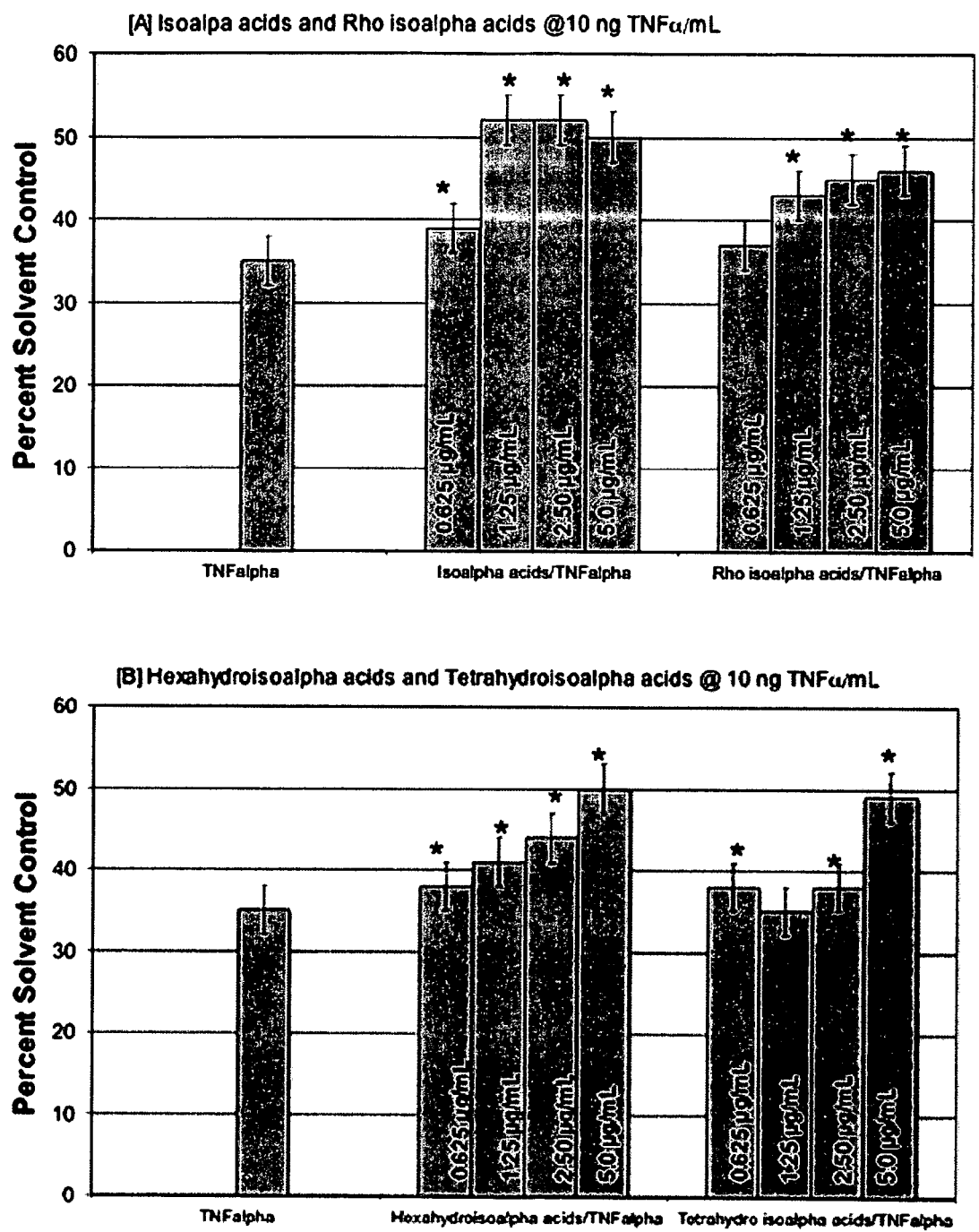
FIG. 21 displays two bar graphs representing relative adiponectin secretion by TNFα-treated, mature 3T3-L1 cells elicited by isoalpha acids and Rho isoalpha acids [panel A], and hexahydro isoalpha acids and tetrahydro isoalpha acids [panel B]. Values presented are percent relative to the solvent control; error bars represent 95% confidence intervals. *Significantly different from TNFα only treatment ($p<0.05$).

Results—Overnight treatment of day 5 (D5) 3T3-L1 adipocytes with 10 ng TNFα/ml markedly suppressed adiponectin secretion (FIG. 21). The hops derivatives IAA, RIAA, HHIAA and THIAA all increased adiponectin secretion relative to the TNFα/solvent control. Linear dose-response curves were observed with RIAA and HHIAA resulting in maximal inhibition at the highest concentration tested 5.0 μg/ml. IAA elicited maximal secretion of adiponectin at 1.25 μg/ml, while THIAA exhibited a curvilinear response with maximal adiponectin secretion at 5.0 μg/ml.

The ability of hops derivatives IAA, RIAA, HHIAA and THIAA to increase adipocyte adiponectin secretion in the presence of supraphysiological concentrations of TNFα supports the usefulness of these compounds in the prevention or treatment of inflammatory conditions involving suboptimal adipocyte functioning.

Example 24

*Acacia catechu* Formulation Synergistic Interaction with Hops Derivatives to Alter Lipogenesis and Adiponectin Secretion in 3T3-L1 Adipocytes The Model—The 3T3-L1 murine fibroblast model as described in Examples 11 and 13 was used in these experiments.

Test Chemicals and Treatment—Standard chemicals used were as noted in Examples 11 and 13. 3T3-L1 adipocytes were treated prior to differentiation as in Example 11 for computing the lipogenic index or with TNFα as described in Example 12 for assessing the adiponectin index. *Acacia catechu* sample #5669 as described in Example 14 was used with hops derivatives Rho-isoalpha acids and isoalpha acids as previously described. *Acacia catechu* and the 5:1 and 10:1 combinations of *Acacia*:RIAA and *Acacia*:IAA were tested at 50, 10, 5.0 and 1.0 μg/ml. RIAA and IAA were tested independently at 5.0, 2.5, 1.25 and 0.625 μg/ml.

Calculations—Estimates of expected lipogenic response and adiponectin secretion of the *Acacia*/hops combinations and determination of synergy were made as previously described.

Results—All combinations tested exhibited lipogenic synergy at one or more concentrations tested (Table 22). *Acacia*:RIAA combinations were generally more active than the *Acacia*:IAA combinations with *Acacia*:RIAA [5:1] demonstrating synergy at all doses and *Acacia*:RIAA [10:1] synergistic at 10 and 5.0 μg/ml and not antagonistic at any concentration tested. The *Acacia*:IAA [10:1] combination was also synergistic at the two mid-doses and showed no antagonism. While *Acacia*:IAA [5:1] was synergistic at the 50 μg/ml concentration, it was antagonistic at the 5.0 μg/ml dose.

Similarly, all combinations demonstrated synergy with respect to increasing adiponectin secretion at one or more concentrations tested (Table 23). *Acacia*:IAA [10:1] exhibited synergy at all doses, while *Acacia*:RIAA [5:1] and *Acacia*:RIAA [10:1] were synergistic at three doses and antagonistic at one concentration. The *Acacia*:IAA [5:1] combination was synergistic at 1.0 μg/ml and antagonistic at the higher 10 μg/ml.

TABLE 22

Observed and expected lipogenic response elicited by *Acacia catechu* and hops derivatives in the insulin-resistant 3T3-l model.

| Test Material | Concentration [μg/ml] | Lipogenic Index† | | |
|---|---|---|---|---|
| | | Observed | Expected | Result |
| *Acacia*/RIAA [5:1][1] | 50 | 1.05 | 0.98 | Synergy |
| | 10 | 0.96 | 0.89 | Synergy |
| | 5.0 | 0.93 | 0.90 | Synergy |
| | 1.0 | 0.92 | 0.89 | Synergy |
| *Acacia*/IAA [5:1][2] | 50 | 1.06 | 0.98 | Synergy |
| | 10 | 0.93 | 0.95 | No effect |

TABLE 22-continued

Observed and expected lipogenic response elicited by *Acacia catechu* and hops derivatives in the insulin-resistant 3T3-1 model.

| Test Material | Concentration [μg/ml] | Lipogenic Index† Observed | Expected | Result |
|---|---|---|---|---|
| | 5.0 | 0.90 | 0.98 | Antagonism |
| | 1.0 | 0.96 | 0.98 | No effect |
| Acacia/RIAA [10:1][3] | 50 | 0.99 | 1.03 | No effect |
| | 10 | 1.00 | 0.90 | Synergy |
| | 5.0 | 1.00 | 0.90 | Synergy |
| | 1.0 | 0.94 | 0.89 | No effect |
| Acacia/IAA [10:1][4] | 50 | 1.37 | 1.29 | Synergy |
| | 10 | 1.16 | 1.15 | No effect |
| | 5.0 | 1.08 | 1.09 | No effect |
| | 1.0 | 1.00 | 0.99 | No effect |

†Lipogenic Index = [OD]$_{Test}$/[OD]$_{DMSO\ control}$.
[1]Upper 95% confidence limit is 1.03 with least significant difference = 0.03.
[2]Upper 95% confidence limit is 1.03 with least significant difference = 0.03
[3]Upper 95% confidence limit is 1.07 with least significant difference = 0.07.
[4]Upper 95% confidence limit is 1.02 with least significant difference = 0.02.

TABLE 23

Observed and expected adiponectin secretion elicited by *Acacia catechu* and hops derivatives in the TNFα/3T3-1 model.

| Test Material | Concentration [μg/ml] | Adiponectin Index† Observed | Expected | Result |
|---|---|---|---|---|
| Acacia/RIAA [5:1][1] | 50 | 1.27 | 1.08 | Synergy |
| | 10 | 0.99 | 1.25 | Antagonism |
| | 5.0 | 1.02 | 0.92 | Synergy |
| | 1.0 | 1.19 | 1.07 | Synergy |
| Acacia/IAA [5:1][1] | 50 | 1.13 | 1.16 | No effect |
| | 10 | 0.92 | 1.13 | Antagonism |
| | 5.0 | 1.04 | 1.09 | No effect |
| | 1.0 | 1.25 | 1.13 | Synergy |
| Acacia/RIAA [10:1][2] | 50 | 1.29 | 1.11 | Synergy |
| | 10 | 1.07 | 0.95 | Synergy |
| | 5.0 | 0.94 | 1.06 | Antagonism |
| | 1.0 | 1.03 | 0.94 | Synergy |
| Acacia/IAA [10:1][2] | 50 | 1.28 | 0.82 | Synergy |
| | 10 | 1.12 | 1.07 | Synergy |
| | 5.0 | 1.11 | 0.99 | Synergy |
| | 1.0 | 1.30 | 1.05 | Synergy |

†Adiponectin Index = [Adiponectin]$_{Test}$/[Adiponectin]$_{TNF\alpha\ control}$
[1]Upper 95% confidence limit is 1.07 with least significant difference = 0.07.
[2]Upper 95% confidence limit is 1.03 with least significant difference = 0.03

Combinations of *Acacia catechu* and the hops derivatives Rho isoalpha acids or isoalpha acids exhibit synergistic combinations and only few antagonistic combinations with respect to increasing lipid incorporation in adipocytes and increasing adiponectin secretion from adipocytes.

Example 25

Anti-Inflammatory Activity of Hops Derivatives in the Lipopolysaccharide/3T3-L1 Adipocyte Model The Model—The 3T3-L1 murine adipocyte model as described in Examples 11 and 13 was used in these experiments.

Test Chemicals and Treatment—Standard chemicals were as noted in Examples 11 and 13, however, 100 ng/ml of bacterial lipopolysaccharide (LPS, Sigma, St. Louis, Mo.) was used in place of TNFα on D5. Hops derivatives Rho-isoalpha acids and isoalpha acids used were as described in Example 20. The non-steroidal anti-inflammatory drugs (NSAIDs) aspirin, salicylic acid, and ibuprofen were obtained from Sigma. The commercial capsule formulation of celecoxib (Celebrex™, G.D. Searle & Co. Chicago, Ill.) was used and cells were dosed based upon content of active ingredient. Hops derivatives, ibuprofen, and celecoxib were dosed at 5.00, 2.50, 1.25 and 0.625 μg/ml. Indomethacin, troglitazone, and pioglitazone were tested at 10, 5.0, 1.0 and 0.50 μg/ml. Concentrations for aspirin were 100, 50.0, 25.0 and 12.5 μg/ml, while those for salicylic acid were 200, 100, 50.0 and 25.0 μg/ml. IL-6 and adiponectin were assayed and data were analyzed and tabulated as previously described in Example 18 for IL-6 and Example 13 for adiponectin.

Results—LPS provided a 12-fold stimulation of IL-6 in D5 adipocytes. All test agents reduced IL-6 secretion by LPS-stimulated adipocytes to varying degrees. Maximum inhibition of IL-6 and concentrations for which this maximum inhibition were observed are presented in Table 24. Due to a relatively large within treatment variance, the extent of maximum inhibition of IL-6 did not differ among the test materials. The doses for which maximum inhibition occurred, however, did differ considerably. The rank order of potency for IL-6 inhibition was ibuprofen>RIAA= IAA> celecoxib>pioglitazone=indomethacin>troglitazone>aspirin> salicylic acid. On a qualitative basis, indomethacin, troglitazone, pioglitazone, ibuprofen and celecoxib inhibited IL-6 secretion at all concentrations tested, while RIAA, IAA, and aspirin did not significantly inhibit IL-6 at the lowest concentrations (data not shown).

LPS treatment of D5 3T3-L1 adipocytes decreased adiponectin secretion relative to the DMSO control (Table 25). Unlike IL-6 inhibition in which all test compounds inhibited secretion to some extent, aspirin, salicylic acid and celecoxib failed to induce adiponectin secretion in LPS-treated 3T3-L1 adipocytes at any of the does tested. Maximum adiponectin stimulation of 15, 17, 20 and 22% was observed, respectively, for troglitazone, RIAA, IAA and ibuprofen at 0.625 μg/ml. Pioglitazone was next in order of potency with adiponectin stimulation of 12% at 1.25 μg/ml. With a 9% stimulation of adiponectin secretion at 2.50 μg/ml, indomethacin was least potent of the active test materials.

In the LPS/3T3-L1 model, hops derivatives RIAA and IAA as well as ibuprofen decreased IL-6 secretion and increased adiponectin secretion at concentrations likely to be obtained in vivo. The thiazolidinediones troglitazone and pioglitazone were less potent as inhibitors of IL-6 secretion, requiring higher doses than hops derivatives, but similar to hops derivatives with respect to adiponectin stimulation. No consistent relationship between anti-inflammatory activity in macrophage models and the adipocyte model was observed for the NSAIDs indomethacin, aspirin, ibuprofen and celecoxib.

TABLE 24

Maximum inhibition of IL-6 secretion in LPS/3T3-L1 adipocytes by hops derivatives and selected NSAIDs

| Test Material | Concentration [μg/ml] | IL-6 Index† | % Inhibition |
|---|---|---|---|
| DMSO control | — | 0.09* | 91* |
| LPS control ± 95% CI | — | 1.00 ± 0.30 | 0 |
| Indomethacin | 5.00 | 0.47* | 53* |
| Troglitazone | 10.0 | 0.31* | 69* |
| Pioglitazone | 5.00 | 0.37* | 63* |
| Rho-isoalpha acids | 1.25 | 0.63* | 37* |
| Isoalpha acids | 1.25 | 0.61* | 39* |
| Aspirin | 25.0 | 0.61* | 39* |
| Salicylic acid | 50.0 | 0.52* | 48* |

TABLE 24-continued

Maximum inhibition of IL-6 secretion in LPS/3T3-L1 adipocytes by hops derivatives and selected NSAIDs

| Test Material | Concentration [μg/ml] | IL-6 Index† | % Inhibition |
|---|---|---|---|
| Ibuprofen | 0.625 | 0.46* | 54* |
| Celecoxib | 2.50 | 0.39* | 61* |

The test materials were added in concert with 100 ng LPS/ml to D5 3T3-L1 adipocytes. On the following day, supernatant media were sampled for IL-6 determination. All values were indexed to the LPS control as noted below. Concentrations presented represent dose providing the maximum inhibition of IL-6 secretion and those values less than 0.70 are significantly ($p < 0.05$) less than the LPS control.
†IL-6 Index = [IL-6$_{Test}$ − IL-6$_{Control}$]/[IL-6$_{LPS}$ − IL-6$_{Control}$]
*Significantly different from LPS control $p < 0.05$).

TABLE 25

Maximum stimulation of adiponectin secretion in LPS/3T3-L1 adipocytes by hops derivatives and selected NSAIDs

| Test Material | Concentration [μg/ml] | Adiponectin Index† | % Stimulation |
|---|---|---|---|
| DMSO control | — | 1.24 | |
| LPS control ± 95% CI | — | 1.00 | |
| Indomethacin | 2.50 | 1.09* | 9 |
| Troglitazone | 0.625 | 1.15* | 15 |
| Pioglitazone | 1.25 | 1.12* | 12 |
| Rho-isoalpha acids | 0.625 | 1.17* | 17 |
| Isoalpha acids | 0.625 | 1.20* | 20 |
| Aspirin | 113 | 1.02 | NS |
| Salicylic acid | 173 | 0.96 | NS |
| Ibuprofen | 0.625 | 1.22* | 22 |
| Celecoxib | 5.00 | 1.05 | NS |

†Adiponectin Index = [Adiponectin]$_{Test}$/[Adiponectin]$_{LPS\ control}$
*Values greater than 1.07 are significantly different from LPS control $p < 0.05$).
NS = not significantly different from the LPS control.

Example 26

Synergy of *Acacia catechu* or Hops Derivatives in Combination with Curcumin or Xanthohumols in the TNFα/3T3-1 Model The Model—The 3T3-L1 murine fibroblast model as described in Examples 11 and 13 was used in these experiments.

Test Chemicals and Treatment—Standard chemicals used were as noted in Example 11 and 13. 3T3-L1 adipocytes were stimulated with TNFα as described in Example 13 for assessing the adiponectin index. *Acacia catechu* sample #5669 as described in Example 14, hops derivatives Rho-isoalpha acids and xanthohumol as described in Example 20, and curcumin as provided by Metagenics (Gig Harbor, Wash.) and were used in these experiments. *Acacia catechu* and the 5:1 combinations of *Acacia*:curcumin and *Acacia*:xanthohumol were tested at 50, 10, 5.0 and 1.0 μg/ml. RIAA and the 1:1 combinations with curcumin and XN were tested at 10, 5, 1.0 and 0.50 μg/ml.

Calculations—Estimates of expected adiponectin index of the combinations and determination of synergy were made as described previously.

Results—TNFα reduced adiponectin secretion to about 50 percent of solvent only controls. The positive control pioglitazone increased adiponectin secretion by 80 percent (Table 26). Combinations of *Acacia* with curcumin or XN proved to be antagonistic at the higher concentrations and synergistic at the lower concentrations. Similarly, RIAA and curcumin were antagonistic at the three higher doses, but highly synergistic at the lowest dose 1.0 μg/ml. The two hops derivative RIAA and XN did not demonstrate synergy in adiponectin secretion from TNFα-stimulated 3T3-L1 cells.

In TNFα-treated 3T3-L1 adipocytes, both *Acacia* and RIAA synergistically increased adiponectin secretion, while only *Acacia* demonstrated synergy with XN.

TABLE 26

Synergy of *Acacia catechu* and hops derivatives in combinations with curcumin or xanthohumols in the TNFα/3T3-1 model.

| | Concentration | Adiponectin Index† | | |
|---|---|---|---|---|
| Test Material | [μg/ml] | Observed | Expected | Interpretation |
| DMSO Control | — | 2.07 | — | — |
| TNFα ± 95% CI | — | 1.0 ± 0.049 | — | — |
| Pioglitazone | 1.0 | 1.80 | — | — |
| Acacia/ | 50 | 0.56 | 0.94 | Antagonism |
| Curcumin | 10 | 1.01 | 1.07 | Antagonism |
| [5:1]$^1$ | 5.0 | 1.19 | 1.02 | Synergy |
| | 1.0 | 1.22 | 1.16 | Synergy |
| Acacia/XN | 50 | 0.54 | 0.85 | Antagonism |
| [5:1]$^1$ | 10 | 0.95 | 1.06 | Antagonism |
| | 5.0 | 0.97 | 1.01 | Antagonism |
| | 1.0 | 1.26 | 1.15 | Synergy |
| RIAA/ | 5 | 0.46 | 0.79 | Antagonism |
| Curcumin | 1 | 1.03 | 1.11 | Antagonism |
| [1:1]$^1$ | 5.0 | 1.12 | 1.28 | Antagonism |
| | 1.0 | 1.30 | 1.08 | Synergy |
| RIAA/XN | 50 | 0.31 | 0.63 | Antagonism |
| [1:1]$^1$ | 10 | 0.81 | 1.06 | Antagonism |
| | 5.0 | 1.09 | 1.25 | Antagonism |
| | 1.0 | 1.09 | 1.06 | No effect |

†Adiponectin Index = [Adiponectin]$_{Test}$/[Adiponectin]$_{TNFα\ control}$
$^1$95% confidence limits are 0.961 to 1.049 with least significant difference = 0.049.

Example 27

In Vitro Synergy of Lipogenesis by Conjugated Linoleic Acid in Combination with Hops Derivative Rho-Isoalpha Acids in the Insulin-Resistant 3T3-L1 Adipocyte Model The Model—The 3T3-L1 murine fibroblast model as described in Examples 11 and 13 was used in these experiments.

Test Chemicals and Treatment—Standard chemicals used were as noted in Example 11. 3T3-L1 adipocytes were treated prior to differentiation as in Example 11 for computing the lipogenic index. Powdered CLA was obtained from Lipid Nutrition (Channahon, Ill.) and was described as a 1:1 mixture of the c9t11 and t10c12 isomers. CLA and the 5:1 combinations of CLA:RIAA were tested at 50, 10, 5.0 and 1.0 μg/ml. RIAA was tested at 10, 1.0 and 0.1 μg/ml for calculation of expected lipogenic index as described previously.

Results—RIAA synergistically increased triglyceride content in combination with CLA. Synergy was noted at all does (Table 27).

Synergy between CLA and RIAA was observed over a wide range of doses and potentially could be used to increase the insulin sensitizing potency of CLA.

TABLE 27

Synergy of lipogenesis by conjugated linoleic acid in combination Rho-isoalpha acids in the insulin-resistant 3T3-L1 adipocyte model.

| Test Material | Concentration [μg/ml] | Lipogenic Index† Observed | Expected | Interpretation |
|---|---|---|---|---|
| CLA:RIAA [5:1][1] | 50 | 1.26 | 1.15 | Synergy |
| | 10 | 1.16 | 1.06 | Synergy |
| | 5.0 | 1.16 | 1.10 | Synergy |
| | 1.0 | 1.17 | 1.06 | Synergy |

†Lipogenic Index = $[OD]_{Test}/[OD]_{DMSO\ control}$.
[1]Upper 95% confidence limit is 1.05 with least significant difference = 0.05.

Example 28

Hops Phytochemicals Inhibit NF-kB Activation in TNFα-Treated 3T3-L1 Adipocytes The Model—The 3T3-L1 murine fibroblast model as described in Example 11 was used in these experiments.

Cell Culture and Treatment—Following differentiation 3T3-L1 adipocytes were maintained in post-differentiation medium for an additional 40 days. Standard chemicals, media and hops compounds RIAA and xanthohumol were as described in Examples 13 and 20. Hops derivatives and the positive control pioglitazone were tested at concentrations of 2.5, and 5.0 μg/ml. Test materials were added 1 hour prior to and nuclear extracts were prepared three and 24 hours following treatment with TNFα.

ELISA—3T3-L1 adipocytes were maintained in growth media for 40 days following differentiation. Nuclear NF-kBp65 was determined using the TransAM™ NF-kB kit from Active Motif (Carlsbad, Calif.) was used with no modifications. Jurkat nuclear extracts provided in the kit were derived from cells cultured in medium supplemented with 50 ng/ml TPA (phorbol, 12-myristate, 13 acetate) and 0.5 μM calcium ionophore A23187 for two hours at 37° C. immediately prior to harvesting.

Protein assay—Nuclear protein was quantified using the Active Motif Fluorescent Protein Quantification Kit.

Statistical Analysis—Comparisons were performed using a one-tailed Student's t-test. The probability of a type I error was set at the nominal five percent level.

Figure 22:
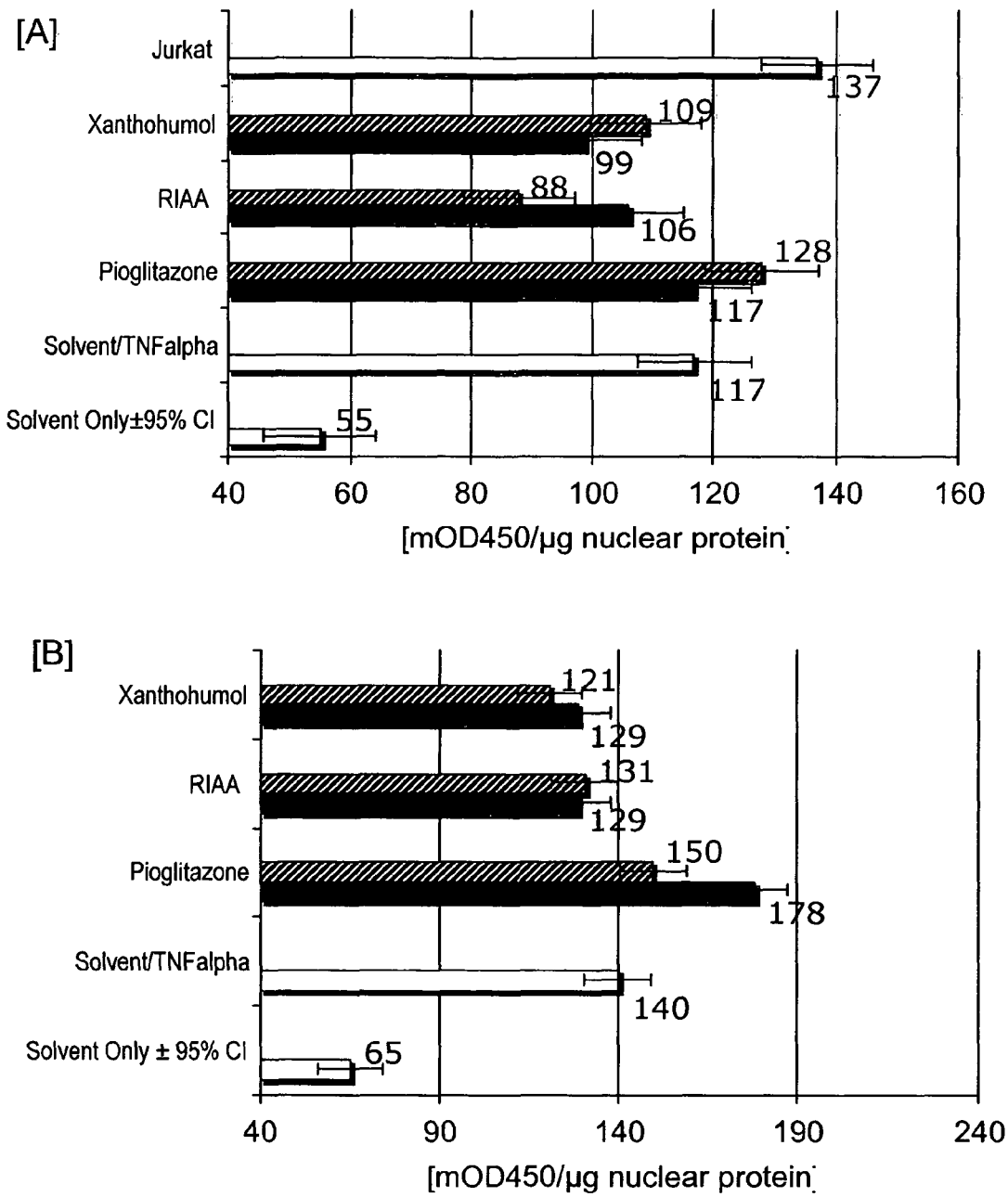
FIG. 22 depicts NF-kB nuclear translocation in insulin-resistant 3T3-L1 adipocytes [panel A] three and [panel B] 24 hr following addition of 10 ng TNFα/ml. Pioglitazone, RIAA and xanthohumols were added at 5.0 (black bars) and 2.5 (stripped bars) μg/ml. Jurkat nuclear extracts from cells cultured in medium supplemented with 50 ng/ml TPA (phorbol, 12-myristate, 13 acetate) and 0.5 μM calcium ionophore A23187 (CI) for two hours at 37° C. immediately prior to harvesting.

Results—The TPA-treated Jurkat nuclear extract exhibited the expected increase in NF-kBp65 indicating adequate performance of kit reagents (FIG. 22). Treatment of D40 3T3-L1 adipocytes with 10 ng TNFα/ml for three (FIG. 22A) or 24 hours (FIG. 22B), respectively, increased nuclear NF-kBp65 2.1- and 2.2-fold. As expected, the PPARγ agonist pioglitazone did not inhibit the amount of nuclear NF-kBp65 at either three or 24 hours following TNFα treatment. Nuclear translocation of NF-kBp65 was inhibited, respectively, 9.4 and 25% at 5.0 and 2.5 μg RIAA/ml at three hours post TNFα. At 24 hours, only the 5.0 RIAA/ml treatment exhibited significant ($p<0.05$) inhibition of NF-kBp65 nuclear translocation. Xanthohumols inhibited nuclear translocation of NF-kBp65, respectively, 15.6 and 6.9% at 5.0 and 2.5 μg/ml at three hours post-TNFα treatment and 13.4 and 8.0% at 24 hours.

Both RIAA and xanthohumols demonstrated consistent, albeit small, inhibition of nuclear translocation of NF-kBp65 in mature, insulin-resistant adipocytes treated with TNFα. This result differs from that described for PPARγ agonists, which have not been shown to inhibit nuclear translocation of NF-kBp65 in 3T3-L1 adipocytes.

Example 29

Acacia catechu Extract and Metformin Synergistically Increase Triglyceride Incorporation in Insulin Resistant 3T3-L1 Adipocytes The Model—The 3T3-L1 murine fibroblast model as described in Example 11 was used in these experiments. All chemicals and procedures used were as described in Example 11.

Test Chemicals and Treatment—Metformin was obtained from Sigma (St. Louis, Mo.). Test materials were added in dimethyl sulfoxide at Day 0 of differentiation and every two days throughout the maturation phase (Day 6/7). As a positive control, troglitazone was added to achieve a final concentration of 4.4 μg/ml. Metformin, Acacia catechu sample #5669 and the metformin/Acacia combination of 1:1 (w/w) were tested at 50 μg test material/ml. Differentiated 3T3-L1 cells were stained with 0.2% Oil Red O. The resulting stained oil droplets were dissolved with isopropanol and quantified by spectrophotometric analysis at 530 nm. Results were represented as a relative triglyceride content of fully differentiated cells in the solvent controls.

Calculations—An estimate of the expected adipogenic effect of the metformin/Acacia catechu extract was made using the relationship: 1/LI=X/LIx+Y/LIy, where LI=the lipogenic index, X and Y were the relative fractions of each component in the test mixture and X+Y=1. Synergy was inferred if the mean of the estimated LI fell outside of the 95% confidence interval of the estimate of the corresponding observed fraction. This definition of synergy, involving comparison of the effects of a combination with that of each of its components, was described by Berenbaum [Berenbaum, M. C. What is synergy? Pharmacol Rev 41(2), 93-141, (1989)].

Figure 23:
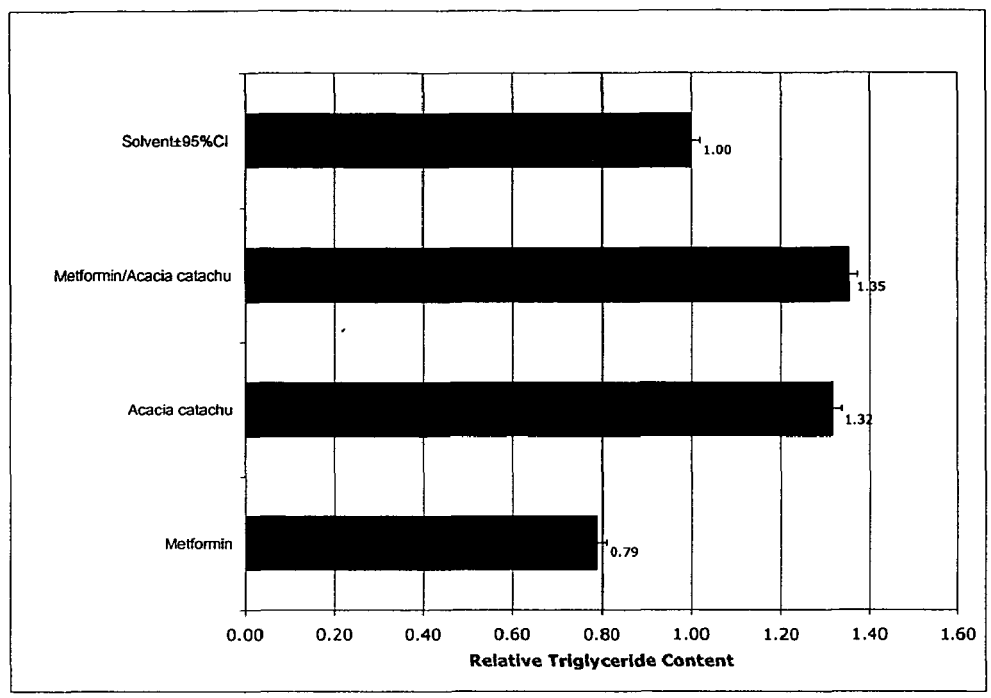
FIG. 23 graphically describes the relative triglyceride content of insulin resistant 3T3-L1 cells treated with solvent, metformin, an *Acacia* sample #5659 aqueous extract or a 1:1 combination of metformin/*Acacia catechu* extract. Results are represented as a relative triglyceride content of fully differentiated cells in the solvent controls.

Results—The Acacia catechu extract was highly lipogenic, increasing triglyceride content of the 3T3-L1 cells by 32 percent (FIG. 23) yielding a lipogenic index of 1.32. With a lipogenic index of 0.79, metformin alone was not lipogenic. The metformin/Acacia catechu extract combination demonstrated an observed lipogenic index of 1.35. With an expected lipogenic index of 98, the metformin/Acacia catechu extract demonstrated synergy as the observed lipogenic index fell outside of the two percent 95% upper confidence limit for the expected value.

Based upon the lipogenic potential demonstrated in 3T3-L1 cells, 1:1 combinations of metformin and Acacia catechu extract would be expected to behave synergistically in clinical use. Such combinations would be useful to increase the range of positive benefits of metformin therapy such as decreasing plasma triglycerides or extending the period of metformin efficacy.

Example 30

In Vitro Synergies of Lipogenesis by Hops Derivatives and Thiazolidinediones in the Insulin-Resistant 3T3-L1 Adipocyte Model The Model—The 3T3-L1 murine fibroblast model as described in Examples 11 and 13 was used in these experiments.

Test Chemicals and Treatment—Standard chemicals used were as noted in Example 11. 3T3-L1 adipocytes were treated prior to differentiation as in Example 11 for computing the lipogenic index. Troglitazone was obtained from Cayman Chemicals (Chicago, Ill.). Pioglitazone was obtained as the commercial, tableted formulation (ACTOSE®, Takeda Pharmaceuticals, Lincolnshire, Ill.). The tablets were crushed and the whole powder was used in the assay. All results were computed based upon active ingredient content. Hops derivatives Rho-isoalpha acids and isoalpha acids used were as described in Example 20. Troglitazone in combination with RIAA and IAA was tested at 4.0 μg/ml, while the more potent pioglitazone was tested in 1:1 combinations with RIAA and IAA at 2.5 μg/ml. All materials were also tested independently at 4.0 and 2.5 μg/ml for calculation of expected lipogenic index as described in Example 34.

Results—When tested at 4.0 and 2.5 μg/ml, respectively, with troglitazone or piroglitazone, both Rho-isoalpha acids and isoalpha acids increased triglyceride synthesis synergistically with the thiazolidinediones in the insulin-resistant 3T3-L1 adipocyte model (Table 28).

Hops derivatives Rho-isoalpha acids and isoalpha acids could synergistically increase the insulin sensitizing effects of thiazolidinediones resulting in potential clinical benefits of dose-reduction or increased numbers of patients responding favorably.

TABLE 28

In vitro synergies of hops derivatives and thiazolidinediones in the insulin-resistant 3T3-L1 adipocyte model.

| Test Material | Concentration [μg/ml] | Lipogenic Index† Observed | Lipogenic Index† Expected | Interpretation |
|---|---|---|---|---|
| Troglitazone/RIAA [1:1][1] | 4.0 | 1.23 | 1.06 | Synergy |
| Troglitazone/IAA [1:1][1] | 4.0 | 1.14 | 1.02 | Synergy |
| Pioglitazone/RIAA [1:1][2] | 2.5 | 1.19 | 1.00 | Synergy |
| Pioglitazone/IAA [1:1][2] | 2.5 | 1.16 | 0.95 | Synergy |

†Lipogenic Index = $[OD]_{Test}/[OD]_{DMSO\ control}$.
[1]Upper 95% confidence limit is 1.02 with least significant difference = 0.02.
[2]Upper 95% confidence limit is 1.05 with least significant difference = 0.05.

Example 31

In Vitro Synergies of Rho-Isoalpha Acids and Metformin in the TNFα/3T3-L1 Adipocyte Model The Model—The 3T3-L1 murine fibroblast model as described in Example 11 was used in these experiments. Standard chemicals used and treatment of adipocytes with 10 ng TNFα/ml were as noted, respectively, in Examples 11 and 13.

Test Materials and Cell Treatment—Metformin was obtained from Sigma (St. Louis, Mo.) and Rho-isoalpha acids were as described in Example 20. Metformin at 50, 10, 5.0 or 1.0 μg/ml without or with 1 μg RIAA/ml was added in concert with 10 ng TNFα/ml to D5 3T3-L1 adipocytes. Culture supernatant media were assayed for IL-6 on Day 6 as detailed in Example 11. An estimate of the expected effect of the metformin:RIAA mixtures on IL-6 inhibition was made as previously described.

Results—TNFα provided a six-fold increase in IL-6 secretion in D5 adipocytes. Troglitazone at 1 μg/ml inhibited IL-6 secretion 34 percent relative to the controls, while 1 μg RIAA inhibited IL-6 secretion 24 percent relative to the controls (Table 29). Metformin in combination with 1 μg RIAA/ml demonstrated synergy at the 50 μg/ml concentration and strong synergy at the 1 μg/ml concentration. At 50 μg metformin/ml, 1 μg RIAA provided an additional 10 percent inhibition in the mixture; while at 1 μg metformin, 1 μg RIAA increased IL-6 inhibition by 35 percent. Antagonism and no effect, respectively, were seen of the metformin:RIAA combinations at the two mid-doses.

Combinations of metformin and Rho-isoalpha acids function synergistically at both high and low concentrations to reduce IL-6 secretion from TNFα-treated 3T3-L1 adipocytes.

TABLE 29

Synergistic inhibition of IL-6 secretion in TNFα/3T3-L1 adipocytes by hops Rho-isoalpha acids and metformin.

| Test Material | Concentration [μg/ml] | IL-6 Index† | % Inhibition | Interpretation |
|---|---|---|---|---|
| DMSO control | — | 0.16 | — | — |
| TNFα control ± 95% CI | — | 1.00 ± 0.07* | 0 | — |
| Troglitazone | 1.0 | 0.66 | 34 | — |
| RIAA | 1.0 | 0.76 | 24 | — |
| Metformin | 50 | 0.78 | 22 | — |
| Metformin/1 μg RIAA | 50 | 0.68 | 32 | Synergy |
| Metformin | 10 | 0.78 | 22 | — |
| Metformin/1 μg RIAA | 10 | 0.86 | 14 | Antagonism |
| Metformin | 5.0 | 0.96 | 4 | — |
| Metformin/1 μg RIAA | 5.0 | 0.91 | 9 | No effect |
| Metformin | 1.0 | 0.91 | 9 | — |
| Metformin/1 μg RIAA | 1.0 | 0.56 | 44 | Synergy |

The test materials were added in concert with 10 ng TNFα/ml to D5 3T3-L1 adipocytes at the stated concentrations. On the following day, supernatant media were sampled for IL-6 determination. All values were indexed to the TNFα control.
†IL-6 Index = $[IL\text{-}6_{Test} - IL\text{-}6_{Control}]/[IL\text{-}6_{TNF\alpha} - IL\text{-}6_{Control}]$
*Values less than 0.93 are significantly (p < 0.05) less than the TNFα control.

Example 32

Effects of Test Compounds on Cancer Cell Proliferation in vitro

This experiment demonstrates the direct inhibitory effects on cancer cell proliferation in vitro for a number of test compounds of the instant invention.

Methods—The inhibitory effects of test compounds of the present invention on cancer cell proliferation were examined in the RL 95-2 endometrial cancer cell model (an over expresser of AKT kinase), and in the HT-29 (constitutively expressing COX-2) and SW480 (constitutively expressing activated AKT kinase) colon cancer cell models. Briefly, the target cells were plated into 96 well tissue culture plates and allowed to grow until subconfluent. The cells were then treated for 72 hours with various amounts of the test compounds as described in Example 4 and relative cell proliferation determined by the CyQuant (Invitrogen, Carlsbad, Calif.) commercial fluorescence assay.

Figure 24:
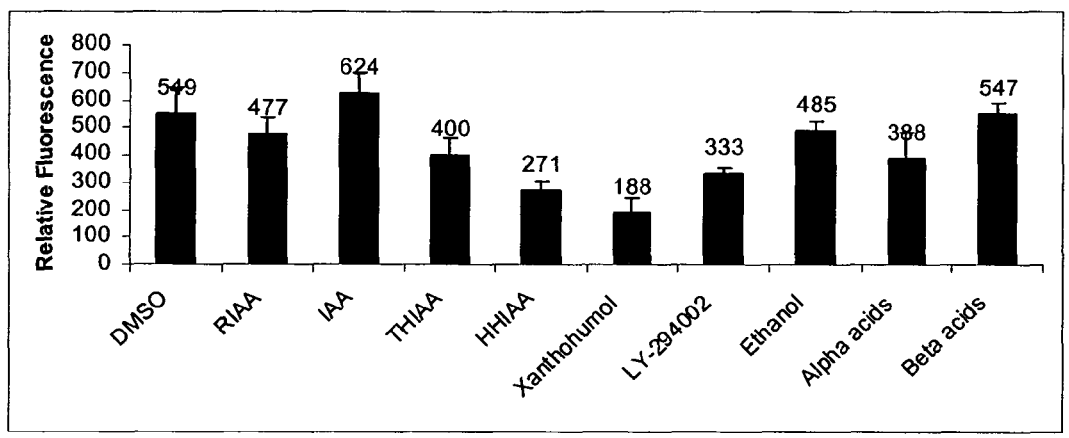
FIG. 24 graphically depicts the effects of 10 μg/ml of solvent control (DMSO), RIAA, isoalpha acid (IAA), tetrahydroisoalpha acid (THIAA), a 1:1 mixture of THIAA and hexahydroisoalpha acid (HHIAA), xanthohumol (XN), LY 249002 (LY), ethanol (ETOH), alpha acid (ALPHA), and beta acid (BETA) on cell proliferation in the RL 95-2 endometrial cell line.
Figure 24:
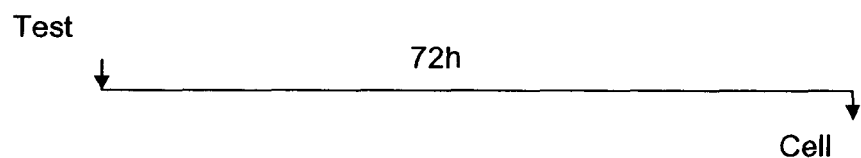
Figure 25:
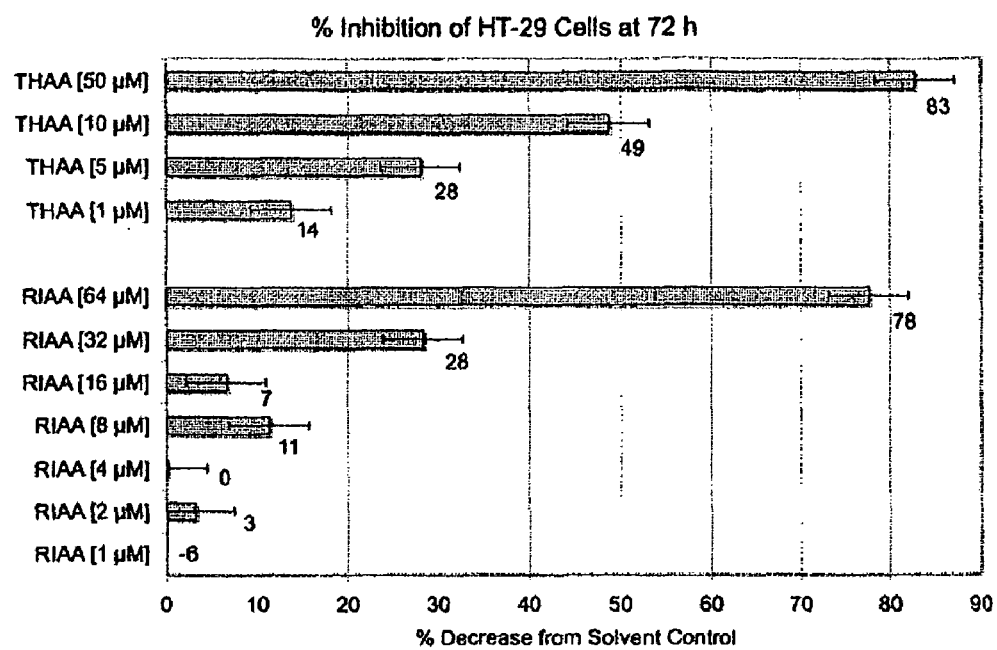
FIG. 25 graphically depicts the effects of various concentrations of THIAA or reduced isoalpha acids (RIAA) on cell proliferation in the HT-29 cell line.
Figure 26:
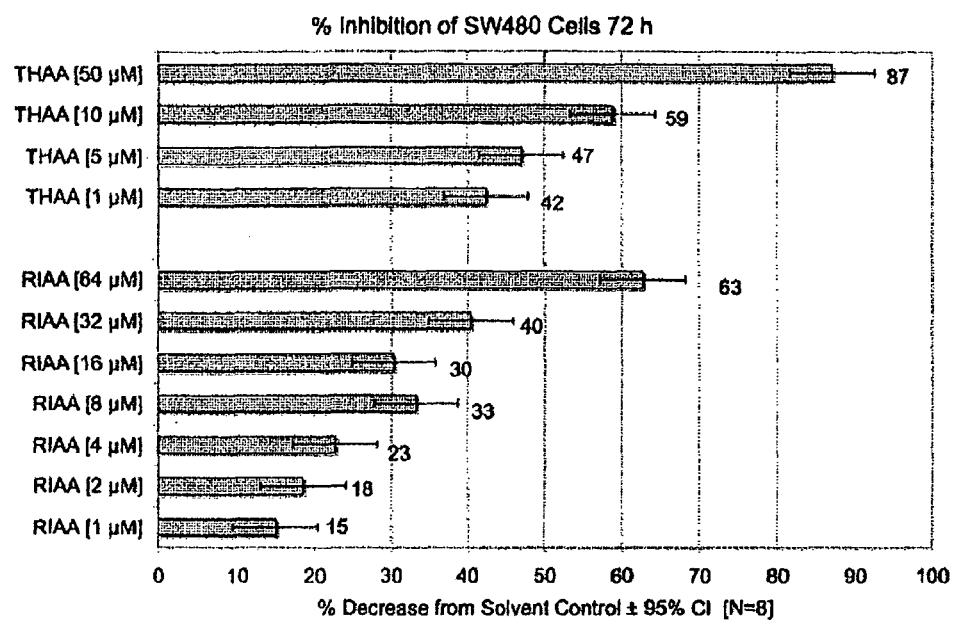
FIG. 26 graphically depicts the effects of various concentrations of THIAA or reduced isoalpha acids (RIAA) on cell proliferation in the SW480 cell line.

Results—RL 95-2 cells were treated for 72 hours with 10 μg/ml of MgDHIAA (mgRho), IAA, THIAA, TH-HHIAA (a 1:1 mixture of THIAA & HHIAA), Xn (xanthohumol), LY (LY 249002, a PI3K inhibitor), EtOH (ethanol), alpha (alpha acid mixture), and beta (beta acid mixture). The relative inhibition on cell proliferation is presented as FIG. 24, showing a greater than 50% inhibition for xanthohumol relative to the DMSO solvent control. FIGS. 25 & 26 display the dose response results for various concentrations of RIAA or THIAA on HT-29 and SW480 cancer cells respectively.

Median inhibitory concentrations for RIAA and THIAA were 31 and 10 µM for the HT-29 cell line and 38 and 3.2 µM for the SW480 cell line.

Example 33

In Vivo Hypoglycemic Action of *Acacia nilotica* and Hops Derivatives in the KK-A$^y$ Mouse Diabetes Model The Model—Male, nine-week old KK-A$^y$/Ta mice averaging 40±5 grams were used to assess the potential of the test materials to reduce fasting serum glucose or insulin concentrations. This mouse strain is the result of hybridization between the KK strain, developed in the 1940s as a model of diabetes and a strain of A$^y$/a genotype. The observed phenotype is the result of polygenic mutations that have yet to be fully characterized but at least four quantitative trait loci have been identified. One of these is linked to a missense mutation in the leptin receptor. Despite this mutation the receptor remains functional although it may not be fully efficient. The KK strain develops diabetes associated with insensitivity to insulin and glucose intolerance but not overt hyperglycemia. Introduction of the A$^y$ mutation induces obesity and hyperglycemia. The A$^y$ mutation is a 170 kb deletion of the Raly gene that is located 5' to the agouti locus and places the control for agouti under the Raly promoter. Homozygote animals die before implantation.

Test Materials—*Acacia nilotica* sample #5659 as described in Example 14 and hops derivatives Rho-isoalpha acids, isoalpha acids and xanthohumols as described in Example 20 were used. The *Acacia nilotica*, RIAA and IAA were administered at 100 mg/kg/day, while XN was dosed at 20 mg/kg. Additionally, 5:1 and 10:1 combinations of *Acacia nilotica* with RIAA, IAA and XN were formulated and dosed at 100 mg/kg/day.

Testing Procedure—Test substances were administered daily by gavage in 0.2% Tween-80 to five animals per group. Serum was collected from the retroorbital sinus before the initial dose and ninety minutes after the third and final dose. Non-fasting serum glucose was determined enzymatically by the mutarotase/glucose oxidase method and serum insulin was determined by a mouse specific ELISA (enzyme linked immunosorbent assay).

Data Analysis—To assess whether the test substances decreased either serum glucose or insulin relative to the controls, the post-dosing glucose and insulin values were first normalized relative to pre-dosing concentrations as percent pretreatment for each mouse. The critical value (one-tail, lower 95% confidence interval for the control mice) for percent pretreatment was computed for both the glucose and insulin variables. Each percent pretreatment value for the test materials was compared with the critical value of the control. Those percent pretreatment values for the test materials that were less than the critical value for the control were considered significantly different (p<0.05) from the control.

Results—During the three-day treatment period, non-fasting, serum glucose rose 2.6% while serum insulin decreased 6.7% in control mice. Rosigltiazone, *Acacia nilotica*, XN:*Acacia* [1:5], XN:*Acacia* [1:10], *Acacia*:RIAA [5:1], xanthohumols, *Acacia*:IAA [5:1], isomerized alpha acids and Rho-isoalpha acids all decreased non-fasting serum glucose relative to the controls with no effect on serum insulin. *Acacia*:RIAA [10:1] and *Acacia*:IAA [10:1] had no effect on either serum glucose or insulin (Table 30).

The rapid hypoglycemic effect of *Acacia nilotica* sample #5659, xanthohumols, isomerized alpha acids, Rho-isoalpha acids and their various combinations in the KK-Ay mouse model of type 2 diabetes supports their potential for clinical efficacy in the treatment of human diseases associated with hyperglycemia.

TABLE 30

Effect of *Acacia nilotica* and hops derivatives on non-fasting serum glucose and insulin in KK-Ay diabetic mice.

| Test Material | Dosing† [mg/kg-day] | Glucose [% Pretreatment] | Insulin [% Pretreatment] |
|---|---|---|---|
| Control (Critical Value) | — | 102.6 (98.7) | 93.3 (85.4) |
| Rosiglitazone | 1.0 | 80.3# | 88.7 |
| *Acacia nilotica* sample #5659 | 100 | 89.1# | 95.3 |
| XN:Acacia [1:5] | 100 | 91.5# | 106.5 |
| XN:Acacia [1:10] | 100 | 91.7# | 104.4 |
| Acacia:RIAA [5:1] | 100 | 92.6# | 104.8 |
| Xanthohumols | 20 | 93.8# | 106.4 |
| Acacia:IAA [5:1] | 100 | 98.0# | 93.2 |
| Isomerized alpha acids | 100 | 98.1# | 99.1 |
| Rho-isoalpha acids | 100 | 98.3# | 100 |
| Acacia:RIAA [10:1] | 100 | 101.6 | 109.3 |
| Acacia:IAA [10:1] | 100 | 104.3 | 106.4 |

†Dosing was performed once daily for three consecutive days on five animals per group.
Significantly less than control (p < 0.05).

Example 34

In Vivo Synergy of *Acacia nilotica* and Hops Derivatives in the Diabetic db/db Mouse Model The Model—Male, C57BLKS/J m$^+$/m$^+$ Lepr$^{db}$ (db/db) mice were used to assess the potential of the test materials to reduce fasting serum glucose or insulin concentrations. This strain of mice is resistant to leptin by virtue of the absence of a functioning leptin receptor. Elevations of plasma insulin begin at 10 to 14 days and of blood sugar at 4 to 8 weeks. At the time of testing (9 weeks) the animals were markedly obese 50±5 g and exhibited evidence of islet hypertrophy.

Test Materials—The positive controls metformin and rosiglitazone were dosed, respectively, at 300 mg/kg-day and 1.0 mg/kg-day for each of three consecutive days. *Acacia nilotica* sample #5659, hops derivatives and their combinations were dosed as described previously.

Testing Procedure—Test substances were administered daily by gavage in 0.2% Tween-80. Serum was collected from the retroorbital sinus before the initial dose and ninety minutes after the third and final dose. Non-fasting serum glucose was determined enzymatically by the mutarotase/glucose oxidase method and serum insulin was determined by a mouse specific ELISA.

Results—The positive controls metformin and rosiglitazone decreased both serum glucose and insulin concentrations relative to the controls (Table 31). Only RIAA and XN demonstrated acceptable results as single test materials. RIAA reduced serum insulin, while XN produced a reduction in serum glucose with no effect on insulin. *Acacia*:RIAA [5:1] was the most effective agent tested for reducing serum insulin concentrations, providing a 21 percent reduction in serum insulin levels versus a 17 percent reduction in insulin concentrations by the biguanide metformin and a 15 percent decrease by the thiazolidinedione rosiglitazone. The response of this *Acacia*:RIAA [5:1] combination was greater than the responses of either individual component thus exhibiting a potential for synergy. *Acacia nilotica* alone failed to reduce either serum glucose or insulin, while RIAA reduced serum insulin to a similar extent as metformin. Of the remaining test materials, the *Acacia*:IAA [10:1] combination was also effective in reducing serum insulin concentrations.

The rapid reduction of serum insulin affected by Rho-isoalpha acids and reduction of serum glucose by xanthohumols in the db/db mouse model of type 2 diabetes supports their potential for clinical efficacy in the treatment of human diseases associated with insulin insensitivity and hyperglycemia. Further, the 5:1 combination of Rho-isoalpha acids and *Acacia catechu* appeared synergistic in the db/db murine diabetes model. The positive responses exhibited by Rho-isoalpha acids, xanthohumols and the *Acacia*:RIAA [5:1] formulation in two independent animal models of diabetes and three in vitro models supports their potential usefulness in clinical situations requiring a reduction in serum glucose or enhance insulin sensitivity.

TABLE 31

Effect of *Acacia nilotica* and hops derivatives on non-fasting serum glucose and insulin in db/db diabetic mice.

| Test Material | Dosing† [mg/kg-day] | Glucose [% Pretreatment] | Insulin [% Pretreatment] |
| --- | --- | --- | --- |
| Control (Critical Value) | — | 103.6 (98.4) | 94.3 (84.9) |
| Acacia:RIAA [5:1] | 100 | 99.6 | 79.3# |
| Metformin | 300 | 67.6# | 83.3# |
| Rho-isoalpha acids | 100 | 102.3 | 83.8# |
| Acacia:IAA [10:1] | 100 | 104.3 | 84.4# |
| Rosiglitazone | 1.0 | 83.0# | 84.7# |
| XN:Acacia [1:10] | 100 | 101.5 | 91.1 |
| Acacia nilotica sample#5659 | 100 | 100.4 | 91.9 |
| Acacia:RIAA [10:1] | 100 | 101.6 | 93.5 |
| Isomerized alpha acids | 100 | 100.8 | 95.8 |
| Xanthohumols | 20 | 97.8# | 101.6 |
| XN:Acacia [1:5] | 100 | 104.1 | 105.6 |
| Acacia:IAA [5:1] | 100 | 102.7 | 109.1 |

†Dosing was performed once daily for three consecutive days on five animals per group.
Significantly less than respective control (p < 0.05).

Example 35

In Vivo Optimization of *Acacia nilotica* and Hops Derivative Ratio in the Diabetic db/db Mouse Model The Model—Male, C57BLKS/J m+/m+ Leprdb (db/db) mice were used to assess the potential of the test materials to reduce fasting serum glucose or insulin concentrations. This strain of mice is resistant to leptin by virtue of the absence of a functioning leptin receptor. Elevations of plasma insulin begin at 10 to 14 days and of blood sugar at 4 to 8 weeks. At the time of testing (9 weeks) the animals were markedly obese 50±5 g and exhibited evidence of islet hypertrophy.

Test Materials—The positive controls metformin and rosiglitazone were dosed, respectively, at 300 mg/kg-day and 1.0 mg/kg-day for each of five consecutive days. The hops derivative RIAA and *Acacia nilotica* sample #5659 in ratios of 1:99, 1:5, 1:2, 1:1, 2:1, and 5:1 were dosed at 100 mg/kg.

Testing Procedure—Test substances were administered daily by gavage in 0.2% Tween-80. Serum was collected from the retroorbital, sinus before the initial dose and ninety minutes after the fifth and final dose. Non-fasting serum glucose was determined enzymatically by the mutarotase/glucose oxidase method and serum insulin was determined by a mouse specific ELISA.

Figure 27:
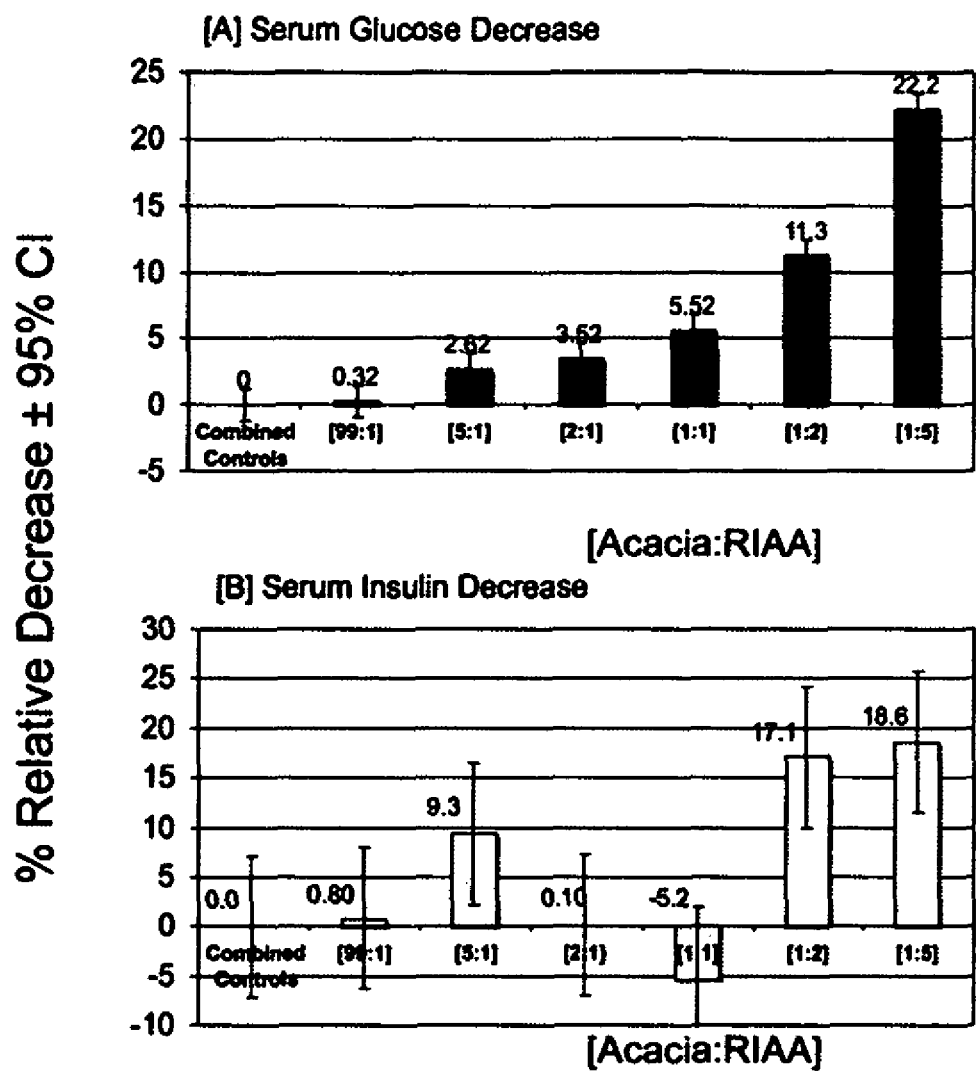
FIG. 27 graphically depicts the dose responses of various combinations of reduced isoalpha acids (RIAA) and *Acacia* for reducing serum glucose [panel A] and serum insulin [panel B] in the db/db mouse model.

Results—The positive controls metformin and rosiglitazone decreased both serum glucose and insulin concentrations relative to the controls (p<0.05, results not shown). Individually, RIAA and *Acacia* at 100 mg/kg for five days reduced serum glucose, respectively, 7.4 and 7.6 percent relative to controls (p<0.05). Combinations of RIAA and *Acacia* at 1:99, 1:5 or 1:1 appeared antagonistic, while 2:1 and 5:1 ratios of RIAA:*Acacia* decreased serum glucose, respectively 11 and 22 percent relative to controls. This response was greater than either RIAA or *Acacia* alone and implies a synergic effect between the two components. A similar effect was seen with decreases in serum insulin concentrations (FIG. 27).

Figure 28:
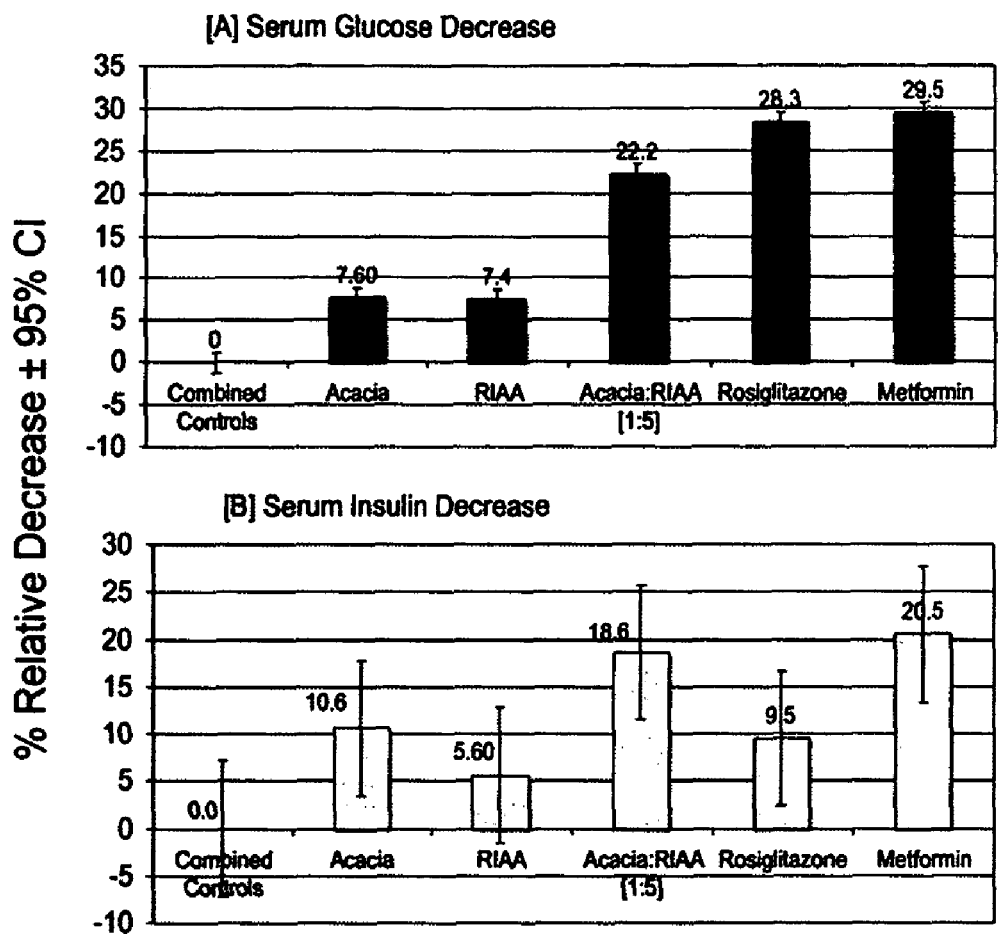
FIG. 28 graphically depicts the reduction in serum glucose [panel A] and serum insulin [panel B] in the db/db mouse model produced by a 5:1 combination of RIAA:*Acacia* as compared to the pharmaceutical anti-diabetic compounds roziglitazone and metformin.

A 5:1 combination of Rho-isoalpha acids and *Acacia* was additionally tested in this model against metformin and roziglitazone, two pharmaceuticals currently in use for the treatment of diabetes. The results (FIG. 28) indicate that the 5:1 combination of Rho-isoalpha acids and *Acacia* produced results compatible to the pharmaceutical agents in reducing serum glucose (panel A) and serum insulin (panel B).

The 2:1 and 5:1 combinations of Rho-isoalpha acids and *Acacia* appeared synergistic in the db/db murine diabetes model, supporting their potential usefulness in clinical situations requiring a reduction in serum glucose or enhance insulin sensitivity.

Example 36

Effects of Hops Test Compounds in a Collagen Induced Rheumatoid Arthritis Murine Model This example demonstrates the efficacy of two hops compounds, Mg Rho and THIAA, in reducing inflammation and arthritic symptomology in a rheumatoid arthritis model, such inflammation and symptoms being known to mediated, in part, by a number of protein kinases.

The Model—Female DBA/J mice (10/group) were housed under standard conditions of light and darkness and allow diet ad libitum. The mice were injected intradermally on day 0 with a mixture containing 100 μg of type II collagen and 100 μg of *Mycobacterium tuberculosis* in squalene. A booster injection was repeated on day 21. Mice were examined on days 22-27 for arthritic signs with nonresponding mice removed from the study. Mice were treated daily by gavage with test compounds for 14 days beginning on day 28 and ending on day 42. Test compounds, as used in this example were RIAA (MgRho) at 10 mg/kg (lo), 50 mg/kg (med), or 250 mg/kg (hi); THIAA at 10 mg/kg (lo), 50 mg/kg (med), or 250 mg/kg (hi); celecoxib at 20 mg/kg; and prednisilone at 10 mg/kg.

Arthritic symptomology was assessed (scored 0-4) for each paw using a arthritic index as described below. Under this arthritic index 0=no visible signs; 1=edema and/or erythema: single digit; 2=edema and or erythema: two joints; 3=edema and or erythema: more than two joints; and 4=severe arthritis of the entire paw and digits associated with ankylosis and deformity.

Figure 29:
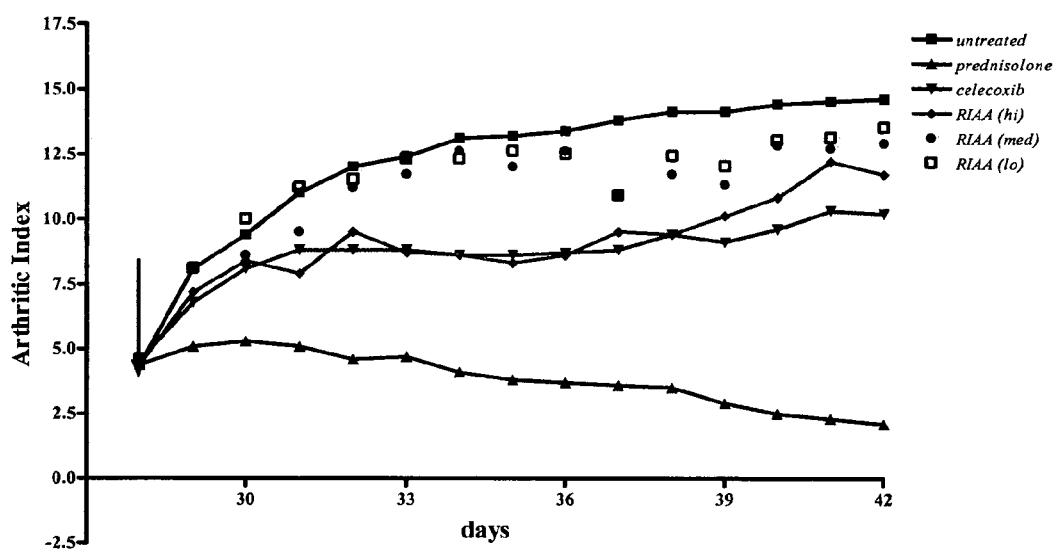
FIG. 29 graphically depicts the effects of reduced isoalpha acids (RIAA) on the arthritic index in a murine model of rheumatoid arthritis.
Figure 30:
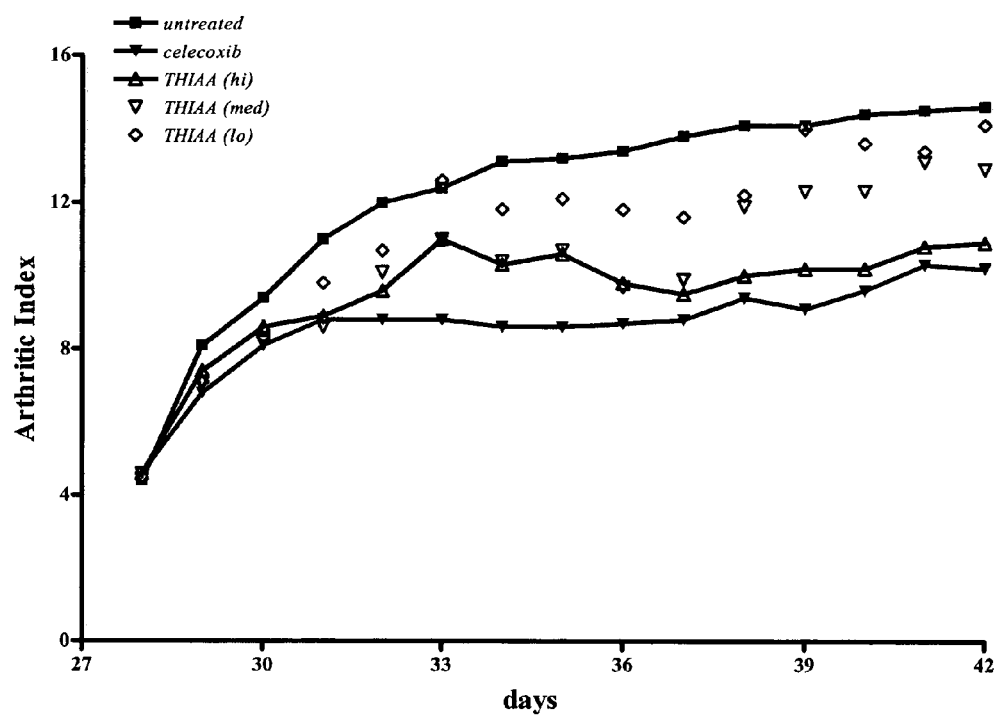
FIG. 30 graphically depicts the effects of THIAA on the arthritic index in a murine model of rheumatoid arthritis.

Results—The effect of RIAA on the arthritic index is presented graphically as FIG. 29. Significant reductions (p<0.05, two tail t-test) were observed for prednisolone at 10 mg/kg (days 30-42), celecoxib at 20 mg/kg (days 32-42), RIAA at 250 mg/kg (days 34-42) and RIAA at 50 mg/kg (days 38-40), demonstrating antiarthritc efficacy for RIAA at 50 or 250 mg/kg . FIG. 30 displays the effects of THIAA on the arthritic index. Here, significant reductions were observed for celecoxib (days 32-42), THIAA at 250 mg/kg (days 34-42) and THIAA at 50 mg/kg (days 34-40), also demonstrating the effectiveness of THIAA as an antiarthritic agent.

Example 37

RIAA:*Acacia* (1:5) Effects on Metabolic Syndrome in Humans

This experiment examined the effects treatment with a RIAA:*Acacia* (1:5) formulation on a number of clinically relevant markers in volunteer patients with metabolic syndrome.

Methods and Trial Design—This trial was a randomized, placebo-controlled, double-blind trial conducted at a single study site (the Functional Medicine Research Center, Gig Harbor, Wash.). Inclusion criteria for the study required subjects (between 18 to 70 years of age) satisfy the following: (i) BMI between 25 and 42.5 kg/m$^2$; (ii) TG/HDL-C ratio$\geq$3.5; (iii) fasting insulin$\geq$10 mcIU/mL. In addition, subjects had to meet 3 of the following 5 criteria: (i) waist circumference > 35" (women) and >40" (men); (ii). TG$\geq$150 mg/dL; (-iii) HDL<50 mg/dL (women), and <40 mg/dL (men); (iv) blood pressure $\geq$130/85 or diagnosed hypertension on medication; and (v) fasting glucose $\geq$100 mg/dL.

Subjects who satisfied the inclusion criteria were randomized to one of 4 arms: (i) subjects taking the RIAA/*Acacia* combination (containing 100 mg RIAA and 500 mg *Acacia nilotica* heartwood extract per tablet) at 1 tablet t.i.d.; (ii) subjects taking the RIAA/*Acacia* combination at 2 tablets t.i.d; (iii) placebo, 1 tablet, t.i.d; and (iv) placebo, 2 tablets, t.i.d. The total duration of the trial was 12 weeks. Blood was drawn from subjects at Day 1, at 8 weeks, and 12 weeks to assess the effect of supplementation on various parameters of metabolic syndrome.

Results—The initial demographic and biochemical characteristics of subjects (pooled placebo group and subjects taking RIAA/*Acacia* at 3 tablets per day) enrolled for the trial are shown in Table 32. The initial fasting blood glucose and 2 h post-prandial (2 h pp) glucose values were similar between the RIAA/*Acacia* and placebo groups (99.0 vs. 96.5 mg/dL and 128.4 vs. 109.2 mg/dL, respectively). In addition, both glucose values were generally within the laboratory reference range (40-110 mg/dL for fasting blood glucose and 70-150 mg/dL for 2 h pp glucose). This was expected, because alteration in 2 h pp insulin response precedes the elevations in glucose and fasting insulin that are seen in later stage metabolic syndrome and frank diabetes.

TABLE 32

Demographic and Baseline Biochemical Characteristics

|  | Placebo | | RIAA/*Acacia* (3 tablets/day) | |
|---|---|---|---|---|
| N | 35 | | 35 | |
| Gender | | | | |
| Male | 11 (31%) | | 12 (34%) | |
| Female | 24 (69%) | | 23 (66%) | |
|  | Mean | SD | Mean | SD |
| Age (yrs) | 46.0 | 13.2 | 47.9 | 13.4 |
| Weight (lbs) | 220.6 | 35.2 | 219.5 | 31.6 |
| BMI (kg/m$^2$) | 35.0 | 4.0 | 35.4 | 4.0 |
| Systolic BP (mm) | 131.0 | 15.1 | 129.7 | 13.9 |
| Diastolic BP (mm) | 83.7 | 8.5 | 82.6 | 7.8 |
| Waist (inches) | 42.9 | 4.9 | 42.9 | 4.5 |

TABLE 32-continued

Demographic and Baseline Biochemical Characteristics

| Hip (inches) | 47.1 | 4.0 | 47.6 | 3.2 |
|---|---|---|---|---|
| Fasting Insulin (mcIU/mL) | 13.2 | 5.2 | 17.5 | 12.1 |
| 2 h pp Insulin (mcIU/mL) | 80.2 | 52.1 | 99.3* | 59.2* |
| Fasting Glucose (mg/dL) | 96.5 | 9.0 | 99.0 | 10.3 |
| 2 h pp Glucose (mg/dL) | 109.2 | 30.5 | 128.4 | 36.9 |
| Fasting TG (mg/dL) | 231.2 | 132.2 | 255.5 | 122.5 |

Figure 31:
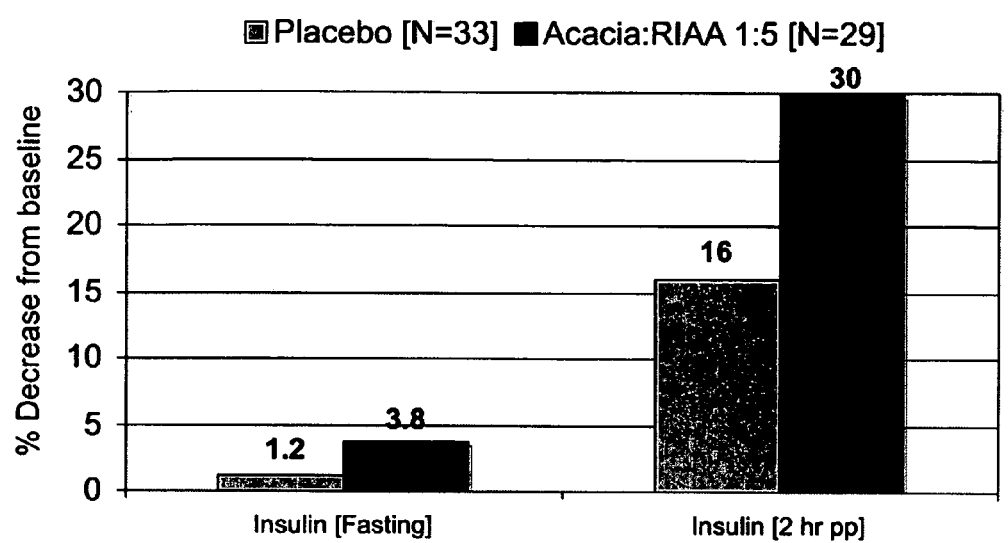
FIG. 31 graphically depicts the effects of RIAA/*Acacia* (1:5) supplementation (3 tablets per day) on fasting and 2 h post-prandial (pp) insulin levels. For the 2 h pp insulin level assessment, subjects presented after a 10-12 h fast and consumed a solution containing 75 g glucose (Trutol 100, CASCO NERL® Diagnostics); 2 h after the glucose challenge, blood was drawn and assayed for insulin levels (Laboratories Northwest, Tacoma, Wash.).
Figure 32:
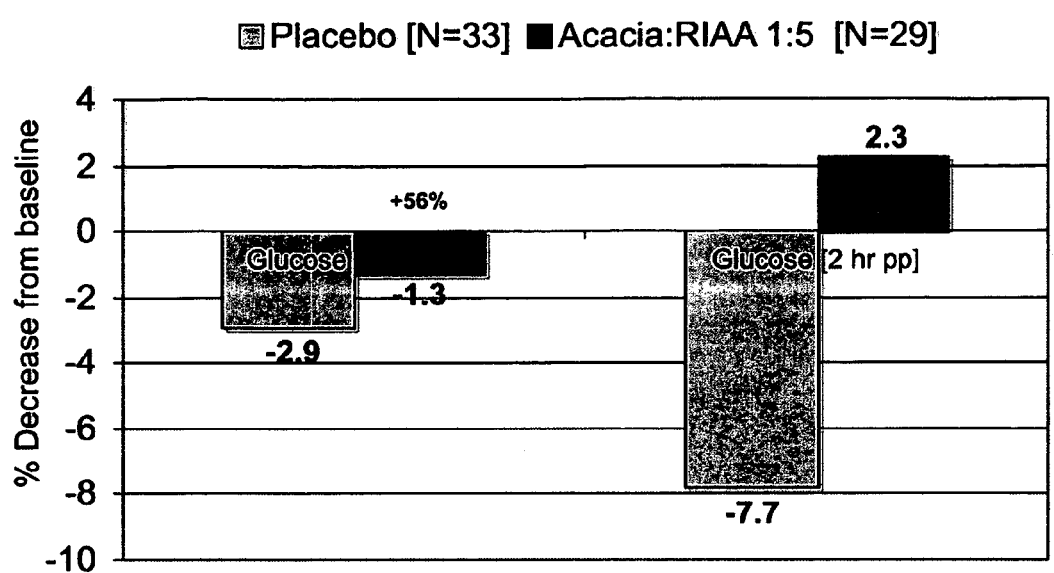
FIG. 32 graphically depicts the effects of RIAA/*Acacia* (1:5) supplementation (3 tablets per day) on fasting and 2 h pp glucose levels. For the 2 h pp glucose level assessment, subjects presented after a 10-12 h fast and consumed a solution containing 75 g glucose (Trutol 100, CASCO NERL® Diagnostics); 2 h after the glucose challenge, blood was drawn and assayed for glucose levels (Laboratories Northwest, Tacoma, Wash.).

*One subject was excluded from the analysis because of abnormal 2 h pp insulin values;
BMI, Basal Metabolic Index;
BP, Blood Pressure;
TG, Triglyceride;
HDL, High-Density Lipoprotein Fasting blood insulin measurements were similar and generally within the reference range as well, with initial values of 17.5 mcIU/mL for the RIAA/*Acacia* group, and 13.2 mcIU/mL for the placebo group (reference range 3-30 mcIU/mL). The 2 h pp insulin levels were elevated past the reference range (99.3 vs. 80.2 mcIU/mL), and showed greater variability than did the fasting insulin or glucose measurements. Although the initial values were similar, the RIAA/*Acacia* group showed a greater decrease in fasting insulin and 2 h pp insulin, as well as 2 h pp blood glucose after 8 weeks on the protocol (FIGS. 31 and 32).

Figure 33:
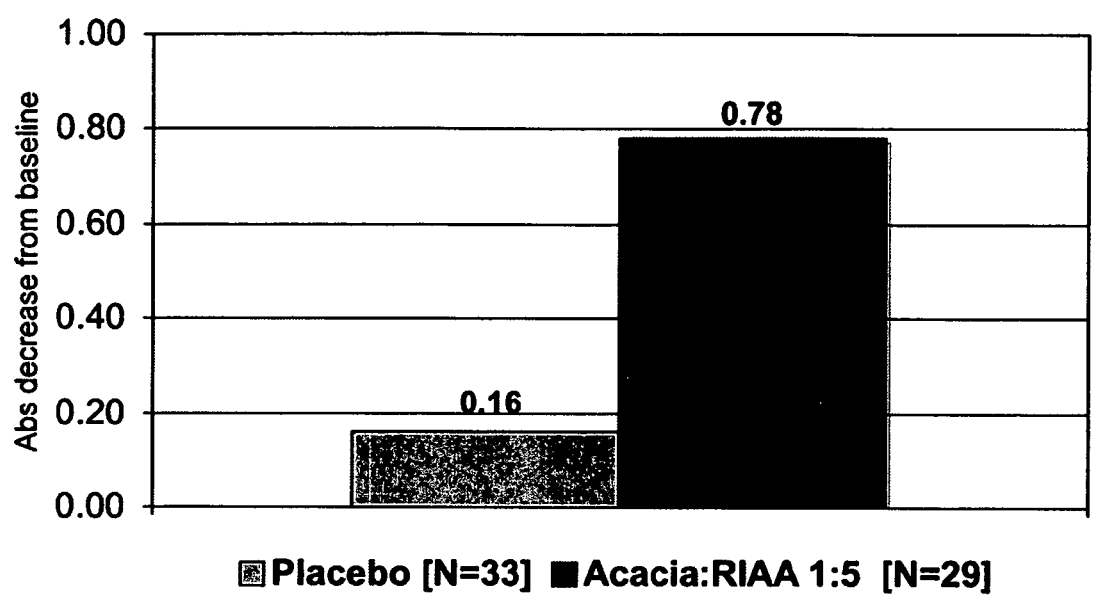
FIG. 33 graphically depicts the effects of RIAA/*Acacia* (1:5) supplementation (3 tablets per day) on HOMA scores. HOMA score was calculated from fasting insulin and glucose by published methods [(insulin (mcIU/mL)*glucose (mg/dL))/405].

The homeostatic model assessment (HOMA) score is a published measure of insulin resistance. The change in HOMA score for all subjects is shown in FIG. 33. Due to the variability seen in metabolic syndrome subjects' insulin and glucose values, a subgroup of only those subjects with fasting insulin >15 mcIU/mL was also assessed. The HOMA score for this subgroup is shown in Table 33, and indicates that a significant decrease was observed for the RIAA/*Acacia* group as compared to the placebo group.

TABLE 33

Effect of RIAA/Acacia supplementation (3 tablets/day) on HOMA scores in subjects with initial fasting insulin $\geq$15 mcIU/mL.

| | | HOMA Score | |
|---|---|---|---|
| Treatment | N | Initial | After 8 Weeks |
| Placebo | 9 | 4.39 | 4.67 |
| RIAA/Acacia | 13 | 5.84 | 4.04 |

The difference between the groups was significant at 8 weeks (p <0.05). HOMA score was calculated from fasting insulin and glucose by published methods [(insulin (mcIU/mL)*glucose (mg/dL))/405].

Figure 34:
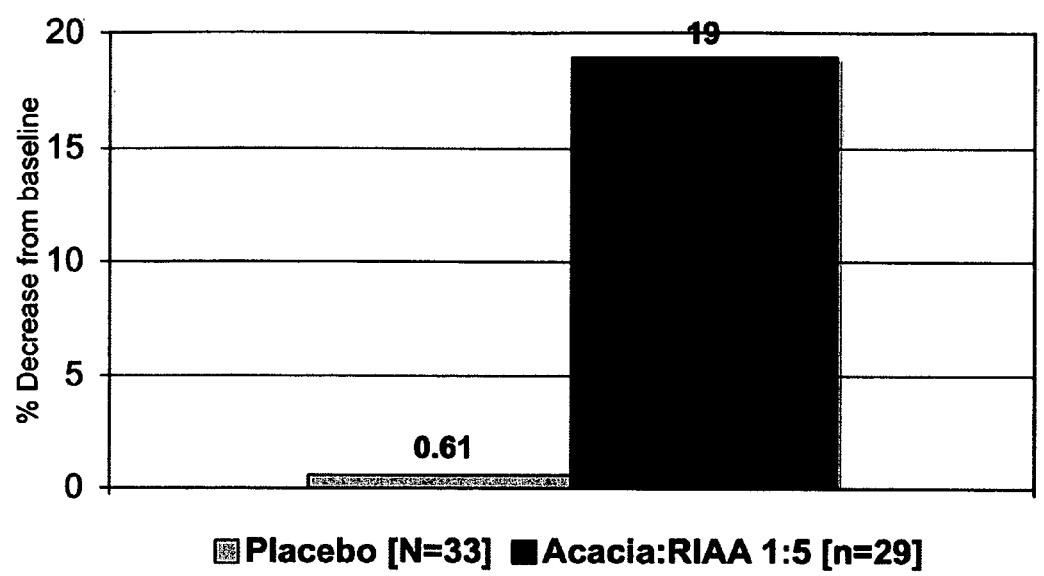
FIG. 34 graphically depicts the effects of RIAA/*Acacia* (1:5) supplementation (3 tablets per day) on serum TG levels.

Elevation in triglycerides (TG) is also an important suggestive indicator of metabolic syndrome. Table 34 and FIG. 34 indicate that RIAA/*Acacia* supplementation resulted in a significant decrease in TG after 8 weeks as compared with placebo (p<0.05). The TG/HDL-C ratio was also shown to decrease substantially for the RIAA/*Acacia* group (from 6.40 to 5.28), while no decrease was noted in the placebo group (from 5.81 to 5.92).

TABLE 34

Effect of RIAA/Acacia supplementation (3 tablets/day) on TG levels and TG/HDL-Cholesterol ratio.

| Supplementation | Fasting TG (mg/dL) | | | TG/HDL | | |
|---|---|---|---|---|---|---|
| | Initial | After 8 Weeks | Change | Initial | After 8 Weeks | Change |
| Placebo | 231.2 | 229.8 | −1.4 | 5.81 | 5.92 | +0.11 |
| RIAA/Acacia (3 tablets per day) | 258.6 | 209.6 | −49.0 | 6.40 | 5.28 | −1.12 |

Supplementation of metabolic syndrome subjects with a combination tablet composed of 100 mg rho-iso-alpha acids and 500 mg *Acacia nilotica* heartwood extract at 3 tablets per day for a duration of 8 weeks led to greater reduction of 2 h pp insulin levels, as compared to placebo. Further, greater decreases of fasting insulin, fasting and 2 h pp glucose, fasting triglyceride and HOMA scores were observed in subjects taking RIAA/*Acacia* supplement (3 tablets per day) versus subjects taking placebo. These results indicate RIAA/*Acacia* supplementation might be useful in maintaining insulin homeostasis in subjects with metabolic syndrome.

The invention now having been fully described, it will be apparent to one of ordinary skill in the art that many changes and modifications can be made thereto without departing from the spirit or scope of the appended claims.

The invention claimed is:

1. A method of reducing serum glucose level in a subject in need thereof, said method comprising administering to the subject a therapeutically effective amount of a composition comprising about 5:1 ratio of reduced-isoalpha acids to *Acacia* extract.

2. The method of claim 1, wherein the reduced isoalpha acid is selected from the group consisting of dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, hexahydro-isoadhumulone, and rho-isoalpha acids.

3. The method of claim 1, wherein the composition further comprises a pharmaceutically acceptable excipient selected from the group consisting of coatings, isotonic and absorption delaying agents, binders, adhesives, lubricants, disintegrants, coloring agents, flavoring agents, sweetening agents, absorbents, detergents, and emulsifying agents.

4. The method of claim 1, wherein the composition further comprises one or more members selected from the group consisting of antioxidants, vitamins, minerals, proteins, fats, and carbohydrates.

5. The method of claim 1, wherein the composition further comprises an antidiabetic drug selected from the group consisting of rosiglitazone, troglitazone, pioglitazone, and metformin.

\* \* \* \* \*

UNITED STATES PATENT AND TRADEMARK OFFICE
CERTIFICATE OF CORRECTION

PATENT NO.       : 8,263,139 B2
APPLICATION NO.  : 11/501393
DATED            : September 11, 2012
INVENTOR(S)      : Matthew L. Tripp et al.

It is certified that error appears in the above-identified patent and that said Letters Patent is hereby corrected as shown below:

Title page, item (73); Assignee: should read: Metaproteomics, LLC.

Signed and Sealed this
Thirty-first Day of December, 2013

Margaret A. Focarino
*Commissioner for Patents of the United States Patent and Trademark Office*